United States Patent
Vielhaber et al.

(10) Patent No.: US 9,072,676 B2
(45) Date of Patent: Jul. 7, 2015

(54) CYCLOHEXYL CARBAMATE COMPOUNDS AS SKIN AND/OR HAIR LIGHTENING ACTIVES

(75) Inventors: Gabriele Vielhaber, Paris (FR); Heiko Oertling, Lausanne (CH); Nicole Titze, Holzminden (DE); Claudia Gömann, Golmbach-Warbsen (DE); Rahim Brodhage, Höxter (DE)

(73) Assignee: SYMRISE AG, Holzminden (DE)

( * ) Notice: Subject to any disclaimer, the term of this patent is extended or adjusted under 35 U.S.C. 154(b) by 126 days.

(21) Appl. No.: 13/699,494

(22) PCT Filed: May 25, 2010

(86) PCT No.: PCT/EP2010/057115
§ 371 (c)(1),
(2), (4) Date: Feb. 7, 2013

(87) PCT Pub. No.: WO2010/122178
PCT Pub. Date: Oct. 28, 2010

(65) Prior Publication Data
US 2013/0156710 A1    Jun. 20, 2013

(51) Int. Cl.
| A61Q 5/08 | (2006.01) |
| A61Q 19/02 | (2006.01) |
| A61K 8/44 | (2006.01) |
| A61K 8/42 | (2006.01) |
| C08L 5/00 | (2006.01) |
| A61K 31/27 | (2006.01) |
| A61K 45/06 | (2006.01) |
| A61Q 17/04 | (2006.01) |

(52) U.S. Cl.
CPC ... *A61K 8/44* (2013.01); *A61K 8/42* (2013.01); *A61K 8/445* (2013.01); *A61Q 19/02* (2013.01); *C08L 5/00* (2013.01); *A61K 31/27* (2013.01); *A61K 45/06* (2013.01); *A61Q 17/04* (2013.01)

(58) Field of Classification Search
None
See application file for complete search history.

(56) References Cited

U.S. PATENT DOCUMENTS

| 2002/0107282 A1 | 8/2002 | Chevalier et al. | |
| 2002/0161041 A1* | 10/2002 | Browning et al. | 514/489 |
| 2003/0011990 A1 | 1/2003 | Lai et al. | |
| 2006/0142382 A1* | 6/2006 | Morimoto et al. | 514/474 |
| 2008/0255178 A1 | 10/2008 | Schrimpf et al. | |
| 2009/0311401 A1* | 12/2009 | Ley et al. | 426/533 |
| 2011/0294876 A1* | 12/2011 | Kuper et al. | 514/465 |
| 2013/0137710 A1* | 5/2013 | Meyer et al. | 514/263.34 |

FOREIGN PATENT DOCUMENTS

| DE | 2934355 A1 | 3/1981 |
| JP | 2002-193726 A | 7/2002 |

(Continued)

OTHER PUBLICATIONS

International search report with references cited and written opinion under Rule 43 PCT attached to the search report, International Application No. PCT/EP2010/057115, filed May 25, 2010.
English Translation of Second Office Action from the Chinese Patent Office issued in Chinese Patent Application No. 201080068216.1 on Sep. 29, 2014.
Search Report, Chinese Patent Application No. 201080068216.1, dated Sep. 22, 2014.
Third Office Action from the Chinese Patent Office issued in Chinese Patent Application No. 201080068216.1, issued on Jan. 28, 2015.

*Primary Examiner* — Jyothsna Venkat
(74) *Attorney, Agent, or Firm* — Novak Druce Connolly Bove + Quigg LLP

(57) ABSTRACT

The present invention relates to the cosmetic, dermatological or therapeutic use of certain cyclohexyl carbamate compounds of formula (I) given below, preferably as skin and/or hair lightening (whitening) actives. The invention further relates to compositions and cosmetic, dermatological or therapeutic products comprising one or more compounds of formula (I) suitable for lightening human skin and/or hair and corresponding methods. The invention further relates to compounds of formula (I) as a drug, their use for the preparation of a pharmaceutical composition for lightening human skin and/or hair and to novel compounds of formula (I)

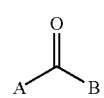

(I)

wherein A denotes

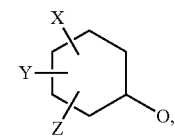

wherein X, Y and Z independently of one another denote hydrogen, C1-C4-alkyl or C2-C4-alkenyl,
wherein optionally two of the radicals X, Y and Z are covalently bonded to one another under formation of a bicyclic ring system, in such a bicyclic ring system two of the radicals X, Y and Z together preferably form a radical having 1 to 4 carbon atoms, preferably a hydrocarbon radical having 1 to 3 carbon atoms,
B denotes $NR^1R^2$, wherein
$R^1$ denotes hydrogen or an organic radical having 1 to 14 carbon atoms,
$R^2$ denotes an organic radical having 1 to 14 carbon atoms, and
wherein optionally $R^1$ and $R^2$ are covalently bonded to one another, preferably so that B is a 3 to 8 membered ring.

14 Claims, No Drawings

(56) References Cited

FOREIGN PATENT DOCUMENTS

| JP | 2003-535915 A | 12/2003 |
| JP | 2004501950 A | 1/2004 |
| JP | 2006511484 A | 4/2006 |
| JP | 2007503392 A | 2/2007 |
| JP | 2009144179 A | 7/2009 |
| JP | 2013533218 A | 8/2013 |
| WO | WO-9721678 A1 | 6/1997 |
| WO | WO 01/66105 | * 9/2001 |
| WO | WO-2009144179 A1 | 12/2009 |

* cited by examiner

CYCLOHEXYL CARBAMATE COMPOUNDS AS SKIN AND/OR HAIR LIGHTENING ACTIVES

CROSS-REFERENCE TO RELATED APPLICATIONS

This application is a national stage application (under 35 U.S.C. §371) of PCT/EP2010/057115, filed May 25, 2010, which is incorporated herein by reference in its entirety.

The present invention relates to the cosmetic, dermatological or pharmaceutical (therapeutic) use of certain cyclohexyl carbamate compounds of formula (I) given below, preferably as skin and/or hair lightening (whitening) actives. The invention further relates to compositions and cosmetic, dermatological or pharmaceutical preparations (compositions) comprising one or more compounds of formula (I) suitable for lightening human skin and/or hair and corresponding methods. The invention further relates to compounds of formula (I) as a drug, their use for the preparation of a pharmaceutical composition for lightening human skin and/or hair and to novel compounds of formula (I).

Skin-lightening active ingredients intervene in one form or another in melanin metabolism or catabolism. Melanin pigments, which are normally brown to black in colour, are formed in the melanocytes of the skin, transferred to the keratinocytes and give the skin or hair its colour. In mammals, the brown-black eumelanins are primarily formed from hydroxy-substituted aromatic amino acids such as L-tyrosine and L-DOPA, the yellow to red pheomelanins additionally from sulfur-containing molecules (Cosmetics & Toiletries 1996, 111 (5), 43-51). Starting from L-tyrosine, L-3,4-dihydroxyphenylalanine (L-DOPA) is formed by the copper-containing key enzyme tyrosinase and is in turn converted by tyrosinase to dopachrome. By a series of steps catalysed by various enzymes, the latter is oxidised to form melanin.

Skin-lightening agents are used for various reasons: if for some reason the melanin-forming melanocytes in human skin are not evenly distributed, pigment spots occur which are either lighter or darker than the surrounding skin area. To overcome this problem, skin and hair lightening agents are sold which at least partially help to balance out such pigment spots. In addition, many people have a need to lighten their naturally dark skin colour or to prevent skin pigmentation. This requires very safe and effective skin and hair lightening agents. Many skin and hair lightening agents contain more or less powerful tyrosinase inhibitors. This is only one possible route towards skin and hair lightening, however.

Furthermore, UV-absorbing substances are also used to protect against the increase in skin pigmentation caused by UV light. This is a purely physically induced effect, however, and must be distinguished from the biological action of skin-lightening agents on cellular melanin formation, which can also be detected in the absence of UV light. Moreover, UV absorbers do not bring about a true lightening of the skin but merely inhibit the increase in skin pigmentation caused by UV light.

Cosmetic or pharmaceutical (therapeutic) preparations with skin and/or hair lightening activity are known from the prior art.

U.S. Pat. No. 4,959,393 discloses 4-alkyl-resorcinols as skin and/or hair lightening agents.

WO 2004/105736 teaches certain diphenylmethane-derivatives as skin and/or hair lightening agents.

WO 2007/110415 proposes certain diacetyl trimers as skin and/or hair lightening agents.

Hydroquinone, hydroquinone derivatives such as e.g. arbutin, vitamin C, derivatives of ascorbic acid such as e.g. ascorbyl palmitate, kojic acid and derivatives of kojic acid such as e.g. kojic acid dipalmitate, are used in particular in commercial cosmetic or therapeutic skin and hair lightening preparations.

One of the most commonly used skin and hair lighteners is hydroquinone. However, this compound has a cytotoxic effect on melanocytes and is irritating to the skin. For that reason such preparations are no longer authorised for cosmetic applications in Europe, Japan and South Africa, for example. In addition, hydroquinone is very sensitive to oxidation and can be stabilised only with difficulty in cosmetic formulations.

Arbutin (beta-arbutin) is a hydroquinone glucoside, which hydrolyses in situ to form hydroquinone and is therefore just as questionable in toxicological terms as hydroquinone.

Vitamin C and ascorbic acid derivatives have only an inadequate effect on the skin. Furthermore, they do not act directly as tyrosinase inhibitors but instead reduce the coloured intermediate stages of melanin biosynthesis.

Kojic acid (5-hydroxy-2-hydroxymethyl-4-pyranone) is a tyrosinase inhibitor which inhibits its catalytic action by chelating the copper atoms in the enzyme; it is used in commercial skin and hair lightening agents but has a high sensitising potential and causes contact allergies.

The object of the present invention was to remedy the disadvantages of the prior art and in particular to provide effective skin and/or hair lightening actives, in particular skin lightening actives, which preferably achieve skin and/or hair lightening activity which preferably is not based on tyrosinase inhibition.

It has surprisingly been found that this object can be achieved by using compounds of formula (I) or a cosmetically acceptable salt of a compound of formula (I) or a mixture containing two or more of these compounds or the salts thereof

(I)

wherein
A denotes

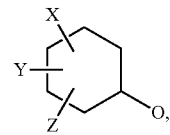

wherein X, Y and Z independently of one another denote hydrogen, C1-C4-alkyl or C2-C4-alkenyl, wherein optionally two of the radicals X, Y and Z are covalently bonded to one another under formation of a bicyclic ring system, in such a bicyclic ring system two of the radicals X, Y and Z together preferably form a radical having 1 to 4 carbon atoms, preferably a hydrocarbon radical having 1 to 3 carbon atoms, B denotes $NR^1R^2$, wherein $R^1$ denotes hydrogen or an organic radical having 1 to 14 carbon atoms, $R^2$ denotes an organic radical having 1 to 14 carbon atoms, and wherein optionally $R^1$ and $R^2$ are covalently bonded to one another, preferably so that B is a 3 to 8 membered ring.

The compounds of formula (I) thus are cyclohexyl carbamates (Carb-I)

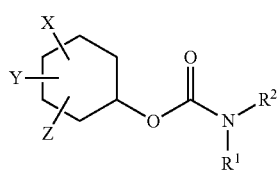
(Carb-I)

wherein $R^1$, $R^2$ and X, Y and Z have the meaning indicated hereinbefore or hereinafter.

As common in the art, in the context of the present invention, the substituents X, Y, and Z can in each case occupy—as indicated in the different structural formulae—any position in the cyclohexyl ring, i.e. in ipso, ortho, meta or para position to the cyclohexyl-carbon atom bonded to the oxygen of group A.

It is thus evident that two of the substituents X, Y, and Z—with exception of the ipsoposition—can be bonded to the same carbon atom of the cyclohexyl ring of group A.

The compounds of formula (I) show pronounced skin and/or hair lightening effects. The invention therefore relates to cosmetic or pharmaceutical preparations (compositions) containing a corresponding effective quantity of one or more compounds of formula (I), in particular for the topical lightening of skin and/or hair.

The compounds of formula (I) structurally belong to the group of cyclohexyl carbamates. Some of these compounds have been described in the prior art.

As common in the art, in the context of the present invention, abbreviations for certain chemical groups are used, for example Me=methyl, Et=ethyl, Pr=propyl, Bu=butyl, Ph=phenyl.

For the sake of clarity, it is emphasized that the present invention does not relate to substances as such or mixtures of substances as such which have been described or disclosed in the prior art.

The following compounds of formula (I) and more specifically of formula (Carb-II-R1H) as defined below, have been described in the literature.

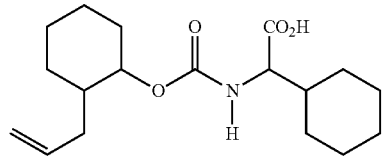

WO 2007/016441, WO 2008/051514 and WO 2008/051475 mention

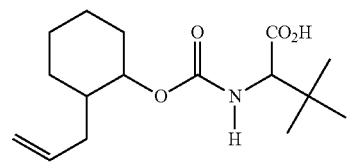

WO 2008/051514 discloses

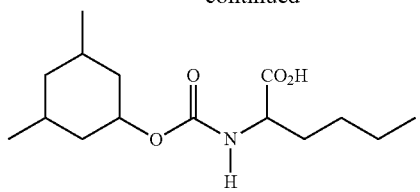

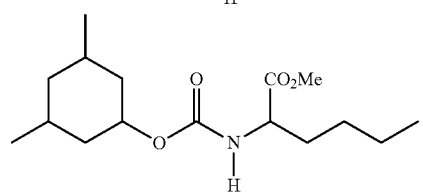

*Bioorganic & Medicinal Chemistry Letters* (2005), 15(9), 2209-2213 describes

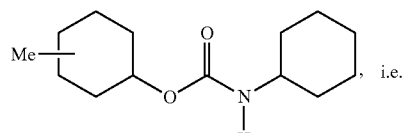, i.e.

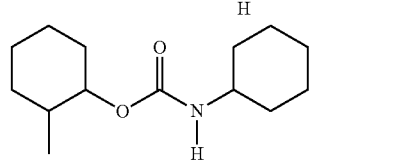

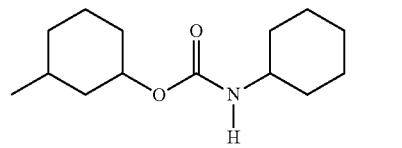

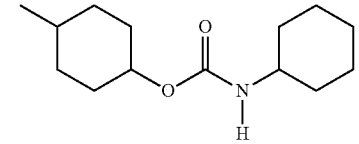

*Organic Preparations and Procedures International* (2004), 36(2), 141-149 discloses

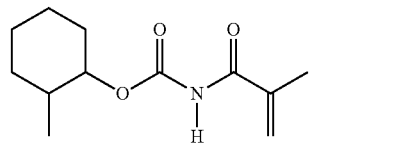

U.S. Pat. No. 5,892,100 mentions

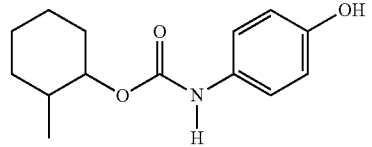

JP06-072036-A discloses

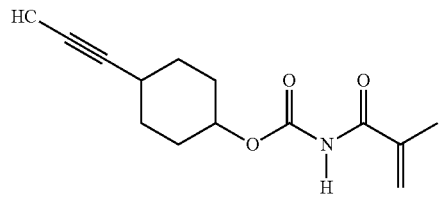

JP04-029964-A describes

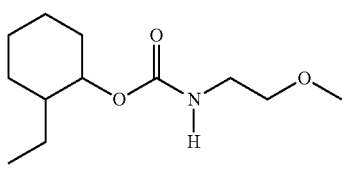

U.S. Pat. No. 5,260,474 mentions

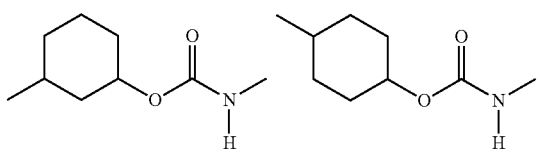

*Doklady - Akademiya Nauk Azerbaidzhanskoi SSR* (1980), 36(2), 63-66 describes

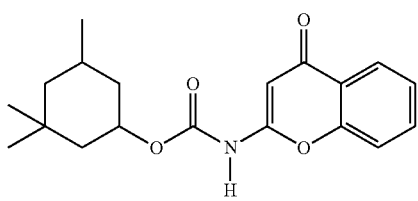

FR 2 259 589 mentions

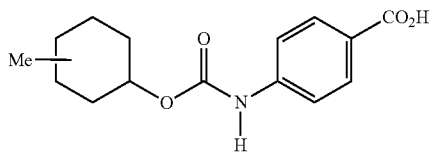

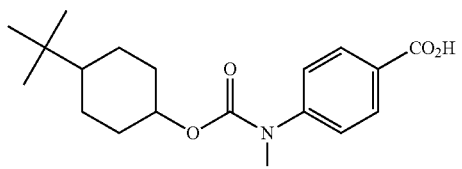

DE 20 500 87 discloses

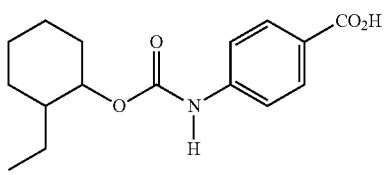

*Journal of Agricultural and Food Chemistry* (1967), 15(6), 1022-1029 describes

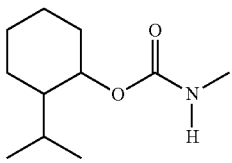

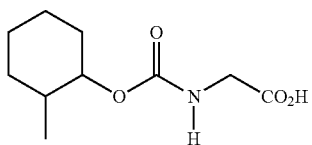

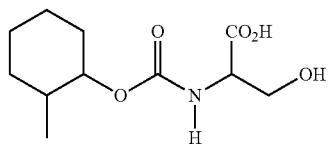

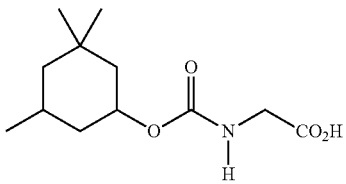

*Izvestiya Akademii Nauk SSSR, Seriya Khimicheskaya* (1966), (5), 922-924 discloses

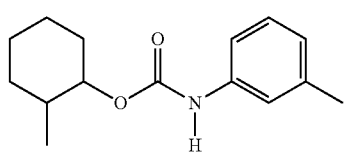

FR 1 401 219 mentions

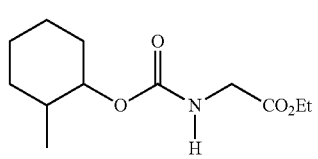

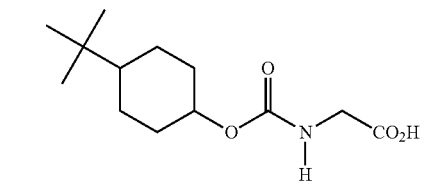

*Collection of Czechoslovak Chemical Communications* (1965), 30(2), 585-598 and 599-604 describe

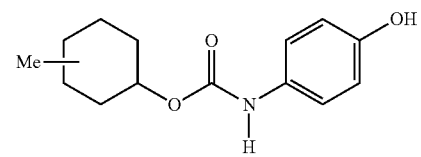

*Annales Pharmaceutiques Francaises* (1958), 16, 408-13 and *Journal of Organic Chemistry* (1958), 23, 1590-1591 disclose

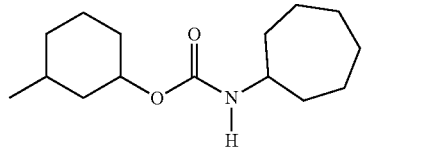

*Annales Pharmaceutiques Francaises* (1958), 16, 408-13 mentions

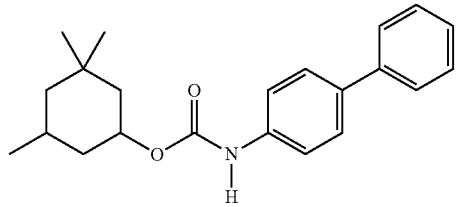

*Azarbaycan Neft Tasarrufati* (1933), (No. 3), 66-75 discloses

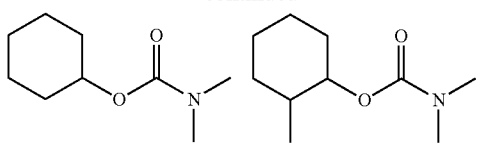

*J. Org. Chem.* 1981, 46, 2804-2806 discloses

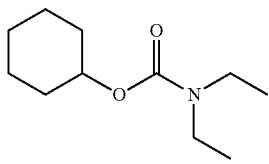

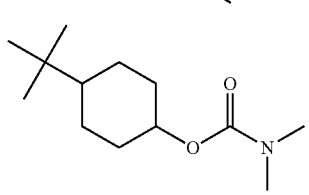

WO 2004/089880 discloses

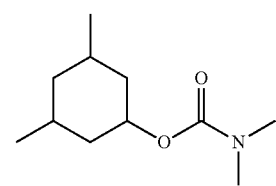

*Biochemical Pharmacology* 1961, 8, 179-191 describes

It is uncertain whether the following compound has been previously disclosed:

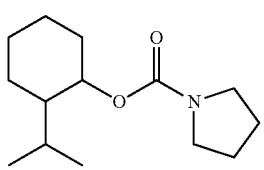 [SMILES: CC(C)C1CCCCC1OC(=O)N1CCCC1]

Thus, as a precautious measure, in a preferred embodiment the said compound as such is not considered to be in accordance with the present invention.

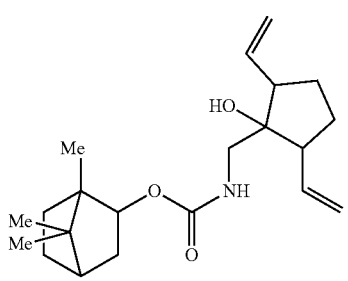

*Synthetic Communications* 2001, 31(24), 3759-3773 discloses

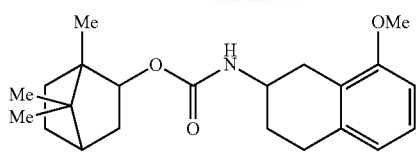

*Journal of Medicinal Chemistry* 1983, 26(9), 1215-18 discloses

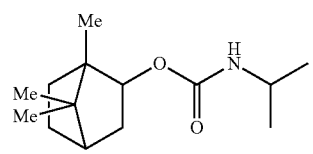

*Journal of Chromatography* 1982, 239, 227-31 discloses

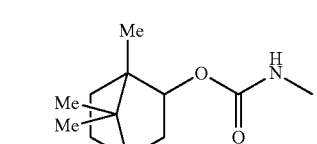

*Ecotoxicology and Environmental Safety* 2008, 71(3), 889-894 discloses

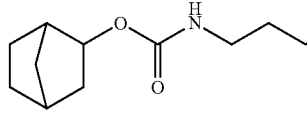

*Chirality* 2010, 22(2), 267-274 discloses

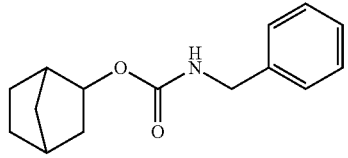

*Synthesis* 1989, (2), 131-132 discloses

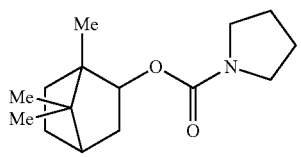

U.S. Pat. No. 3,480,663 describes

Various menthyl-carbamates of formula (M-X) and (M-H) have been described in the prior art

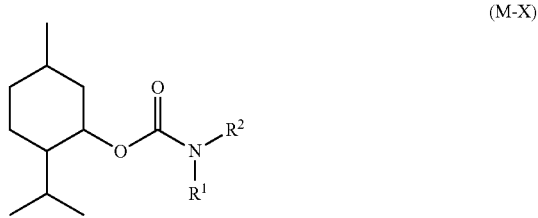

(M-X)

-continued

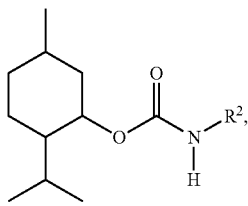

(M-H)

wherein $R^1$ and $R^2$ are within the definition of formula (I) as indicated hereinbefore or hereinafter and more specifically as defined for (Carb-II-R1H) given below.

Also, several compounds of formulae (I), (Carb-II) and (Carb-II-R1H) in which X, Y, and Z each denote H have been disclosed in the prior art.

Further, several compounds of formulae (I), (Carb-II) and of formula (Carb-II-R1H) as defined below wherein $R^2$ denotes phenyl or naphthyl have been described in the prior art.

Additionally, some bicyclic carbamates of formulae (Carb-II) and (Carb-II-R1H) as defined below wherein two of the radicals X, Y and Z are covalently bonded to one another under formation of a bicyclic ring system in which $R^2$ contains a —COOH and/or a =CH2 group have been described in the prior art.

WO 2004/033422 relates to compounds inhibiting fatty acid amide hydrolase (FAAH). Methods are described therein to control appetite and treat appetite disorders by administering FAAH inhibitors, thereby reducing body fat or body weight. The only specific compounds disclosed in WO 2004/033422 of relevance in the context of the present invention are the following:

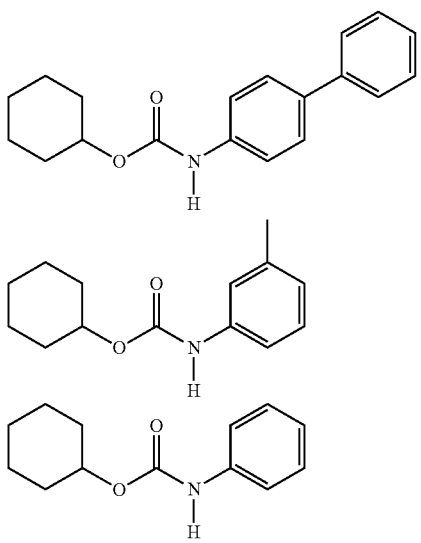

EP 1 284 145 describes the use of N-2-(3,4-dihydroxyphenyl)ethyl-substituted carbonic acid derivatives as radical scavengers and antioxidants. EP 1 284 145 further describes cosmetic preparations containing said carbonic acid derivatives. The effect of these compounds on the metabolism of fat cells or the body weight of humans was not investigated there. The only explicitly mentioned compound in EP 1 284 145 of relevance in view of formula (I) of the present invention is N-[2-(3,4-dihydroxyphenyl)ethyl-O-(1R,3R,4S)-menthyl] carbamate. According to EP 1 284 145, cosmetic or dermatologic preparations may additionally comprise skin lightening substances, by way of example kojic acid, hydroquinone or arbutin are mentioned.

In a preferred embodiment, a cosmetic or pharmaceutical preparation according to the present invention is free of N-[2-(3,4-dihydroxyphenyl)ethyl-O-(1R,3R,4S)menthyl]carbamate. In another preferred embodiment, compounds of formula (I) according to the present invention, more specifically compounds of formula (Carb-II-R1H), are excluded in which $R^2$ denotes a 2-(3,4-dihydroxyphenyl)ethyl—radical. In another preferred embodiment, cosmetic or pharmaceutical preparations according to the present invention are free of compounds of formula (I) according to the present invention, more specifically free of compounds of formula (Carb-II-R1H), in which $R^2$ denotes a 2-(3,4-dihydroxyphenyl) ethyl—radical.

WO 01/98235 describes the use of N-3,4-dihydroxybenzyl-substituted carbonic acid derivatives as radical scavengers and antioxidants. WO 01/98235 further describes cosmetic preparations containing said carbonic acid derivatives. The effect of these compounds on the metabolism of fat cells or the body weight of humans was not investigated there. The only explicitly mentioned compound in WO 01/98235 of relevance in view of formula (I) of the present invention is N-(3,4-dihydroxybenzyl)-O-(1R,3R,4S)-menthyl]carbamate. According to WO 01/98235, cosmetic or dermatologic preparations may additionally comprise skin lightening substances, by way of example kojic acid, hydroquinone or arbutin are mentioned.

In a preferred embodiment, a cosmetic or pharmaceutical preparation according to the present invention is free of N-(3, 4-dihydroxybenzyl)-O-(1R,3R,4S)-menthyl]carbamate. In another preferred embodiment, compounds of formula (I) according to the present invention, more specifically compounds of formula (Carb-II-R1H), are excluded in which $R^2$ denotes a 3,4-dihydroxybenzyl—radical. In another preferred embodiment, cosmetic or pharmaceutical preparations according to the present invention are free of compounds of formula (I) according to the present invention, more specifically free of compounds of formula (Carb-II-R1H), in which $R^2$ denotes a 3,4-dihydroxybenzyl—radical.

In a preferred embodiment, compounds of formula (I) according to the present invention, more specifically compounds of formula (Carb-II-R1H), are excluded in which $R^2$ denotes a radical containing a 3,4-dihydroxyphenyl—group. In another preferred embodiment, cosmetic or pharmaceutical preparations according to the present invention are free of compounds of formula (I) according to the present invention, more specifically free of compounds of formula (Carb-II-R1H), in which $R^2$ denotes a radical containing a 3,4-dihydroxyphenyl—group.

In another preferred embodiment, compounds of formula (I) according to the present invention, more specifically compounds of formula (Carb-II-R1H), are excluded in which $R^2$ denotes a radical containing a dihydroxyphenyl—group. In another preferred embodiment, cosmetic or pharmaceutical preparations according to the present invention are free of compounds of formula (I) according to the present invention, more specifically free of compounds of formula (Carb-II-R1H), in which $R^2$ denotes a radical containing a dihydroxyphenyl—group.

There is no indication hitherto that the compounds used in accordance with the present invention are suitable for cosmetic or therapeutic lightening of skin and/or hair.

In the context of the present invention, a cosmetic use or a cosmetic method is free of any therapeutic (side) effects.

In the context of the present invention, a therapeutic or pharmaceutical use or method is considered as medical treatment, optionally with cosmetic (side) effects.

The compounds according to the invention of formula (I), depending on the meaning of X, Y, Z, $R^1$ and $R^2$, may exist in different stereoisomeric forms and may be used in the context of the present invention as stereoisomers, enantiomers, diastereomers, syn-/antiisomers, endo-/exo-isomers, cis-/trans-isomers or epimers. The compounds of formula (I) can be used in the context of the present invention in the form of the pure cis- or trans-, syn- or anti-diastereomer or in the form of any mixture of diastereomers. The compounds of formula (I) can also be used in the context of the present invention in the form of the pure enantiomers or in the form of any mixture of enantiomers, in the latter case racemates being preferred.

In case $R^1$ does not denote hydrogen, $R^1$ and $R^2$ independently of one another preferably denote an optionally substituted radical selected from the group consisting of alkyl, heteroalkyl, cycloalkyl, cycloalkylalkyl, alkenyl, cycloalkenyl, cycloalkenylalkyl, alkynyl, cycloalkylalkynyl, aryl, heteroaryl, arylalkyl, cycloalkylaryl, cycloalkenylaryl, cycloalkylheteroaryl, heterocycloalkylaryl, heterocycloalkenylaryl, heterocycloalkenylheteroaryl and heteroarylalkyl.

In case $R^1$ does not denote hydrogen, $R^1$ and $R^2$ independently of one another more preferably denote an optionally substituted radical $C_1$-$C_{14}$-alkyl, $C_1$-$C_{14}$-heteroalkyl, $C_3$-$C_{14}$-cycloalkyl, $C_4$-$C_{14}$-cycloalkylalkyl, $C_2$-$C_{14}$-alkenyl, $C_3$-$C_{14}$-cycloalkenyl, $C_4$-$C_{14}$-cycloalkenylalkyl, $C_2$-$C_{14}$-alkynyl, $C_5$-$C_{14}$-cycloalkylalkynyl, $C_3$-$C_{14}$-aryl, $C_2$-$C_{14}$-heteroaryl, $C_4$-$C_{14}$-arylalkyl, $C_8$-$C_{14}$-cycloalkylaryl, $C_8$-$C_{14}$-cycloalkenylaryl, $C_5$-$C_{14}$-cycloalkylheteroaryl, $C_8$-$C_{14}$-heterocycloalkylaryl, $C_8$-$C_{14}$-heterocycloalkenylaryl, $C_8$-$C_{14}$-heterocycloalkenylheteroaryl and $C_3$-$C_{14}$-heteroarylalkyl.

Heteroalkyl, heteroaryl, cycloalkylheteroaryl, heterocycloalkylaryl, heterocycloalkenylaryl, heterocycloalkenylheteroaryl and heteroarylalkyl radicals in the context of the present invention preferably contain at least one heteroatom, optionally up to four heteroatoms, selected independently from the group consisting of O, S and/or N. Preferred are heteroalkyl, heteroaryl, cycloalkylheteroaryl, heterocycloalkylaryl, heterocycloalkenylaryl, heterocycloalkenylheteroaryl and heteroarylalkyl radicals containing one, two or three heteroatoms, selected independently from the group consisting of O, S and/or N.

Preferably, substituents X, Y, and Z in each case occupy any desired position in the cyclohexyl ring in ortho, meta or para position to the cyclohexyl-carbon atom bonded to the oxygen of the carbamate group. Thus, preferably A denotes

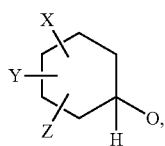

wherein X, Y and Z have the meaning indicated hereinbefore or hereinafter.

The corresponding preferred compounds of formula (I) are cyclohexyl carbamates of formula (Carb-II):

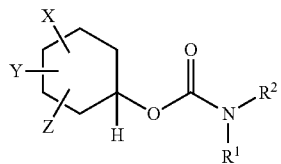

(Carb-II)

wherein $R^1$, $R^2$ and X, Y and Z have the meaning indicated hereinbefore or hereinafter.

Substituents X, Y and Z independently of one another preferably denote hydrogen, methyl, ethyl, n-propyl, isopropyl, n-butyl, sec.-butyl, isobutyl, tert.-butyl, ethenyl, prop-2-en-1-yl, prop-1-en-1-yl, prop-1-en-2-yl, but-1-en-1-yl, but-1-en-2-yl, but-1-en-3-yl, but-2-en-1-yl, but-3-en-1-yl, but-2-en-2-yl, 2-methylprop-1-en-1-yl, 2-methylprop-2-en-1-yl.

In a preferred embodiment, substituents X, Y and Z independently of one another denote hydrogen or C1-C4-alkyl. In another preferred embodiment, at least one of the substituents X, Y and Z denotes C1-C4-alkyl, i.e. at least one of the substituents X, Y and Z does not denote hydrogen.

In another preferred embodiment, two of the substituents X, Y and Z independently of one another denote hydrogen or C1-C4-alkyl and at least one of the substituents X, Y and Z denotes C1-C4-alkyl.

In one embodiment, in preferred compounds of formulae (I), (Carb-I) and (Carb-II) $R^1$ denotes hydrogen. In our investigations, these compounds were generally found to have good to excellent activity and efficacy regarding skin and/or lightening.

Thus, in one embodiment, more preferred compounds of formula (I) are cyclohexyl carbamates of formula (Carb-II-R1H):

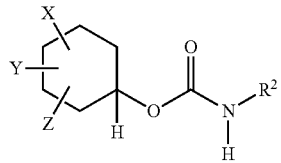

(Carb-II-R1H)

wherein X, Y and Z have the meaning indicated hereinbefore or hereinafter.

In preferred compounds of formulae (I), (Carb-I), (Carb-II) and (Carb-II-R1H) (as defined below), $R^2$ denotes an organic radical having 1 to 12 carbon atoms, preferably an organic radical having 1 to 10 carbon atoms, more preferably an organic radical having 1 to 8 carbon atoms.

In more preferred compounds of formulae (I), (Carb-I), (Carb-II) and (Carb-II-R1H), $R^2$ denotes an optionally substituted radical $C_1$-$C_{10}$-alkyl, $C_1$-$C_{10}$-heteroalkyl, $C_3$-$C_{10}$-cycloalkyl, $C_4$-$C_{10}$-cycloalkylalkyl, $C_2$-$C_{10}$-alkenyl, $C_3$-$C_{10}$-cycloalkenyl, $C_4$-$C_{10}$-cycloalkenylalkyl, $C_2$-$C_{10}$-alkynyl, $C_5$-$C_{10}$-cycloalkylalkynyl, $C_3$-$C_{10}$-aryl, $C_2$-$C_{10}$-heteroaryl, $C_4$-$C_{10}$-arylalkyl, $C_8$-$C_{10}$-cycloalkylaryl, $C_8$-$C_{10}$-cycloalkenylaryl, $C_5$-$C_{10}$-cycloalkylheteroaryl, $C_8$-$C_{10}$-heterocycloalkylaryl, $C_8$-$C_{10}$-heterocycloalkenylaryl, $C_8$-$C_{10}$-heterocycloalkenylheteroaryl and $C_3$-$C_{10}$-heteroarylalkyl.

In most preferred compounds of formulae (I), (Carb-I), (Carb-II) and (Carb-II-R1H), $R^2$ denotes an optionally substituted radical chosen from the group consisting of $C_1$-$C_8$-alkyl, $C_3$-$C_8$-cycloalkyl, $C_4$-$C_{12}$-cycloalkylalkyl, $C_2$-$C_8$-alkenyl, $C_3$-$C_8$-cycloalkenyl, $C_4$-$C_8$-cycloalkenylalkyl, $C_3$-$C_8$- aryl, $C_2$-$C_8$-heteroaryl, $C_4$-$C_8$-arylalkyl, $C_5$-$C_8$-cycloalkylheteroaryl and $C_4$-$C_8$-heteroarylalkyl.

If the radicals $R^1$ and/or $R^2$ are substituted, $R^1$ and/or $R^2$ each may contain one or more heteroatoms, preferably independently selected from the group consisting of O, S, N, Si and F. If the heteroatoms are selected from the group consisting of O, S and N, the radicals $R^1$ and/or $R^2$ each preferably contain one, two or three heteroatoms selected independently from the group consisting of O, S and/or N.

If the radicals $R^1$ and/or $R^2$ are substituted the following substituents are preferred:
hydroxyl,
fluoride,
$C_1$-$C_8$-alkyl, preferably methyl, ethyl, n-propyl, iso-propyl, n-butyl, iso-butyl, tert-butyl,
$C_3$-$C_{12}$-cycloalkyl, preferably cyclopropyl, cyclopentyl, cyclohexyl, cyclooctyl, cyclododecyl,
$C_2$-$C_8$-alkynyl, preferably ethynyl, propynyl,
$C_1$-$C_8$-perfluoroalkyl, preferably trifluoromethyl, nonafluorobutyl,
$C_1$-$C_8$-alkoxy, preferably methoxy, ethoxy, n-propoxy, iso-propoxy, n-butoxy, iso-butoxy, tert-butoxy,
$C_3$-$C_8$-cycloalkoxy, preferably $C_3$-cycloalkoxy, $C_5$-cycloalkoxy, $C_6$-cycloalkoxy, $C_8$-cycloalkoxy,
$C_1$-$C_{10}$-alkoxyalkyl, in which 1 to 3 $CH_2$ groups are replaced by oxygen, preferably —[—O—$CH_2$—$CH_2$—]$_v$-Q or —[—O—$CH_2$—CHMe-]$_v$-Q, wherein Q is OH or $CH_3$ and wherein v denotes an integer from 1 to 3,
$C_1$-$C_4$-acyl, preferably acetyl,
$C_1$-$C_4$-acetal, preferably dimethylacetal, diethylacetal or a methylenedioxy group —O—$CH_2$—O—.
$C_1$-$C_4$-carboxyl, preferably $CO_2Me$, $CO_2Et$, $CO_2$ iso-Pr, $CO_2$tert-Bu,
$C_1$-$C_4$-acyloxy, preferably acetyloxy,
$Si_1$—$Si_{10}$-silyl, and
$Si_1$—$Si_{30}$-siloxy or polysiloxy.

Preferred cosmetically or pharmaceutically acceptable salts of compounds of formula (I) are those in which the one or more counterions (counteracting cation) is selected from the group consisting of $Na^+$, $K^+$, $NH_4^+$, trialkylammonium $NHR^i{}_3^+$, $Ca^{2+}$, $Mg^{2+}$, $Zn^{2+}$ and $Al^{3+}$.

In trialkylammonium $NHR^i{}_3^+$, preferably each $R^i$ independently of the other radicals $R^i$ denotes an alkyl group having 1 to 30 C-atoms, preferably having 4 to 22 C-atoms.

Particular preferred counterions are $Na^+$, $K^+$, $NH_4^+$, $Ca^{2+}$ and/or $Mg^{2+}$.

In case two different compounds of formula (I) are used as a mixture, generally the ratio by weight of the two compounds is chosen in the range of from 10:1 to 1:10, preferably in the range of from 5:1 to 1:5, more preferably in the range of from 3:1 to 1:3, the counterion, if present, not being included in the case of salts.

In the context of the present invention, a wavy line in structural formulae means that the double bond can be in the (E) or (Z) configuration.

Preferred compounds of formulae (I), (Carb-I), (Carb-II) and (Carb-II-R1H) are those in which A denotes a radical chosen from the following list "CyO":

AA

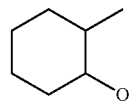
AB

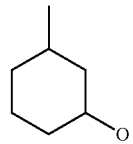
AC

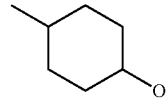
AD

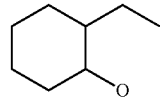
AE

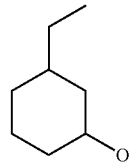
AF

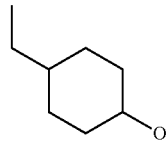
AG

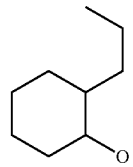
AH

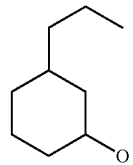
AI

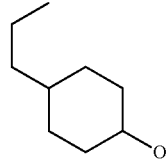
AJ

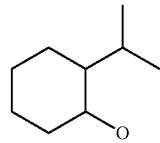
AK

-continued
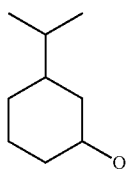
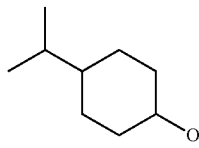
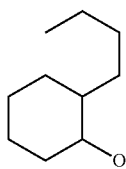
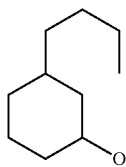
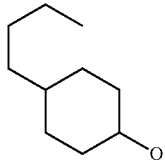
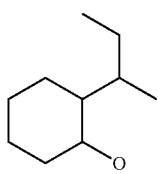
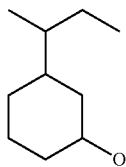
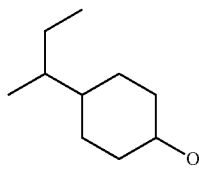
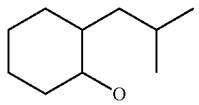
-continued
AL
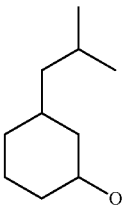
AM
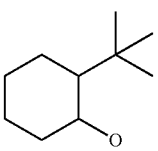
AN
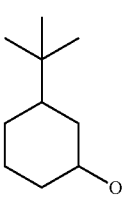
AO
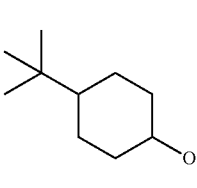
AP
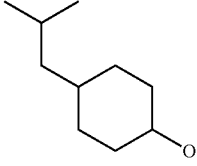
AQ
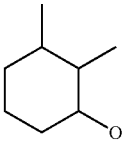
AR
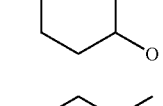
AS
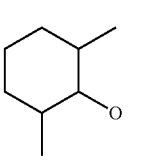
AT
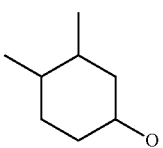
AU
AV
AW
AX
AY
AZ
BA
BB
BC
BD

| | | |
|---|---|---|
| | BE | BO |
| | BF | BP |
| | BG | BQ |
| | BH | BR |
| | | BS |
| | BI | |
| | BJ | BT |
| | BK | BU |
| | BL | BV |
| | BM | BW |
| | BN | BX |

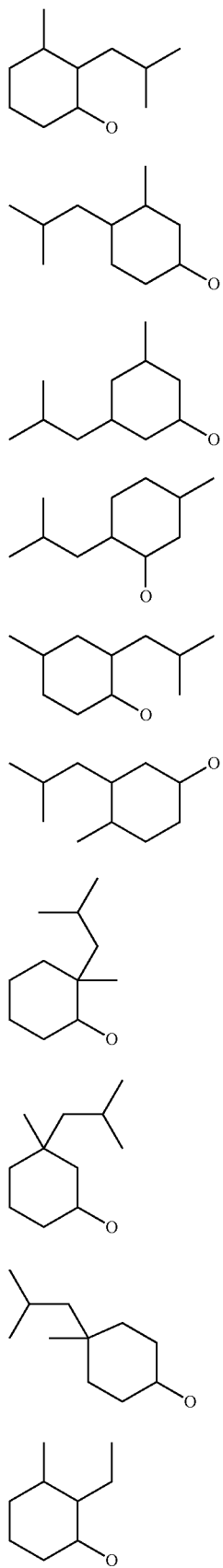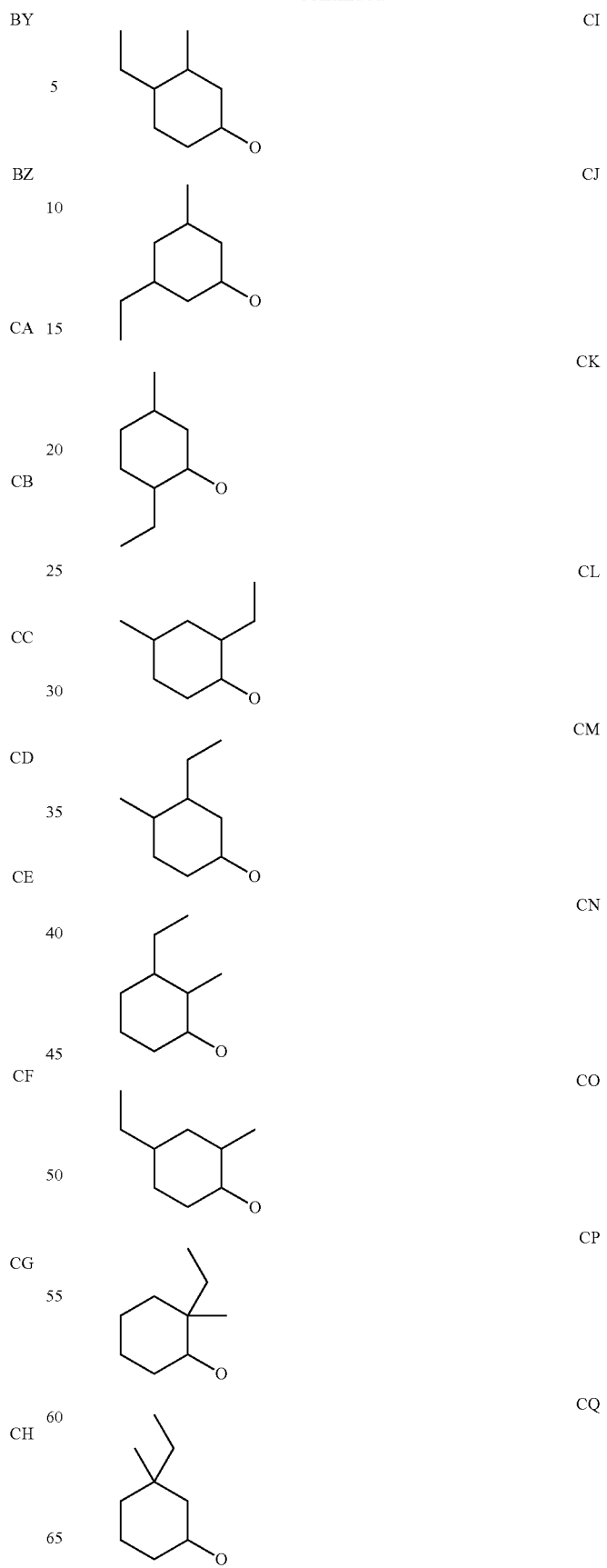

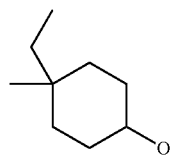
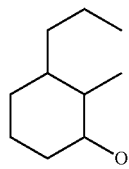
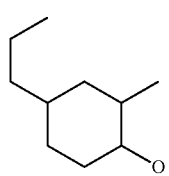
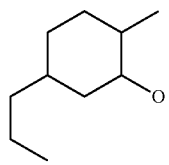
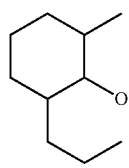
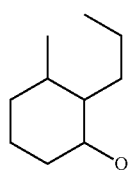
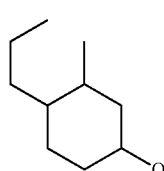
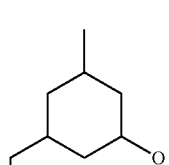
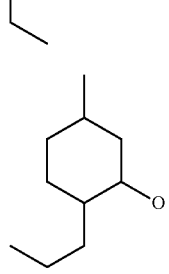
CR 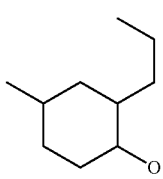
CS 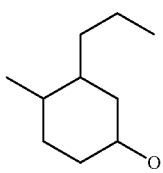
CT 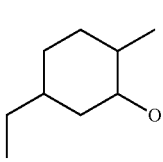
CU 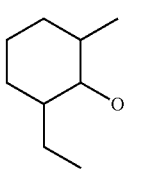
CV 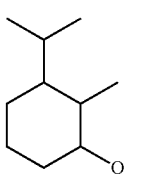
CW 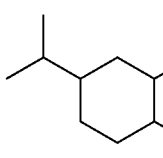
CX 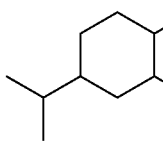
CY 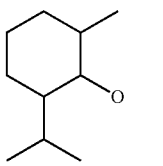
CZ 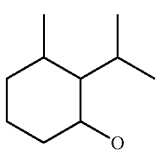
DA
DB
DC
DD
DE
DF
DG
DH
DI

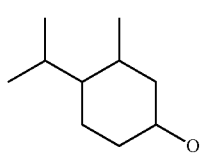
DJ
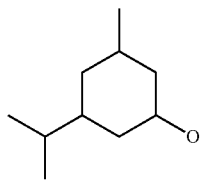
DK
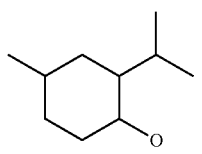
DL
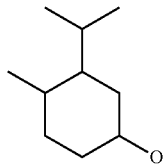
DM
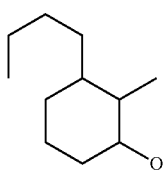
DN
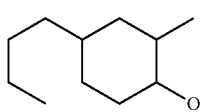
DO
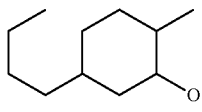
DP
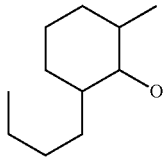
DQ
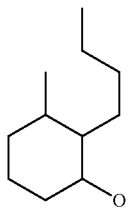
DR
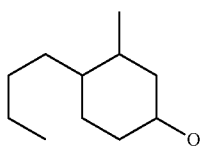
DS
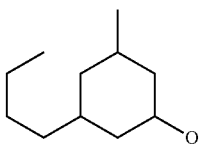
DT
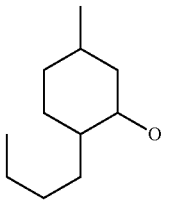
DU
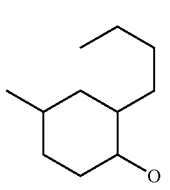
DV
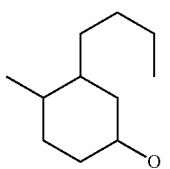
DW
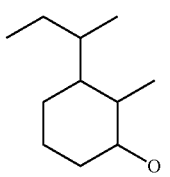
DX
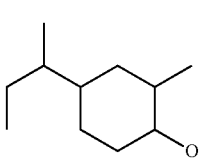
DY
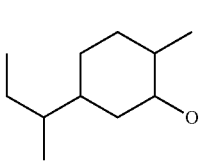
DZ
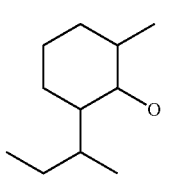
EA
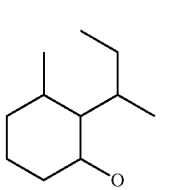
EB

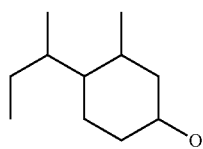
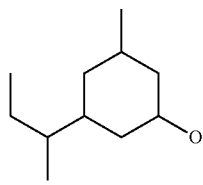
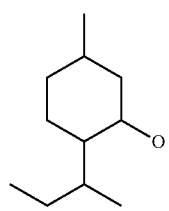
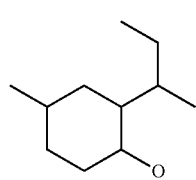
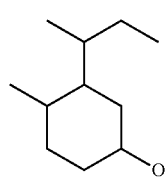
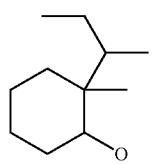
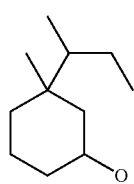
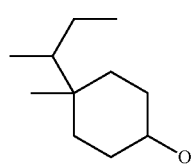
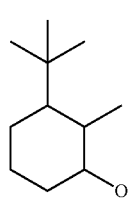
EC
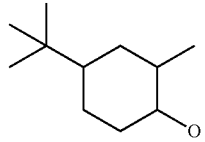
ED
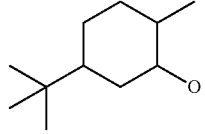
EE
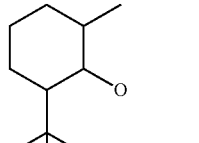
EF
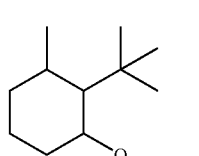
EG
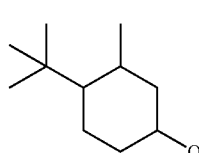
EH
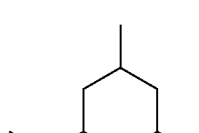
EI
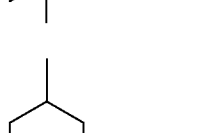
EJ
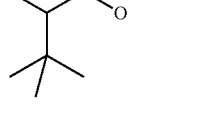
EK
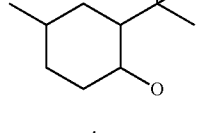
EL
EM
EN
EO
EP
EQ
ER
ES
ET

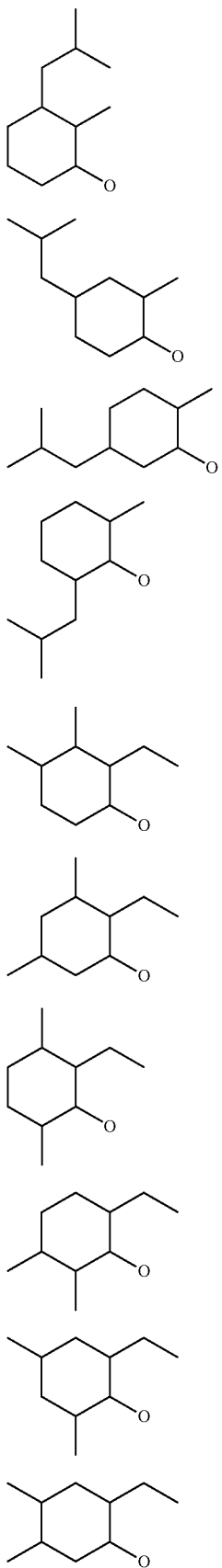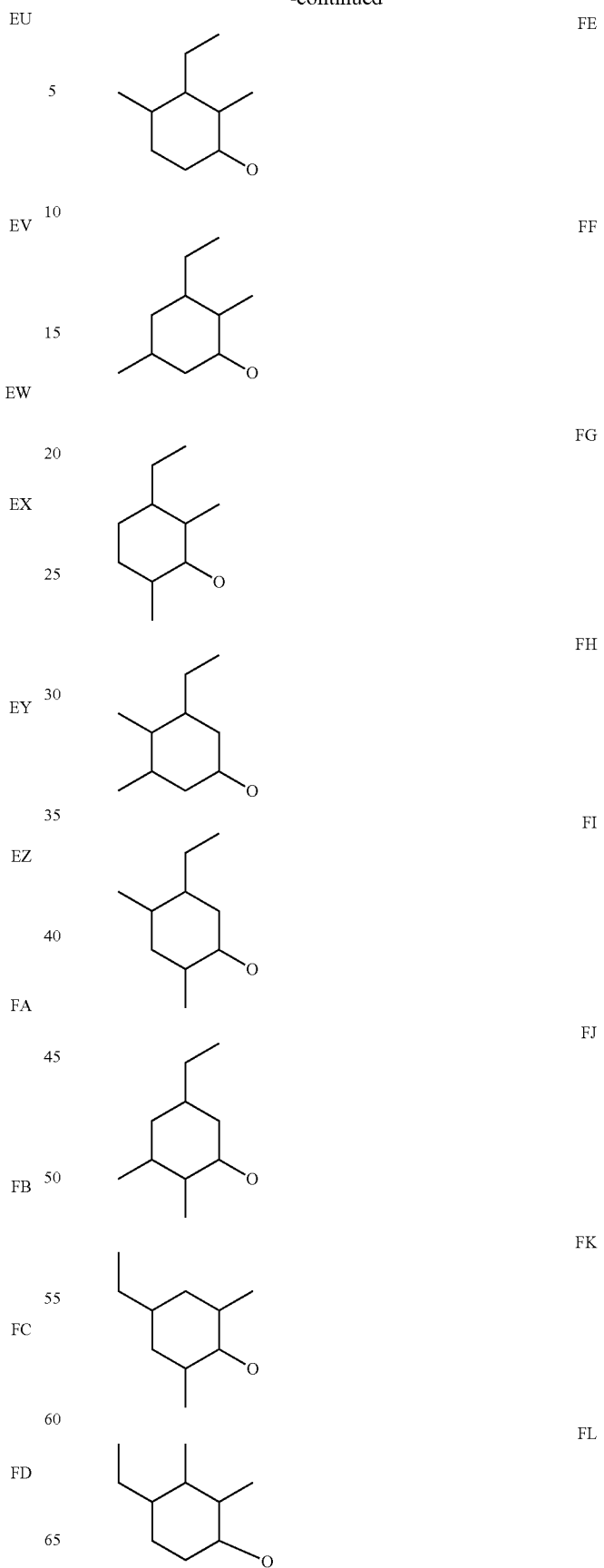

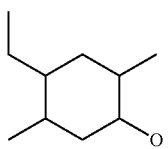
FM
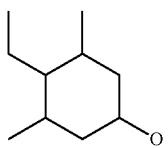
FN
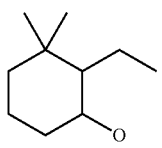
FO
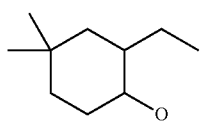
FP
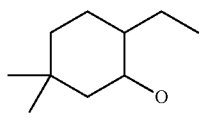
FQ
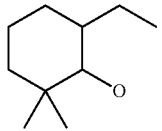
FR
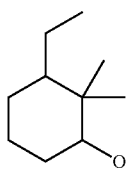
FS
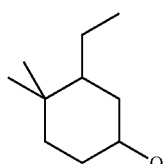
FT
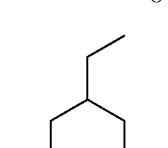
FU
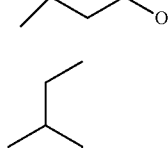
FV
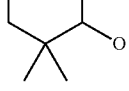
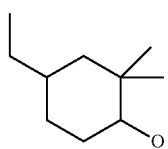
FW
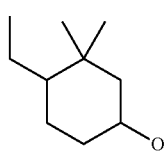
FX
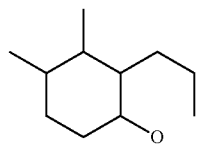
FY
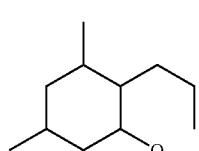
FZ
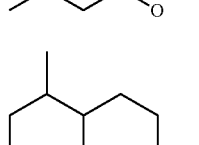
GA
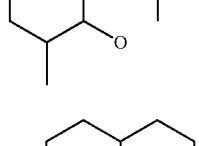
GB
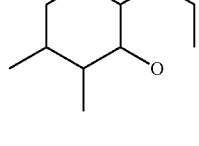
GC
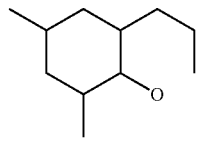
GD
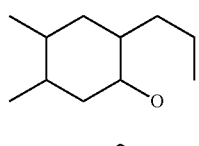
GE
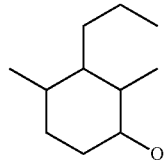
GF
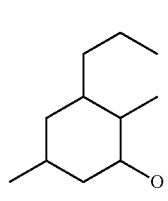

-continued

| Label | Label |
|---|---|
| GG | GO |
| GH | GP |
| GI | GQ |
| GJ | GR |
| GK | GS |
| GL | GT |
| GM | GU |
| GN | GV |
|  | GW |

| | | |
|---|---|---|
| | 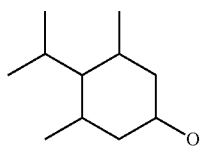 | |
| | 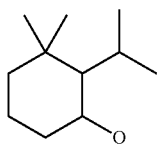 | |
| | 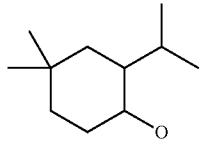 | |
| | 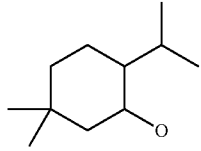 | |
| | 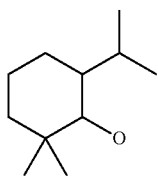 | |
| | 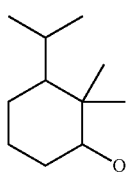 | |
| | 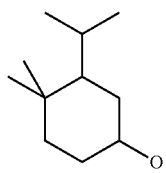 | |
| | 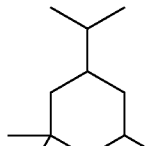 | |
| | 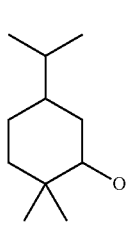 | |
| | | |
|---|---|---|
| GX | 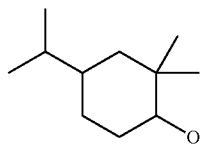 | HG |
| GY | 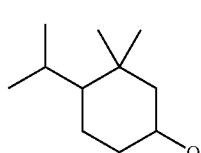 | HH |
| GZ | 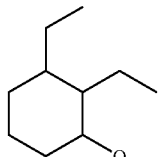 | HI |
| HA | 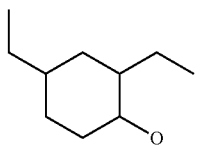 | HJ |
| HB | 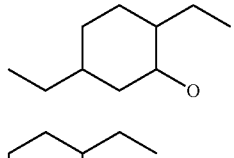 | HK |
| HC | 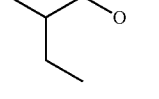 | HL |
| HD | 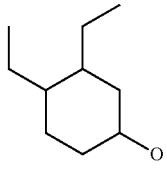 | HM |
| HE | | HN |
| HF | 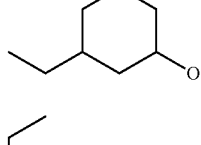 | HO |
| | 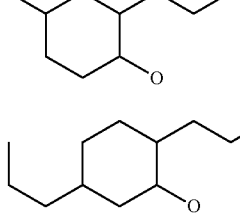 | HP |

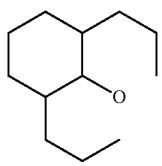 HQ
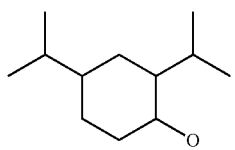 HR
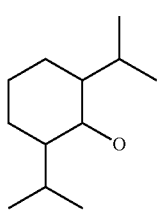 HS
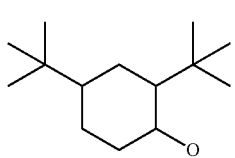 HT
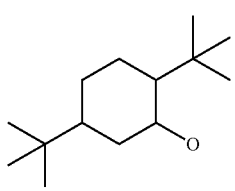 HU
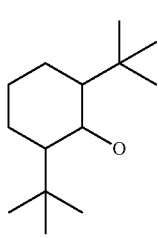 HV
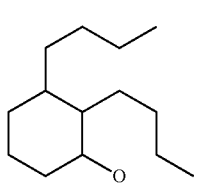 HW
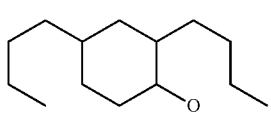 HX
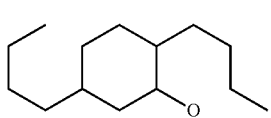 HY IJ
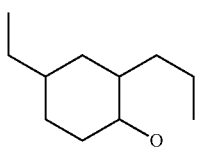
IK
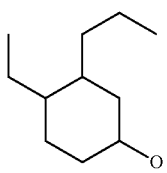
IL
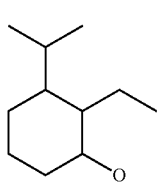
IM
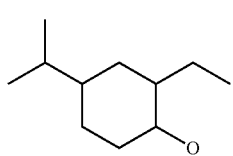
IN
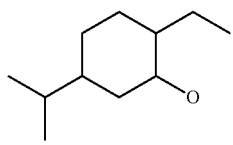
IO
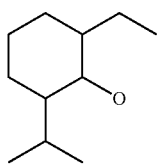
IP
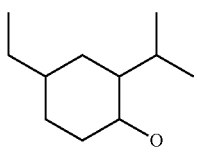
IQ
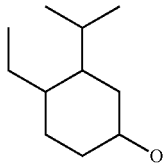
IR
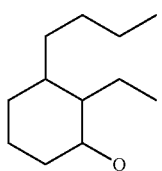
IS
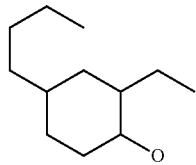
IT
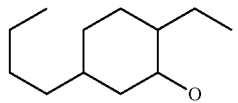
IU
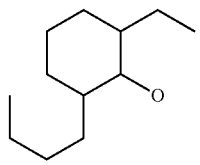
IV
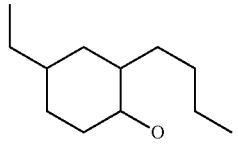
IW
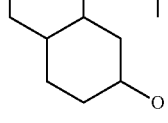
IX
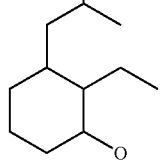
IY
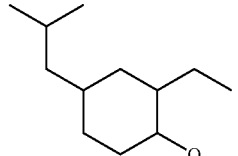
IZ
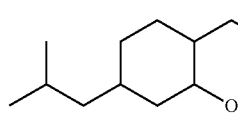
JA
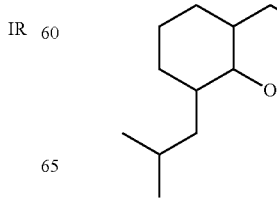

39
-continued
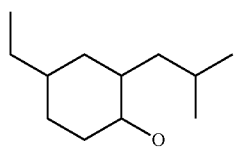
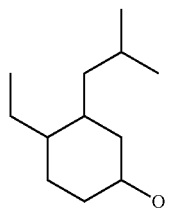
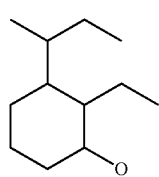
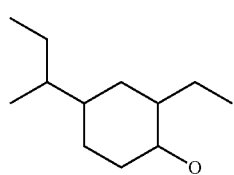
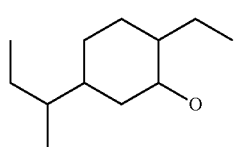
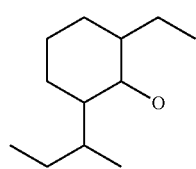
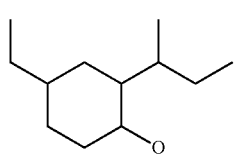
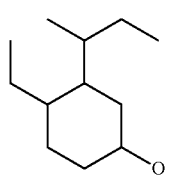
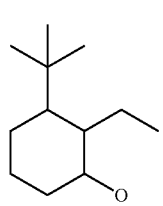
40
-continued
JB
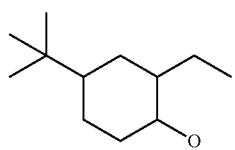
JC
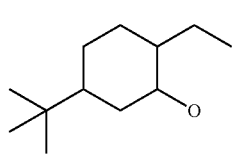
JD
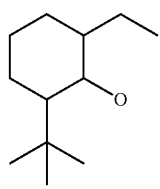
JE
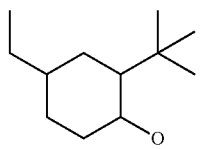
JF
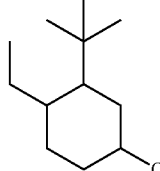
JG
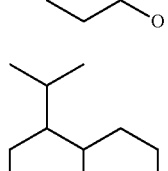
JH
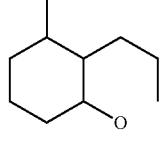
JI
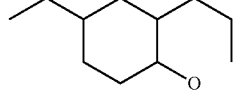
JJ
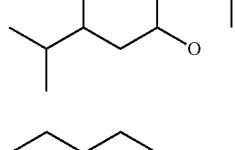
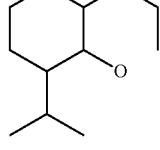
JK
JL
JM
JN
JO
JP
JQ
JR
JS 41
-continued
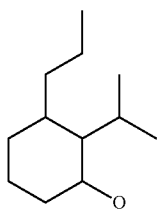
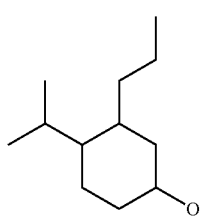
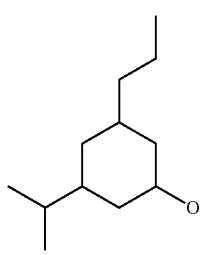
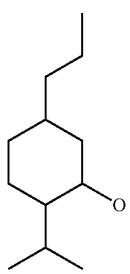
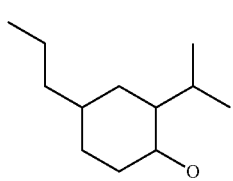
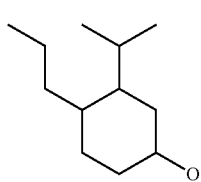
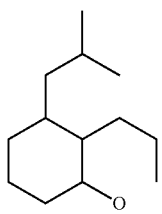
42
-continued
JT
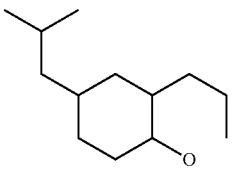
JU
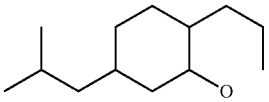
JV
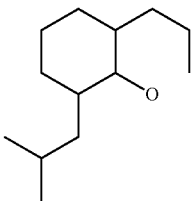
JW
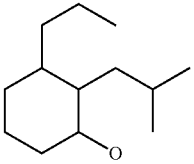
JX
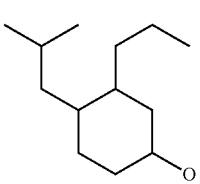
JY
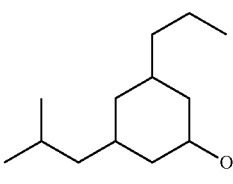
JZ
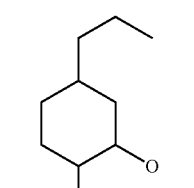
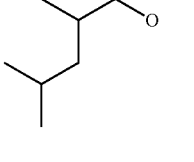
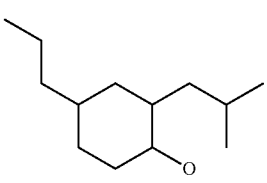
KA
KB
KC
KD
KE
KF
KG
KH KI
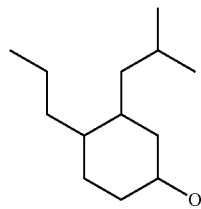
KJ
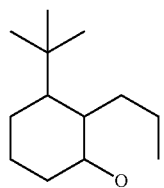
KK
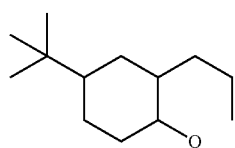
KL
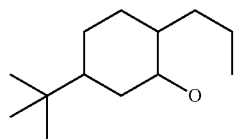
KM
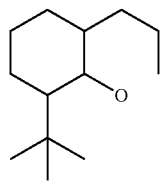
KN
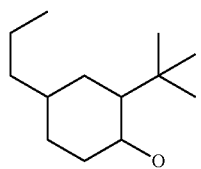
KO
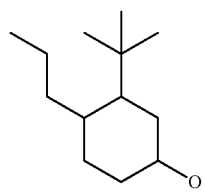
KP
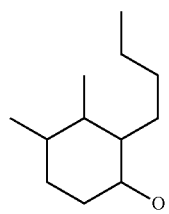
KQ
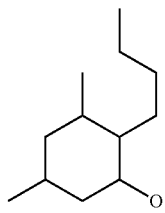
KR
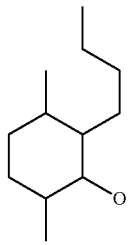
KS
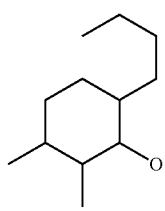
KT
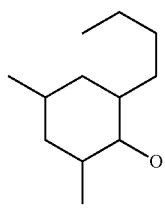
KU
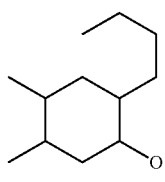
KV
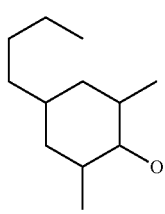
KW
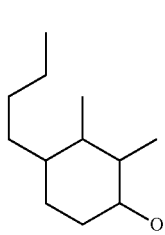

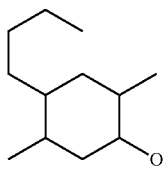
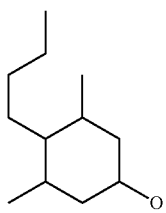
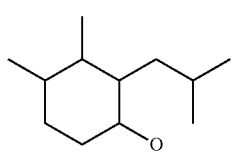
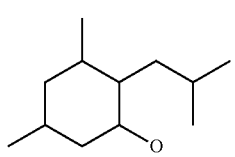
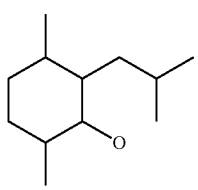
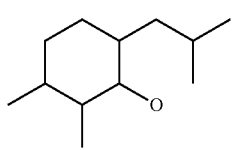
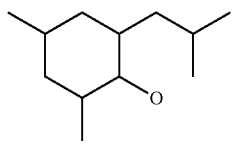
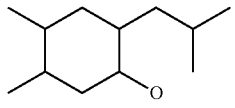
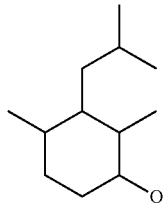
KX
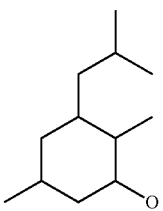
KY
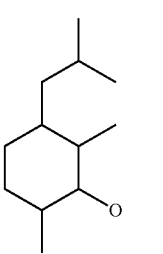
KZ
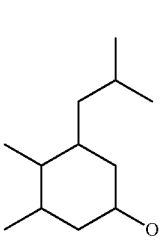
LA
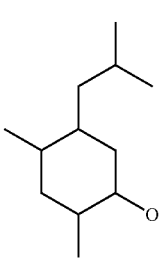
LB
LC
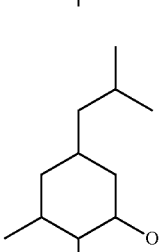
LD
LE
LF
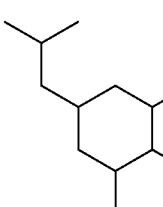
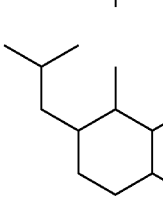
LG
LH
LI
LJ
LK
LL
LM

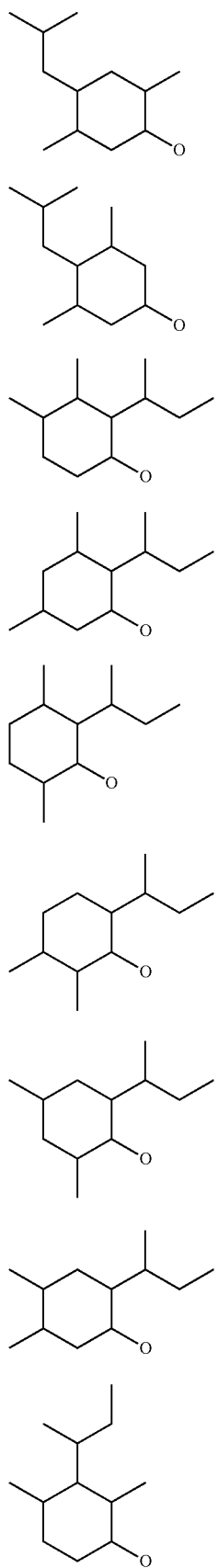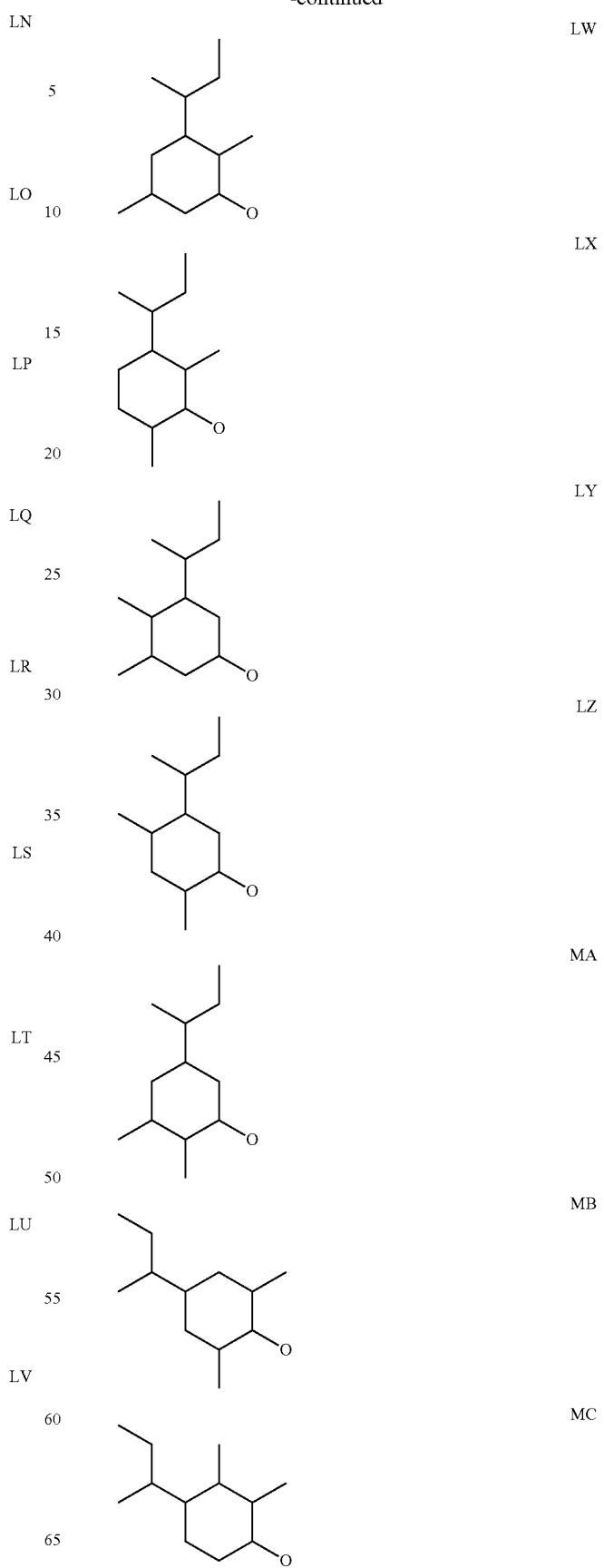

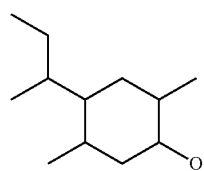 MD
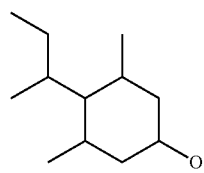 ME
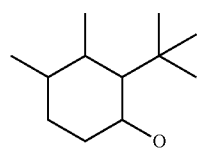 MF
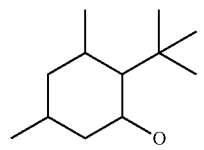 MG
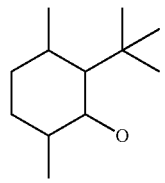 MH
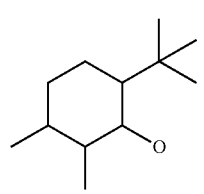 MI
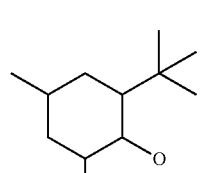 MJ
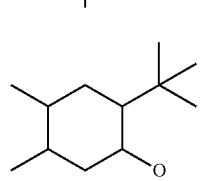 MK
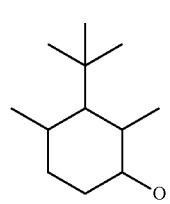 ML
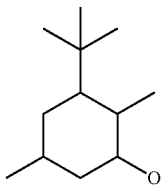 MM
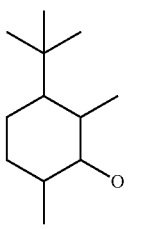 MN
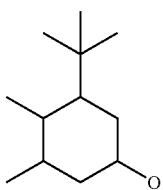 MO
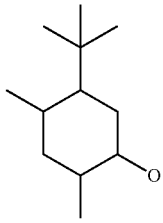 MP
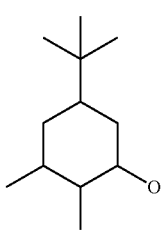 MQ
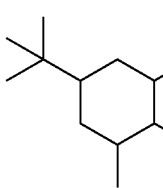 MR
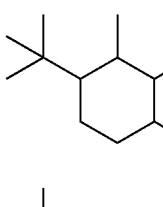 MS
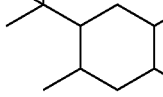 MT

| | |
|---|---|
| | 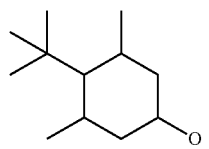 |
| | 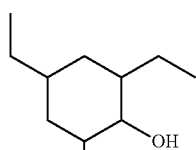 |
| | 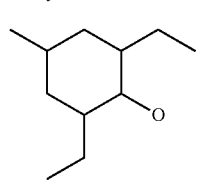 |
| | 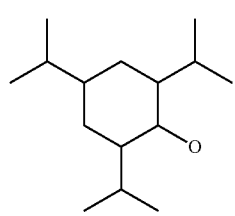 |
| | 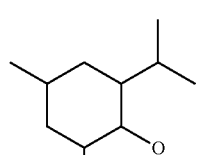 |
| | 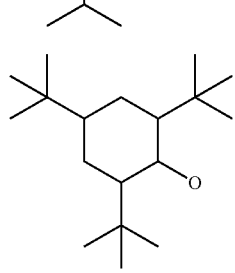 |
| | 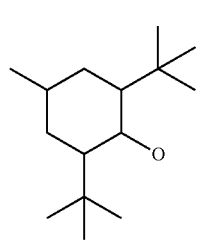 |
| | 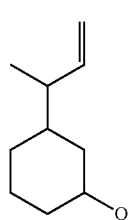 |
| | |
|---|---|
| MU | 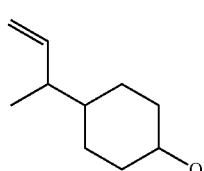 |
| MV | 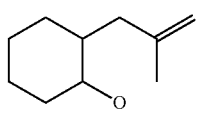 |
| MW | 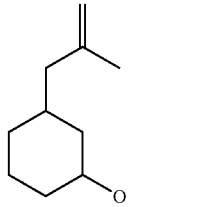 |
| MX | 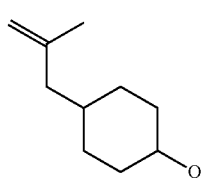 |
| MY | 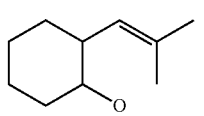 |
| MZ | 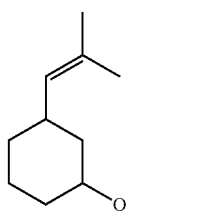 |
| NA | 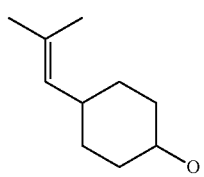 |
| NR | 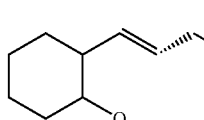 |
| | 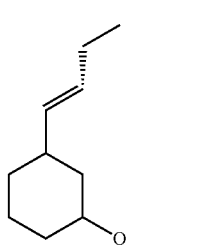 |
NS
NT
NU
NV
NW
NX
NY
NZ
OA

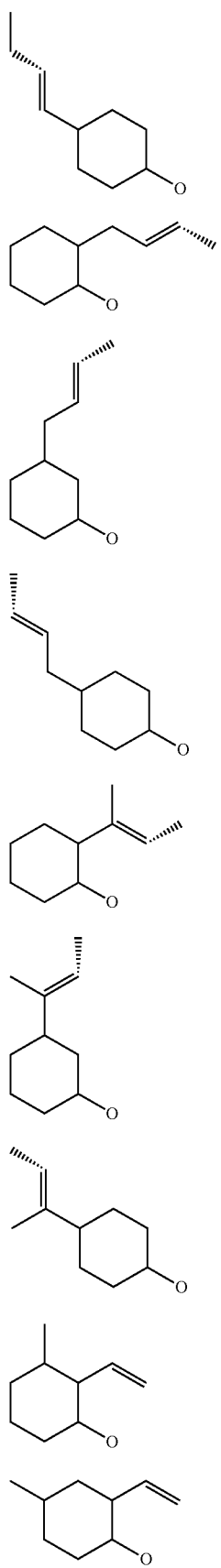
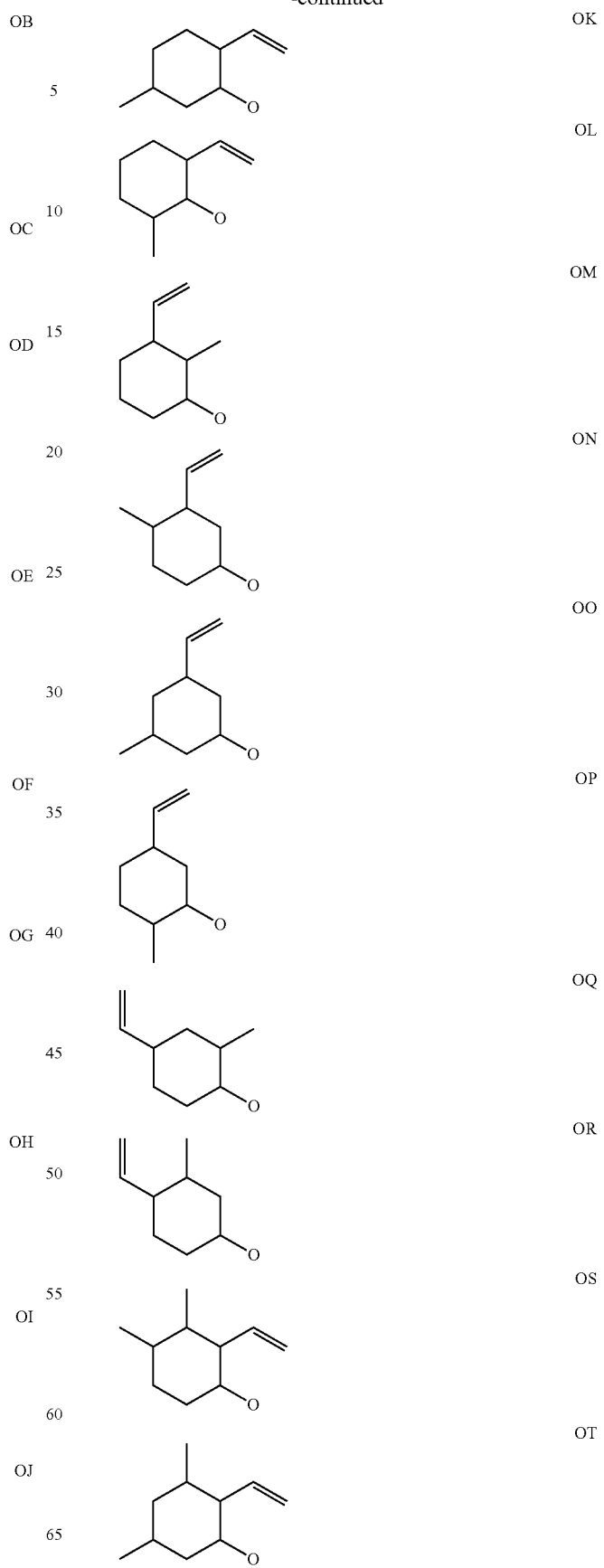

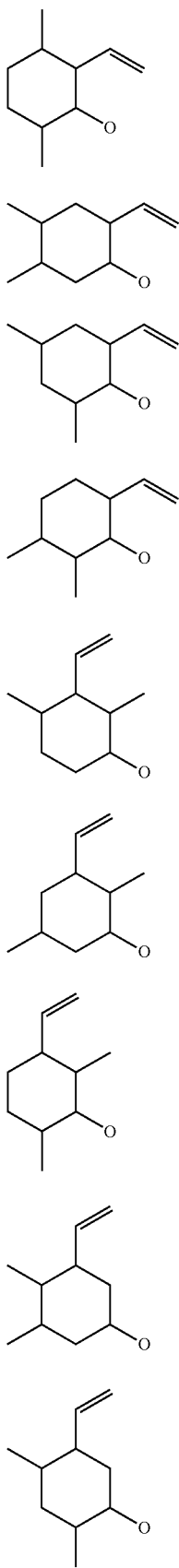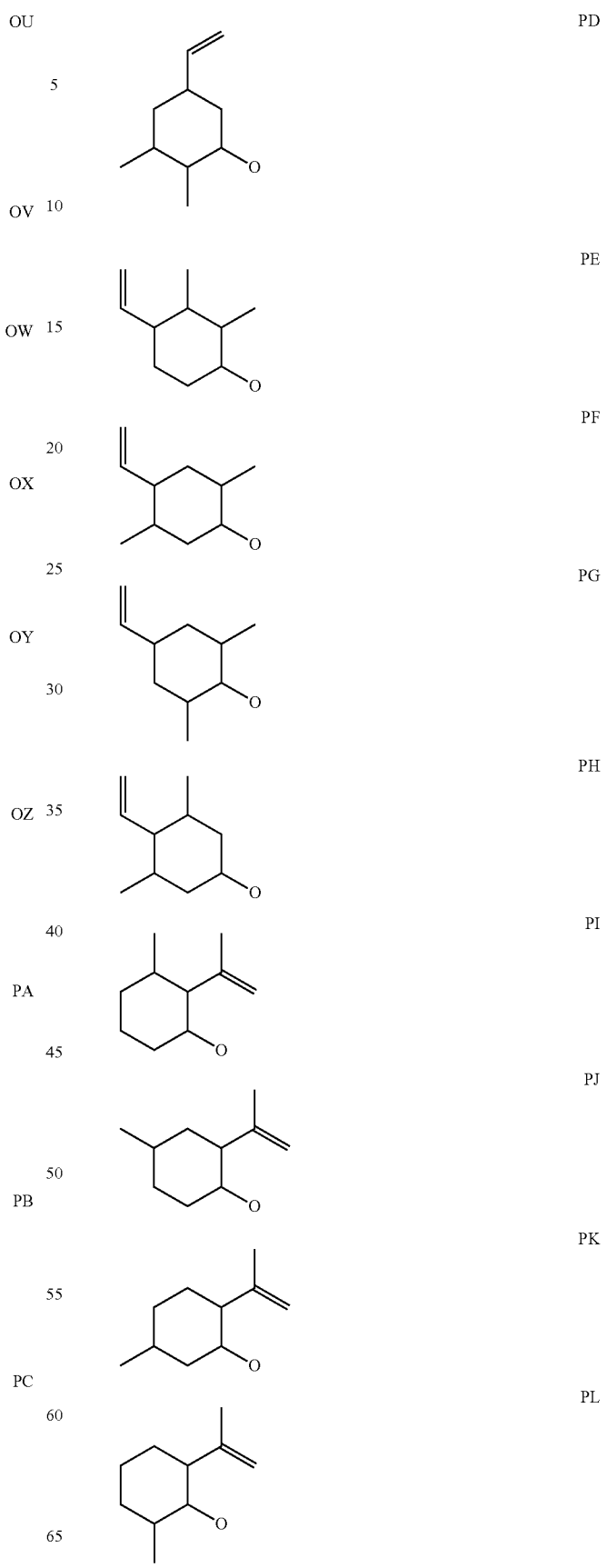

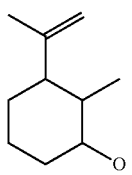
PM
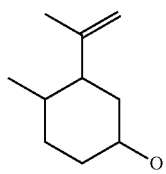
PN
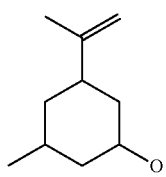
PO
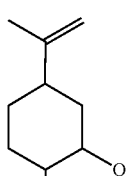
PP
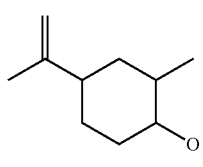
PQ
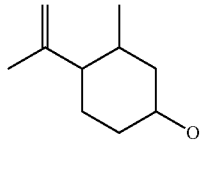
PR
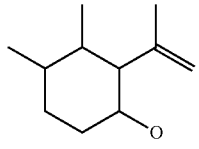
PS
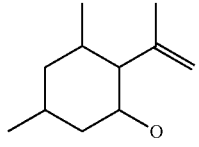
PT
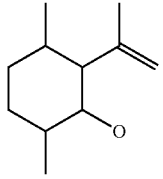
PU
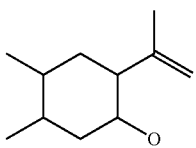
PV
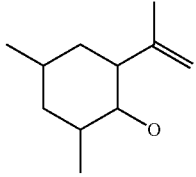
PW
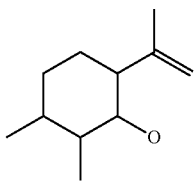
PX
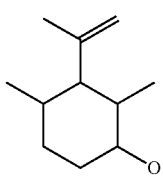
PY
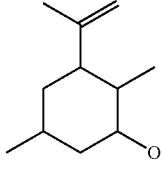
PZ
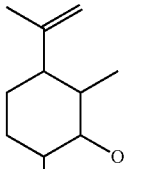
QA
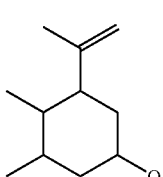
QB
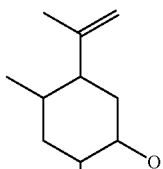
QC

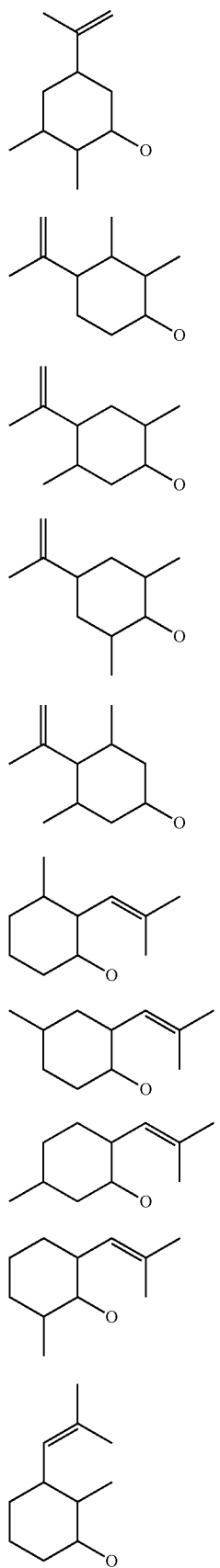
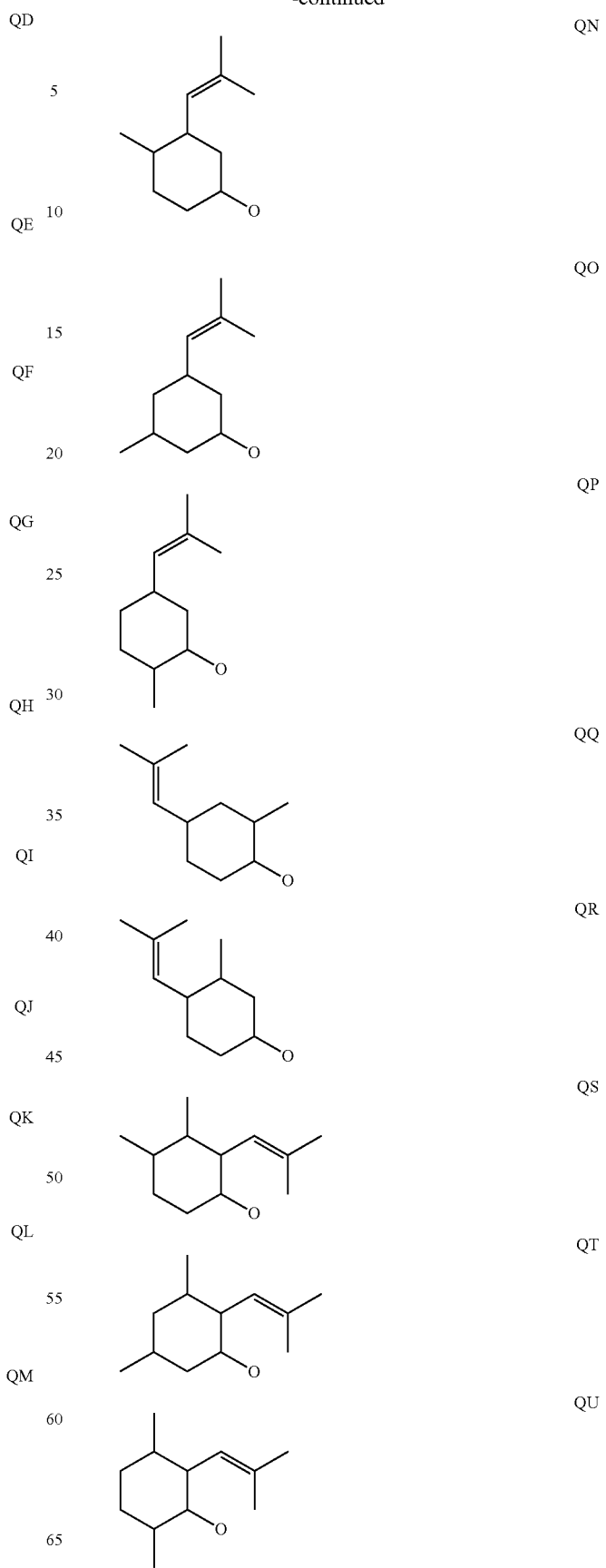

-continued
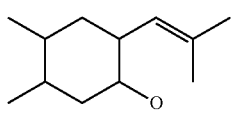
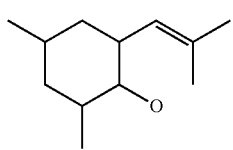
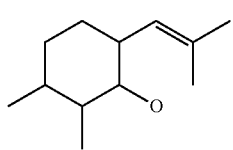
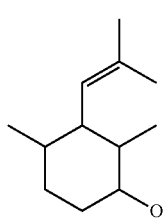
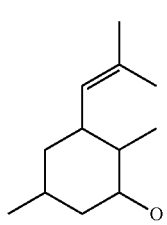
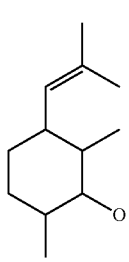
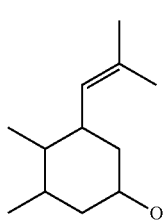
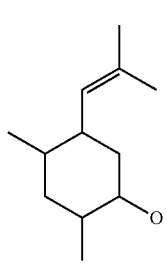
-continued
QV
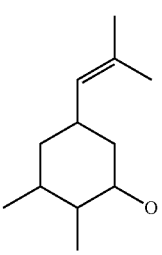
QW
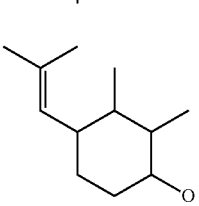
QX
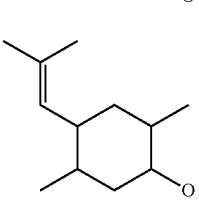
QY
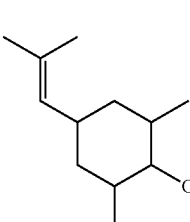
QZ
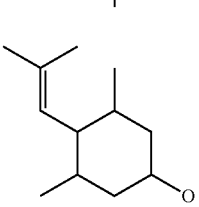
RA
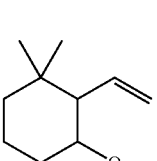
RB
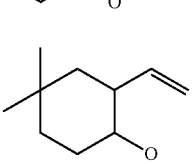
RC
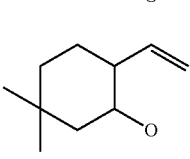
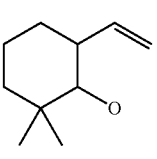
RD
RE
RF
RG
RH
RI
RJ
RK
RL

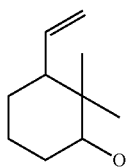
RM
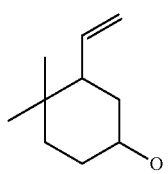
RN
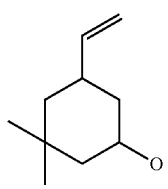
RO
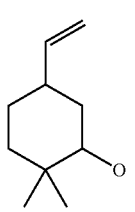
RP
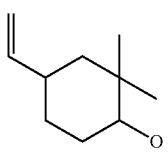
RQ
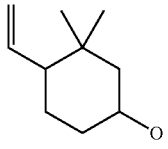
RR
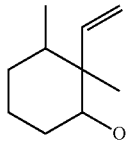
RS
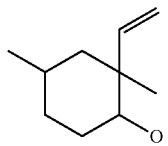
RT
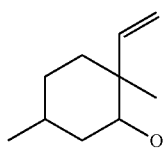
RU
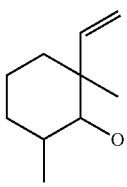
RV
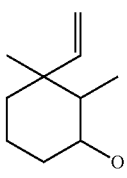
RW
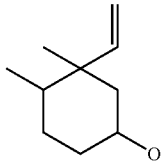
RX
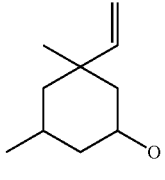
RY
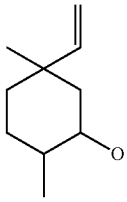
RZ
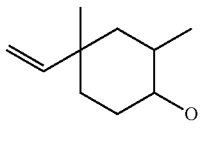
SA
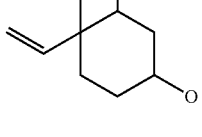
SB
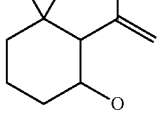
SC
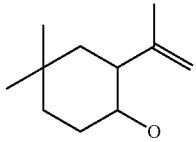
SD SE
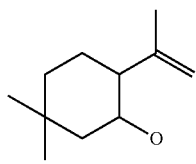
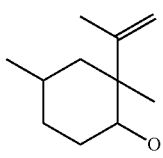
SN
SF
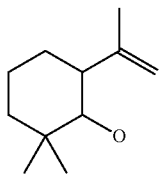
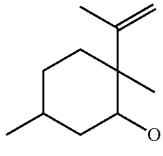
SO
SG
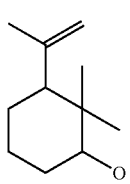
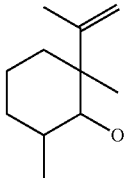
SP
SH
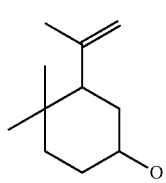
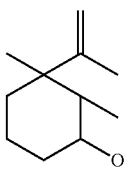
SQ
SI
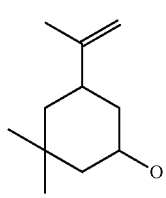
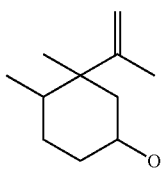
SR
SJ
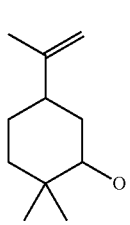
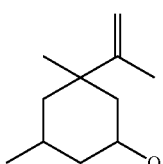
SS
SK
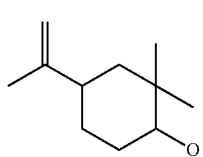
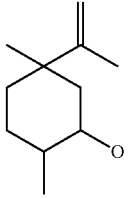
ST
SL
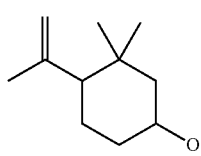
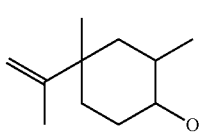
SU
SM
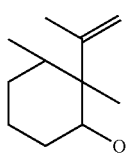
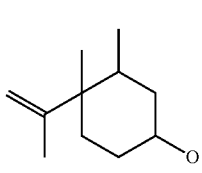
SV -continued
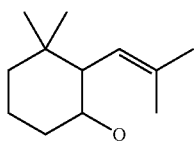
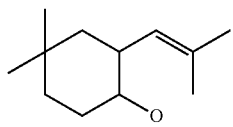
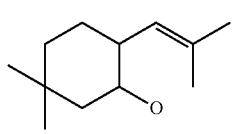
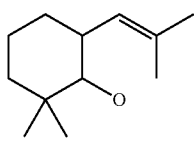
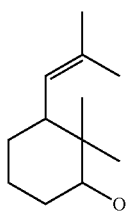
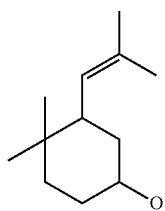
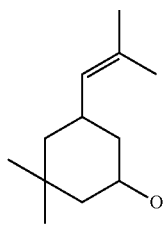
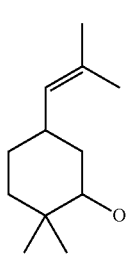
-continued
SW
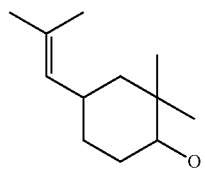
SX
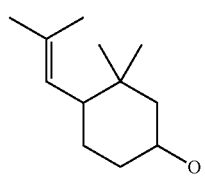
SY
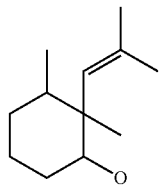
SZ
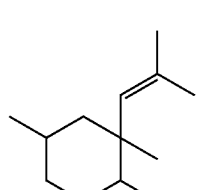
TA
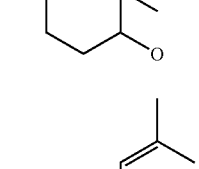
TB
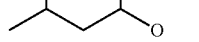
TC
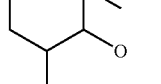
TD
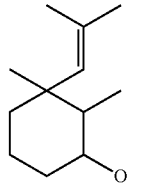
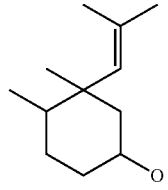
TE
TF
TG
TH
TI
TJ
TK
TL

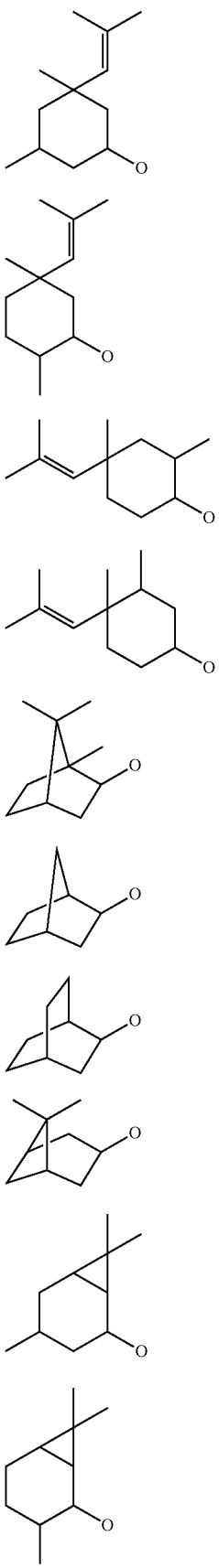
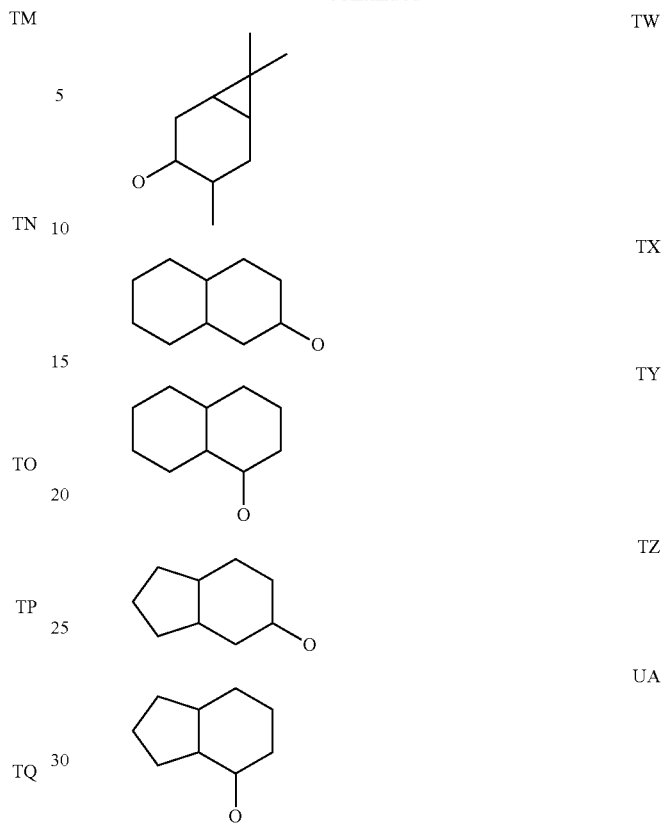
Preferred compounds of formulae (I), (Carb-I), (Carb-II) and (Carb-II-R1H) are those in which B denotes $NR^1R^2$, wherein preferably $R^1$ denotes hydrogen, and wherein $NR^2$ is a radical chosen from the following list "N":
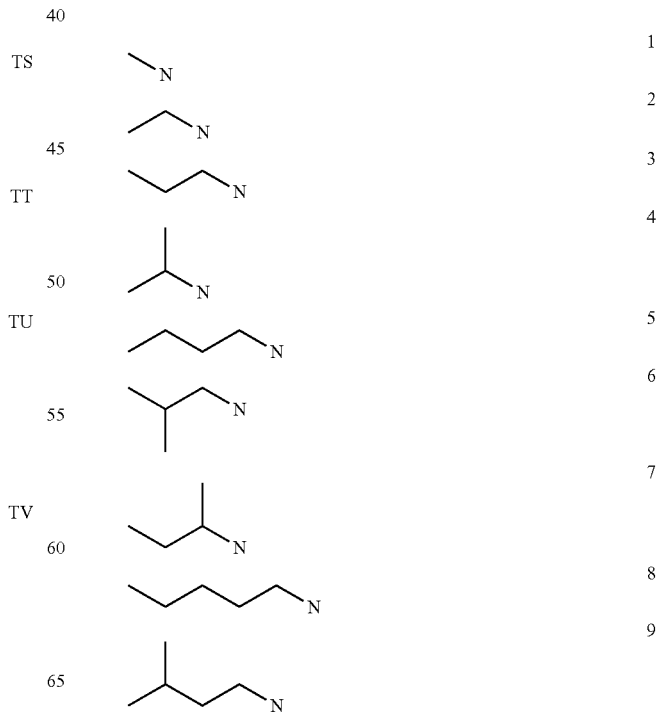

-continued
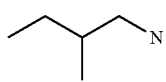
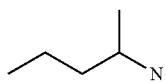
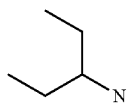
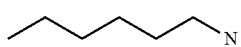
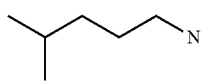
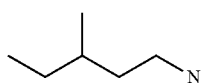
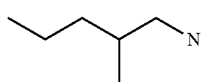
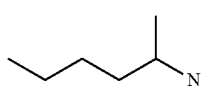
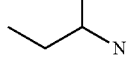
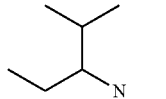
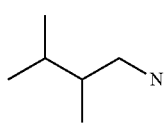
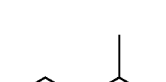
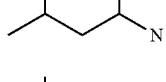
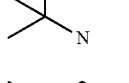
-continued
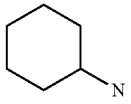
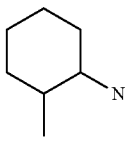
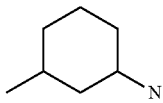
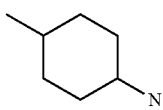
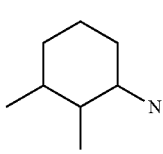
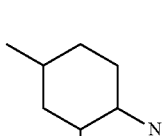
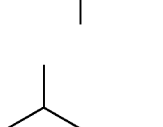
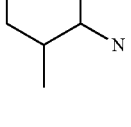
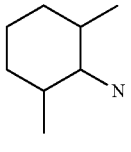
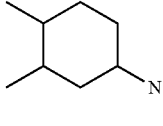
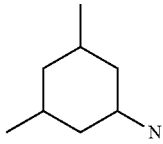
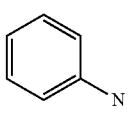

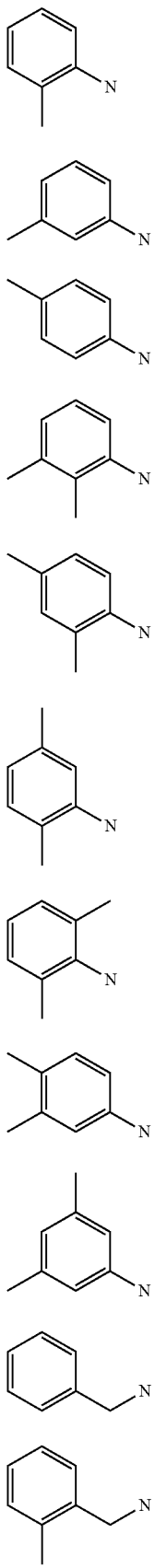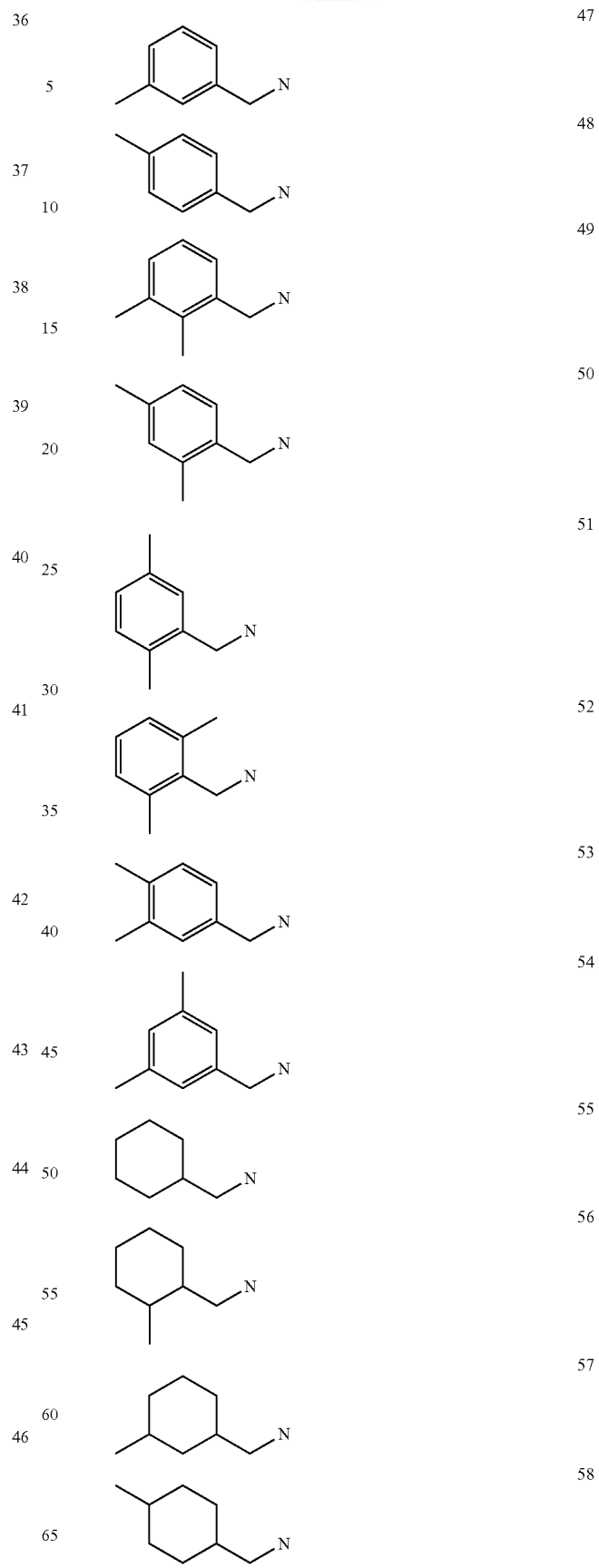

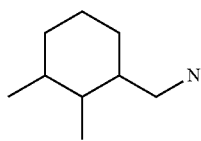
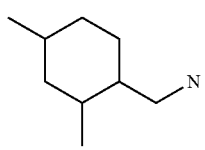
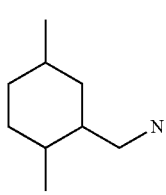
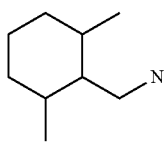
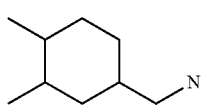
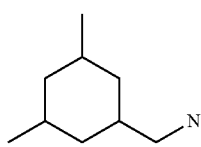
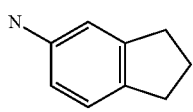
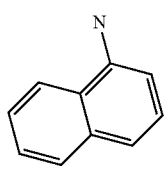
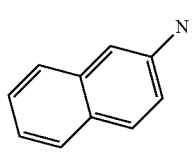
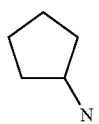
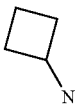
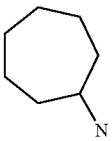
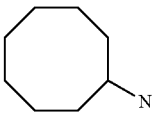
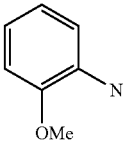
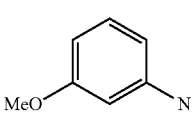
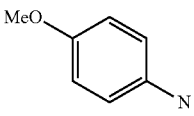
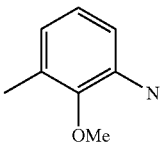
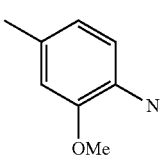
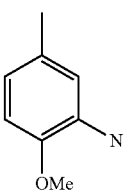
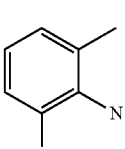
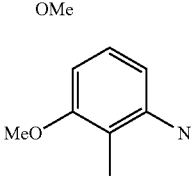

-continued
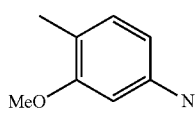
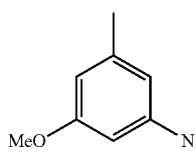
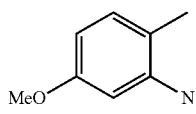
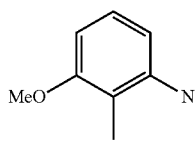
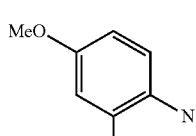
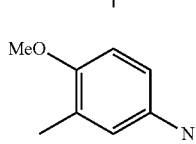
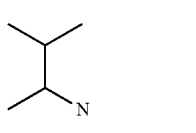
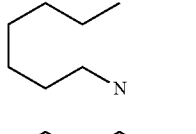
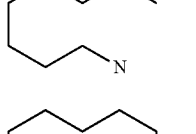
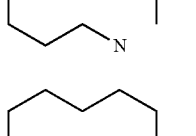
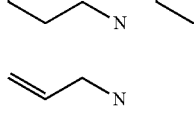
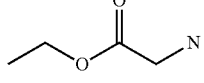
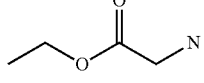
-continued
81 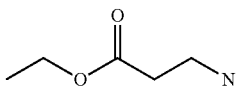
82 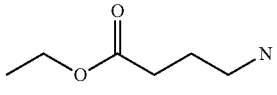
83 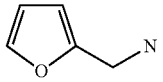
84 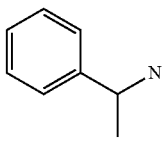
85 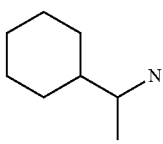
86 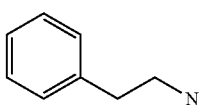
87 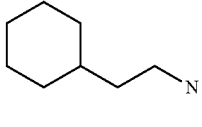
88 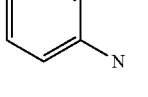
89 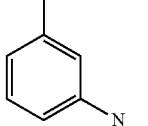
90 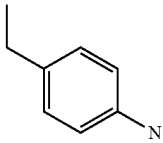
91 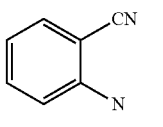
92 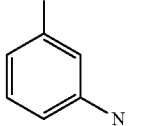

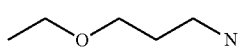
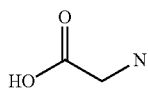
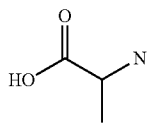
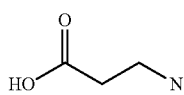
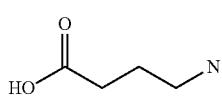
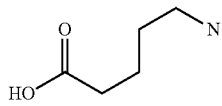
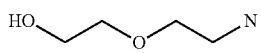
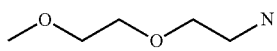
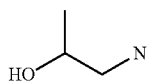
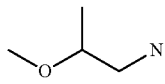
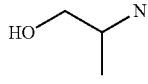
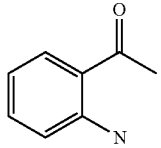
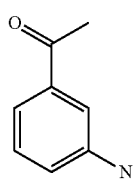
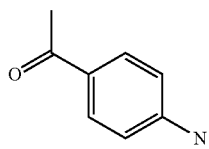
133
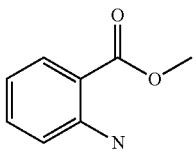
134
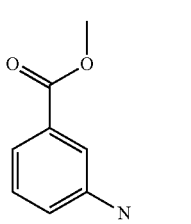
135
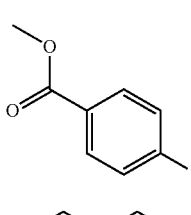
136
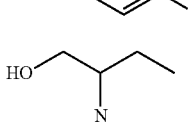
137
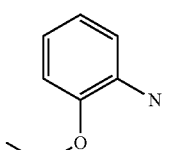
138
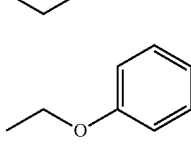
139
140
141
142
143
144
145
146
147
148
149
150
151
152
153
154
Preferred compounds of formulae (I), (Carb-I) and (Carb-II) are those in which B denotes $NR^1R^2$, wherein $NR^1R^2$ is a radical chosen from the following list "D":
201
202
203
204

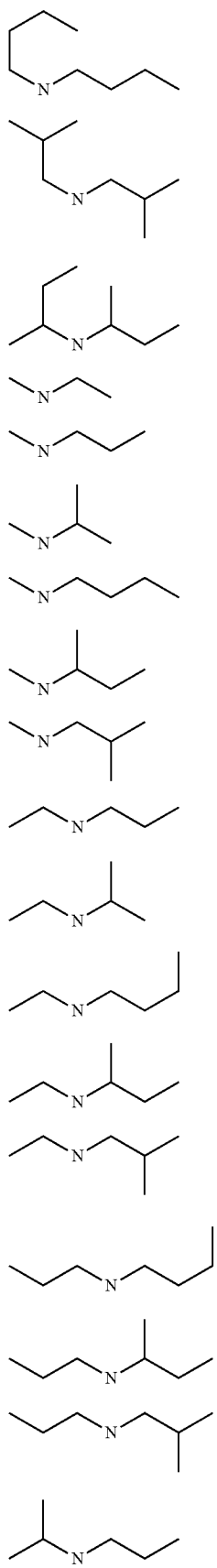
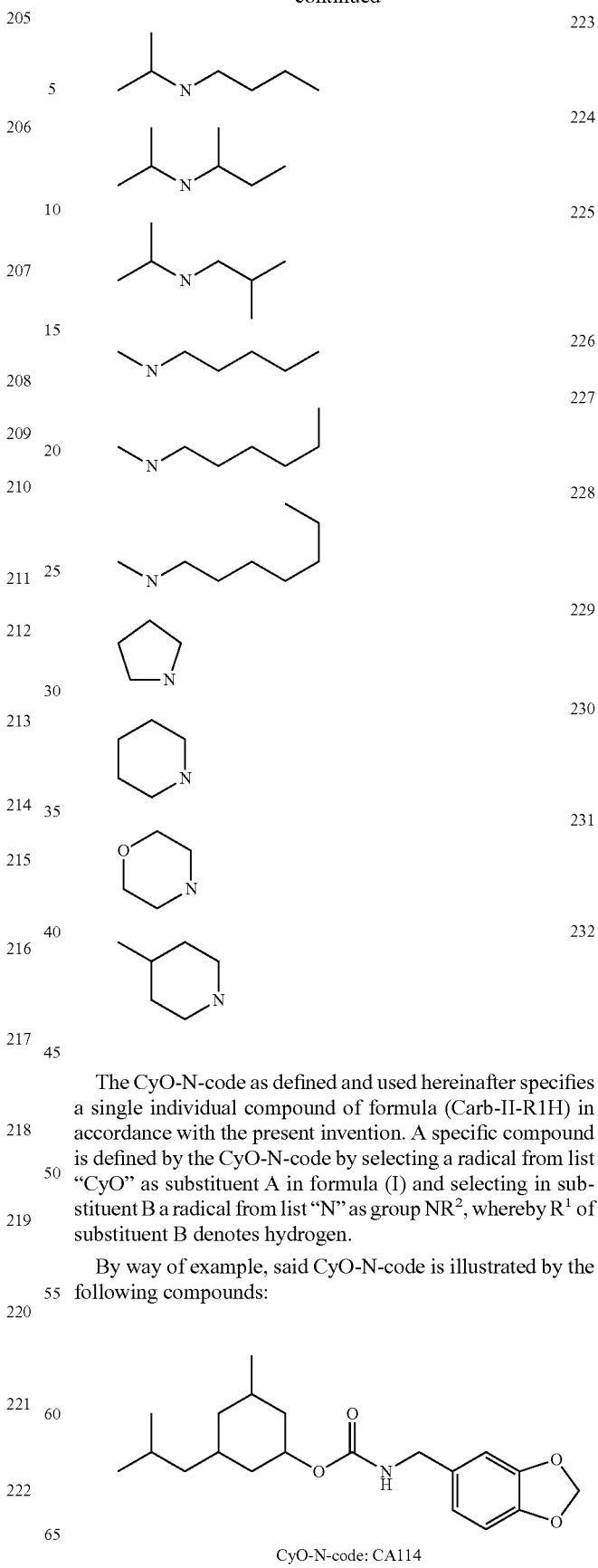

The CyO-N-code as defined and used hereinafter specifies a single individual compound of formula (Carb-II-R1H) in accordance with the present invention. A specific compound is defined by the CyO-N-code by selecting a radical from list "CyO" as substituent A in formula (I) and selecting in substituent B a radical from list "N" as group $NR^2$, whereby $R^1$ of substituent B denotes hydrogen.

By way of example, said CyO-N-code is illustrated by the following compounds:

CyO-N-code: CA114

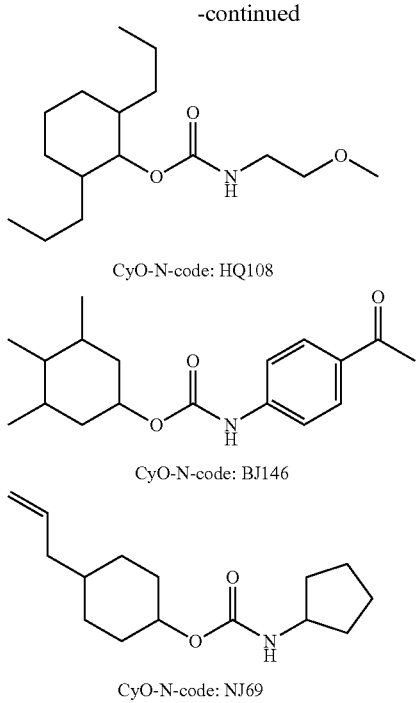

CyO-N-code: HQ108

CyO-N-code: BJ146

CyO-N-code: NJ69

The CyO-D-code as defined and used hereinafter specifies a single individual compound of formula (Carb-II) in accordance with the present invention. A specific compound is defined by the CyO-D-code by selecting a radical from list "CyO" as substituent A in formula (I) and selecting from list "D" as group substituent B in formula (I).

By way of example, said CyO-D-code is illustrated by the following compounds:

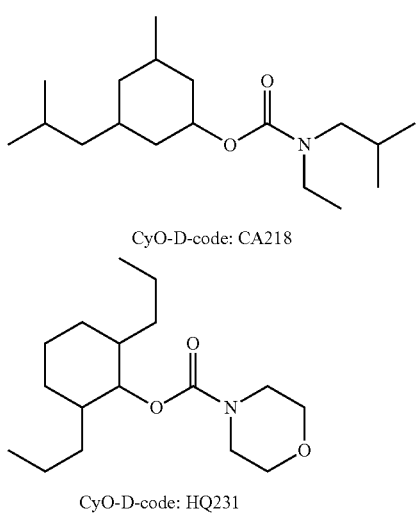

CyO-D-code: CA218

CyO-D-code: HQ231

Further preferred compounds of formula (I) are those in which B denotes $NHR^2$, wherein $NR^2$ corresponds to radical 1 of list "N", above, and A of formula (I) denotes one radical selected from list "CyO", above.

Further preferred compounds of formula (I) are those in which B denotes $NHR^2$, wherein $NR^2$ corresponds to radical 2 of list "N", above, and A of formula (I) denotes one radical selected from list "CyO", above.

Further preferred compounds of formula (I) are those in which B denotes $NHR^2$, wherein $NR^2$ corresponds to radical 3 of list "N", above, and A of formula (I) denotes one radical selected from list "CyO", above.

Further preferred compounds of formula (I) are those in which B denotes $NHR^2$, wherein $NR^2$ corresponds to radical 4 of list "N", above, and A of formula (I) denotes one radical selected from list "CyO", above.

Further preferred compounds of formula (I) are those in which B denotes $NHR^2$, wherein $NR^2$ corresponds to radical 5 of list "N", above, and A of formula (I) denotes one radical selected from list "CyO", above.

Further preferred compounds of formula (I) are those in which B denotes $NHR^2$, wherein $NR^2$ corresponds to radical 6 of list "N", above, and A of formula (I) denotes one radical selected from list "CyO", above.

Further preferred compounds of formula (I) are those in which B denotes $NHR^2$, wherein $NR^2$ corresponds to radical 7 of list "N", above, and A of formula (I) denotes one radical selected from list "CyO", above.

Further preferred compounds of formula (I) are those in which B denotes $NHR^2$, wherein $NR^2$ corresponds to radical 8 of list "N", above, and A of formula (I) denotes one radical selected from list "CyO", above.

Further preferred compounds of formula (I) are those in which B denotes $NHR^2$, wherein $NR^2$ corresponds to radical 9 of list "N", above, and A of formula (I) denotes one radical selected from list "CyO", above.

Further preferred compounds of formula (I) are those in which B denotes $NHR^2$, wherein $NR^2$ corresponds to radical 10 of list "N", above, and A of formula (I) denotes one radical selected from list "CyO", above.

Further preferred compounds of formula (I) are those in which B denotes $NHR^2$, wherein $NR^2$ corresponds to radical 11 of list "N", above, and A of formula (I) denotes one radical selected from list "CyO", above.

Further preferred compounds of formula (I) are those in which B denotes $NHR^2$, wherein $NR^2$ corresponds to radical 12 of list "N", above, and A of formula (I) denotes one radical selected from list "CyO", above.

Further preferred compounds of formula (I) are those in which B denotes $NHR^2$, wherein $NR^2$ corresponds to radical 13 of list "N", above, and A of formula (I) denotes one radical selected from list "CyO", above.

Further preferred compounds of formula (I) are those in which B denotes $NHR^2$, wherein $NR^2$ corresponds to radical 14 of list "N", above, and A of formula (I) denotes one radical selected from list "CyO", above.

Further preferred compounds of formula (I) are those in which B denotes $NHR^2$, wherein $NR^2$ corresponds to radical 15 of list "N", above, and A of formula (I) denotes one radical selected from list "CyO", above.

Further preferred compounds of formula (I) are those in which B denotes $NHR^2$, wherein $NR^2$ corresponds to radical 16 of list "N", above, and A of formula (I) denotes one radical selected from list "CyO", above.

Further preferred compounds of formula (I) are those in which B denotes $NHR^2$, wherein $NR^2$ corresponds to radical 17 of list "N", above, and A of formula (I) denotes one radical selected from list "CyO", above.

Further preferred compounds of formula (I) are those in which B denotes $NHR^2$, wherein $NR^2$ corresponds to radical 18 of list "N", above, and A of formula (I) denotes one radical selected from list "CyO", above.

Further preferred compounds of formula (I) are those in which B denotes $NHR^2$, wherein $NR^2$ corresponds to radical 19 of list "N", above, and A of formula (I) denotes one radical selected from list "CyO", above.

Further preferred compounds of formula (I) are those in which B denotes $NHR^2$, wherein $NR^2$ corresponds to radical 20 of list "N", above, and A of formula (I) denotes one radical selected from list "CyO", above.

Further preferred compounds of formula (I) are those in which B denotes $NHR^2$, wherein $NR^2$ corresponds to radical 21 of list "N", above, and A of formula (I) denotes one radical selected from list "CyO", above.

Further preferred compounds of formula (I) are those in which B denotes $NHR^2$, wherein $NR^2$ corresponds to radical 22 of list "N", above, and A of formula (I) denotes one radical selected from list "CyO", above.

Further preferred compounds of formula (I) are those in which B denotes $NHR^2$, wherein $NR^2$ corresponds to radical 23 of list "N", above, and A of formula (I) denotes one radical selected from list "CyO", above.

Further preferred compounds of formula (I) are those in which B denotes $NHR^2$, wherein $NR^2$ corresponds to radical 24 of list "N", above, and A of formula (I) denotes one radical selected from list "CyO", above.

Further preferred compounds of formula (I) are those in which B denotes $NHR^2$, wherein $NR^2$ corresponds to radical 25 of list "N", above, and A of formula (I) denotes one radical selected from list "CyO", above.

Further preferred compounds of formula (I) are those in which B denotes $NHR^2$, wherein $NR^2$ corresponds to radical 26 of list "N", above, and A of formula (I) denotes one radical selected from list "CyO", above.

Further preferred compounds of formula (I) are those in which B denotes $NHR^2$, wherein $NR^2$ corresponds to radical 27 of list "N", above, and A of formula (I) denotes one radical selected from list "CyO", above.

Further preferred compounds of formula (I) are those in which B denotes $NHR^2$, wherein $NR^2$ corresponds to radical 28 of list "N", above, and A of formula (I) denotes one radical selected from list "CyO", above.

Further preferred compounds of formula (I) are those in which B denotes $NHR^2$, wherein $NR^2$ corresponds to radical 29 of list "N", above, and A of formula (I) denotes one radical selected from list "CyO", above.

Further preferred compounds of formula (I) are those in which B denotes $NHR^2$, wherein $NR^2$ corresponds to radical 30 of list "N", above, and A of formula (I) denotes one radical selected from list "CyO", above.

Further preferred compounds of formula (I) are those in which B denotes $NHR^2$, wherein $NR^2$ corresponds to radical 31 of list "N", above, and A of formula (I) denotes one radical selected from list "CyO", above.

Further preferred compounds of formula (I) are those in which B denotes $NHR^2$, wherein $NR^2$ corresponds to radical 32 of list "N", above, and A of formula (I) denotes one radical selected from list "CyO", above.

Further preferred compounds of formula (I) are those in which B denotes $NHR^2$, wherein $NR^2$ corresponds to radical 33 of list "N", above, and A of formula (I) denotes one radical selected from list "CyO", above.

Further preferred compounds of formula (I) are those in which B denotes $NHR^2$, wherein $NR^2$ corresponds to radical 34 of list "N", above, and A of formula (I) denotes one radical selected from list "CyO", above.

Further preferred compounds of formula (I) are those in which B denotes $NHR^2$, wherein $NR^2$ corresponds to radical 35 of list "N", above, and A of formula (I) denotes one radical selected from list "CyO", above.

Further preferred compounds of formula (I) are those in which B denotes $NHR^2$, wherein $NR^2$ corresponds to radical 36 of list "N", above, and A of formula (I) denotes one radical selected from list "CyO", above.

Further preferred compounds of formula (I) are those in which B denotes $NHR^2$, wherein $NR^2$ corresponds to radical 37 of list "N", above, and A of formula (I) denotes one radical selected from list "CyO", above.

Further preferred compounds of formula (I) are those in which B denotes $NHR^2$, wherein $NR^2$ corresponds to radical 38 of list "N", above, and A of formula (I) denotes one radical selected from list "CyO", above.

Further preferred compounds of formula (I) are those in which B denotes $NHR^2$, wherein $NR^2$ corresponds to radical 39 of list "N", above, and A of formula (I) denotes one radical selected from list "CyO", above.

Further preferred compounds of formula (I) are those in which B denotes $NHR^2$, wherein $NR^2$ corresponds to radical 40 of list "N", above, and A of formula (I) denotes one radical selected from list "CyO", above.

Further preferred compounds of formula (I) are those in which B denotes $NHR^2$, wherein $NR^2$ corresponds to radical 41 of list "N", above, and A of formula (I) denotes one radical selected from list "CyO", above.

Further preferred compounds of formula (I) are those in which B denotes $NHR^2$, wherein $NR^2$ corresponds to radical 42 of list "N", above, and A of formula (I) denotes one radical selected from list "CyO", above.

Further preferred compounds of formula (I) are those in which B denotes $NHR^2$, wherein $NR^2$ corresponds to radical 43 of list "N", above, and A of formula (I) denotes one radical selected from list "CyO", above.

Further preferred compounds of formula (I) are those in which B denotes $NHR^2$, wherein $NR^2$ corresponds to radical 44 of list "N", above, and A of formula (I) denotes one radical selected from list "CyO", above.

Further preferred compounds of formula (I) are those in which B denotes $NHR^2$, wherein $NR^2$ corresponds to radical 45 of list "N", above, and A of formula (I) denotes one radical selected from list "CyO", above.

Further preferred compounds of formula (I) are those in which B denotes $NHR^2$, wherein $NR^2$ corresponds to radical 46 of list "N", above, and A of formula (I) denotes one radical selected from list "CyO", above.

Further preferred compounds of formula (I) are those in which B denotes $NHR^2$, wherein $NR^2$ corresponds to radical 47 of list "N", above, and A of formula (I) denotes one radical selected from list "CyO", above.

Further preferred compounds of formula (I) are those in which B denotes $NHR^2$, wherein $NR^2$ corresponds to radical 48 of list "N", above, and A of formula (I) denotes one radical selected from list "CyO", above.

Further preferred compounds of formula (I) are those in which B denotes $NHR^2$, wherein $NR^2$ corresponds to radical 49 of list "N", above, and A of formula (I) denotes one radical selected from list "CyO", above.

Further preferred compounds of formula (I) are those in which B denotes $NHR^2$, wherein $NR^2$ corresponds to radical 50 of list "N", above, and A of formula (I) denotes one radical selected from list "CyO", above.

Further preferred compounds of formula (I) are those in which B denotes $NHR^2$, wherein $NR^2$ corresponds to radical 51 of list "N", above, and A of formula (I) denotes one radical selected from list "CyO", above.

Further preferred compounds of formula (I) are those in which B denotes $NHR^2$, wherein $NR^2$ corresponds to radical 52 of list "N", above, and A of formula (I) denotes one radical selected from list "CyO", above.

Further preferred compounds of formula (I) are those in which B denotes NHR$^2$, wherein NR$^2$ corresponds to radical 53 of list "N", above, and A of formula (I) denotes one radical selected from list "CyO", above.

Further preferred compounds of formula (I) are those in which B denotes NHR$^2$, wherein NR$^2$ corresponds to radical 54 of list "N", above, and A of formula (I) denotes one radical selected from list "CyO", above.

Further preferred compounds of formula (I) are those in which B denotes NHR$^2$, wherein NR$^2$ corresponds to radical 55 of list "N", above, and A of formula (I) denotes one radical selected from list "CyO", above.

Further preferred compounds of formula (I) are those in which B denotes NHR$^2$, wherein NR$^2$ corresponds to radical 56 of list "N", above, and A of formula (I) denotes one radical selected from list "CyO", above.

Further preferred compounds of formula (I) are those in which B denotes NHR$^2$, wherein NR$^2$ corresponds to radical 57 of list "N", above, and A of formula (I) denotes one radical selected from list "CyO", above.

Further preferred compounds of formula (I) are those in which B denotes NHR$^2$, wherein NR$^2$ corresponds to radical 58 of list "N", above, and A of formula (I) denotes one radical selected from list "CyO", above.

Further preferred compounds of formula (I) are those in which B denotes NHR$^2$, wherein NR$^2$ corresponds to radical 59 of list "N", above, and A of formula (I) denotes one radical selected from list "CyO", above.

Further preferred compounds of formula (I) are those in which B denotes NHR$^2$, wherein NR$^2$ corresponds to radical 60 of list "N", above, and A of formula (I) denotes one radical selected from list "CyO", above.

Further preferred compounds of formula (I) are those in which B denotes NHR$^2$, wherein NR$^2$ corresponds to radical 61 of list "N", above, and A of formula (I) denotes one radical selected from list "CyO", above.

Further preferred compounds of formula (I) are those in which B denotes NHR$^2$, wherein NR$^2$ corresponds to radical 62 of list "N", above, and A of formula (I) denotes one radical selected from list "CyO", above.

Further preferred compounds of formula (I) are those in which B denotes NHR$^2$, wherein NR$^2$ corresponds to radical 63 of list "N", above, and A of formula (I) denotes one radical selected from list "CyO", above.

Further preferred compounds of formula (I) are those in which B denotes NHR$^2$, wherein NR$^2$ corresponds to radical 64 of list "N", above, and A of formula (I) denotes one radical selected from list "CyO", above.

Further preferred compounds of formula (I) are those in which B denotes NHR$^2$, wherein NR$^2$ corresponds to radical 65 of list "N", above, and A of formula (I) denotes one radical selected from list "CyO", above.

Further preferred compounds of formula (I) are those in which B denotes NHR$^2$, wherein NR$^2$ corresponds to radical 66 of list "N", above, and A of formula (I) denotes one radical selected from list "CyO", above.

Further preferred compounds of formula (I) are those in which B denotes NHR$^2$, wherein NR$^2$ corresponds to radical 67 of list "N", above, and A of formula (I) denotes one radical selected from list "CyO", above.

Further preferred compounds of formula (I) are those in which B denotes NHR$^2$, wherein NR$^2$ corresponds to radical 68 of list "N", above, and A of formula (I) denotes one radical selected from list "CyO", above.

Further preferred compounds of formula (I) are those in which B denotes NHR$^2$, wherein NR$^2$ corresponds to radical 69 of list "N", above, and A of formula (I) denotes one radical selected from list "CyO", above.

Further preferred compounds of formula (I) are those in which B denotes NHR$^2$, wherein NR$^2$ corresponds to radical 70 of list "N", above, and A of formula (I) denotes one radical selected from list "CyO", above.

Further preferred compounds of formula (I) are those in which B denotes NHR$^2$, wherein NR$^2$ corresponds to radical 71 of list "N", above, and A of formula (I) denotes one radical selected from list "CyO", above.

Further preferred compounds of formula (I) are those in which B denotes NHR$^2$, wherein NR$^2$ corresponds to radical 72 of list "N", above, and A of formula (I) denotes one radical selected from list "CyO", above.

Further preferred compounds of formula (I) are those in which B denotes NHR$^2$, wherein NR$^2$ corresponds to radical 73 of list "N", above, and A of formula (I) denotes one radical selected from list "CyO", above.

Further preferred compounds of formula (I) are those in which B denotes NHR$^2$, wherein NR$^2$ corresponds to radical 74 of list "N", above, and A of formula (I) denotes one radical selected from list "CyO", above.

Further preferred compounds of formula (I) are those in which B denotes NHR$^2$, wherein NR$^2$ corresponds to radical 75 of list "N", above, and A of formula (I) denotes one radical selected from list "CyO", above.

Further preferred compounds of formula (I) are those in which B denotes NHR$^2$, wherein NR$^2$ corresponds to radical 76 of list "N", above, and A of formula (I) denotes one radical selected from list "CyO", above.

Further preferred compounds of formula (I) are those in which B denotes NHR$^2$, wherein NR$^2$ corresponds to radical 77 of list "N", above, and A of formula (I) denotes one radical selected from list "CyO", above.

Further preferred compounds of formula (I) are those in which B denotes NHR$^2$, wherein NR$^2$ corresponds to radical 78 of list "N", above, and A of formula (I) denotes one radical selected from list "CyO", above.

Further preferred compounds of formula (I) are those in which B denotes NHR$^2$, wherein NR$^2$ corresponds to radical 79 of list "N", above, and A of formula (I) denotes one radical selected from list "CyO", above.

Further preferred compounds of formula (I) are those in which B denotes NHR$^2$, wherein NR$^2$ corresponds to radical 80 of list "N", above, and A of formula (I) denotes one radical selected from list "CyO", above.

Further preferred compounds of formula (I) are those in which B denotes NHR$^2$, wherein NR$^2$ corresponds to radical 81 of list "N", above, and A of formula (I) denotes one radical selected from list "CyO", above.

Further preferred compounds of formula (I) are those in which B denotes NHR$^2$, wherein NR$^2$ corresponds to radical 82 of list "N", above, and A of formula (I) denotes one radical selected from list "CyO", above.

Further preferred compounds of formula (I) are those in which B denotes NHR$^2$, wherein NR$^2$ corresponds to radical 83 of list "N", above, and A of formula (I) denotes one radical selected from list "CyO", above.

Further preferred compounds of formula (I) are those in which B denotes NHR$^2$, wherein NR$^2$ corresponds to radical 84 of list "N", above, and A of formula (I) denotes one radical selected from list "CyO", above.

Further preferred compounds of formula (I) are those in which B denotes NHR$^2$, wherein NR$^2$ corresponds to radical 85 of list "N", above, and A of formula (I) denotes one radical selected from list "CyO", above.

Further preferred compounds of formula (I) are those in which B denotes NHR$^2$, wherein NR$^2$ corresponds to radical 86 of list "N", above, and A of formula (I) denotes one radical selected from list "CyO", above.

Further preferred compounds of formula (I) are those in which B denotes NHR$^2$, wherein NR$^2$ corresponds to radical 87 of list "N", above, and A of formula (I) denotes one radical selected from list "CyO", above.

Further preferred compounds of formula (I) are those in which B denotes NHR$^2$, wherein NR$^2$ corresponds to radical 88 of list "N", above, and A of formula (I) denotes one radical selected from list "CyO", above.

Further preferred compounds of formula (I) are those in which B denotes NHR$^2$, wherein NR$^2$ corresponds to radical 89 of list "N", above, and A of formula (I) denotes one radical selected from list "CyO", above.

Further preferred compounds of formula (I) are those in which B denotes NHR$^2$, wherein NR$^2$ corresponds to radical 90 of list "N", above, and A of formula (I) denotes one radical selected from list "CyO", above.

Further preferred compounds of formula (I) are those in which B denotes NHR$^2$, wherein NR$^2$ corresponds to radical 91 of list "N", above, and A of formula (I) denotes one radical selected from list "CyO", above.

Further preferred compounds of formula (I) are those in which B denotes NHR$^2$, wherein NR$^2$ corresponds to radical 92 of list "N", above, and A of formula (I) denotes one radical selected from list "CyO", above.

Further preferred compounds of formula (I) are those in which B denotes NHR$^2$, wherein NR$^2$ corresponds to radical 93 of list "N", above, and A of formula (I) denotes one radical selected from list "CyO", above.

Further preferred compounds of formula (I) are those in which B denotes NHR$^2$, wherein NR$^2$ corresponds to radical 94 of list "N", above, and A of formula (I) denotes one radical selected from list "CyO", above.

Further preferred compounds of formula (I) are those in which B denotes NHR$^2$, wherein NR$^2$ corresponds to radical 95 of list "N", above, and A of formula (I) denotes one radical selected from list "CyO", above.

Further preferred compounds of formula (I) are those in which B denotes NHR$^2$, wherein NR$^2$ corresponds to radical 96 of list "N", above, and A of formula (I) denotes one radical selected from list "CyO", above.

Further preferred compounds of formula (I) are those in which B denotes NHR$^2$, wherein NR$^2$ corresponds to radical 97 of list "N", above, and A of formula (I) denotes one radical selected from list "CyO", above.

Further preferred compounds of formula (I) are those in which B denotes NHR$^2$, wherein NR$^2$ corresponds to radical 98 of list "N", above, and A of formula (I) denotes one radical selected from list "CyO", above.

Further preferred compounds of formula (I) are those in which B denotes NHR$^2$, wherein NR$^2$ corresponds to radical 99 of list "N", above, and A of formula (I) denotes one radical selected from list "CyO", above.

Further preferred compounds of formula (I) are those in which B denotes NHR$^2$, wherein NR$^2$ corresponds to radical 100 of list "N", above, and A of formula (I) denotes one radical selected from list "CyO", above.

Further preferred compounds of formula (I) are those in which B denotes NHR$^2$, wherein NR$^2$ corresponds to radical 101 of list "N", above, and A of formula (I) denotes one radical selected from list "CyO", above.

Further preferred compounds of formula (I) are those in which B denotes NHR$^2$, wherein NR$^2$ corresponds to radical 102 of list "N", above, and A of formula (I) denotes one radical selected from list "CyO", above.

Further preferred compounds of formula (I) are those in which B denotes NHR$^2$, wherein NR$^2$ corresponds to radical 103 of list "N", above, and A of formula (I) denotes one radical selected from list "CyO", above.

Further preferred compounds of formula (I) are those in which B denotes NHR$^2$, wherein NR$^2$ corresponds to radical 104 of list "N", above, and A of formula (I) denotes one radical selected from list "CyO", above.

Further preferred compounds of formula (I) are those in which B denotes NHR$^2$, wherein NR$^2$ corresponds to radical 105 of list "N", above, and A of formula (I) denotes one radical selected from list "CyO", above.

Further preferred compounds of formula (I) are those in which B denotes NHR$^2$, wherein NR$^2$ corresponds to radical 106 of list "N", above, and A of formula (I) denotes one radical selected from list "CyO", above.

Further preferred compounds of formula (I) are those in which B denotes NHR$^2$, wherein NR$^2$ corresponds to radical 107 of list "N", above, and A of formula (I) denotes one radical selected from list "CyO", above.

Further preferred compounds of formula (I) are those in which B denotes NHR$^2$, wherein NR$^2$ corresponds to radical 108 of list "N", above, and A of formula (I) denotes one radical selected from list "CyO", above.

Further preferred compounds of formula (I) are those in which B denotes NHR$^2$, wherein NR$^2$ corresponds to radical 109 of list "N", above, and A of formula (I) denotes one radical selected from list "CyO", above.

Further preferred compounds of formula (I) are those in which B denotes NHR$^2$, wherein NR$^2$ corresponds to radical 110 of list "N", above, and A of formula (I) denotes one radical selected from list "CyO", above.

Further preferred compounds of formula (I) are those in which B denotes NHR$^2$, wherein NR$^2$ corresponds to radical 111 of list "N", above, and A of formula (I) denotes one radical selected from list "CyO", above.

Further preferred compounds of formula (I) are those in which B denotes NHR$^2$, wherein NR$^2$ corresponds to radical 112 of list "N", above, and A of formula (I) denotes one radical selected from list "CyO", above.

Further preferred compounds of formula (I) are those in which B denotes NHR$^2$, wherein NR$^2$ corresponds to radical 113 of list "N", above, and A of formula (I) denotes one radical selected from list "CyO", above.

Further preferred compounds of formula (I) are those in which B denotes NHR$^2$, wherein NR$^2$ corresponds to radical 114 of list "N", above, and A of formula (I) denotes one radical selected from list "CyO", above.

Further preferred compounds of formula (I) are those in which B denotes NHR$^2$, wherein NR$^2$ corresponds to radical 115 of list "N", above, and A of formula (I) denotes one radical selected from list "CyO", above.

Further preferred compounds of formula (I) are those in which B denotes NHR$^2$, wherein NR$^2$ corresponds to radical 116 of list "N", above, and A of formula (I) denotes one radical selected from list "CyO", above.

Further preferred compounds of formula (I) are those in which B denotes NHR$^2$, wherein NR$^2$ corresponds to radical 117 of list "N", above, and A of formula (I) denotes one radical selected from list "CyO", above.

Further preferred compounds of formula (I) are those in which B denotes NHR$^2$, wherein NR$^2$ corresponds to radical 118 of list "N", above, and A of formula (I) denotes one radical selected from list "CyO", above.

Further preferred compounds of formula (I) are those in which B denotes $NHR^2$, wherein $NR^2$ corresponds to radical 119 of list "N", above, and A of formula (I) denotes one radical selected from list "CyO", above.

Further preferred compounds of formula (I) are those in which B denotes $NHR^2$, wherein $NR^2$ corresponds to radical 120 of list "N", above, and A of formula (I) denotes one radical selected from list "CyO", above.

Further preferred compounds of formula (I) are those in which B denotes $NHR^2$, wherein $NR^2$ corresponds to radical 121 of list "N", above, and A of formula (I) denotes one radical selected from list "CyO", above.

Further preferred compounds of formula (I) are those in which B denotes $NHR^2$, wherein $NR^2$ corresponds to radical 122 of list "N", above, and A of formula (I) denotes one radical selected from list "CyO", above.

Further preferred compounds of formula (I) are those in which B denotes $NHR^2$, wherein $NR^2$ corresponds to radical 123 of list "N", above, and A of formula (I) denotes one radical selected from list "CyO", above.

Further preferred compounds of formula (I) are those in which B denotes $NHR^2$, wherein $NR^2$ corresponds to radical 124 of list "N", above, and A of formula (I) denotes one radical selected from list "CyO", above.

Further preferred compounds of formula (I) are those in which B denotes $NHR^2$, wherein $NR^2$ corresponds to radical 125 of list "N", above, and A of formula (I) denotes one radical selected from list "CyO", above.

Further preferred compounds of formula (I) are those in which B denotes $NHR^2$, wherein $NR^2$ corresponds to radical 126 of list "N", above, and A of formula (I) denotes one radical selected from list "CyO", above.

Further preferred compounds of formula (I) are those in which B denotes $NHR^2$, wherein $NR^2$ corresponds to radical 127 of list "N", above, and A of formula (I) denotes one radical selected from list "CyO", above.

Further preferred compounds of formula (I) are those in which B denotes $NHR^2$, wherein $NR^2$ corresponds to radical 128 of list "N", above, and A of formula (I) denotes one radical selected from list "CyO", above.

Further preferred compounds of formula (I) are those in which B denotes $NHR^2$, wherein $NR^2$ corresponds to radical 129 of list "N", above, and A of formula (I) denotes one radical selected from list "CyO", above.

Further preferred compounds of formula (I) are those in which B denotes $NHR^2$, wherein $NR^2$ corresponds to radical 130 of list "N", above, and A of formula (I) denotes one radical selected from list "CyO", above.

Further preferred compounds of formula (I) are those in which B denotes $NHR^2$, wherein $NR^2$ corresponds to radical 131 of list "N", above, and A of formula (I) denotes one radical selected from list "CyO", above.

Further preferred compounds of formula (I) are those in which B denotes $NHR^2$, wherein $NR^2$ corresponds to radical 132 of list "N", above, and A of formula (I) denotes one radical selected from list "CyO", above.

Further preferred compounds of formula (I) are those in which B denotes $NHR^2$, wherein $NR^2$ corresponds to radical 133 of list "N", above, and A of formula (I) denotes one radical selected from list "CyO", above.

Further preferred compounds of formula (I) are those in which B denotes $NHR^2$, wherein $NR^2$ corresponds to radical 134 of list "N", above, and A of formula (I) denotes one radical selected from list "CyO", above.

Further preferred compounds of formula (I) are those in which B denotes $NHR^2$, wherein $NR^2$ corresponds to radical 135 of list "N", above, and A of formula (I) denotes one radical selected from list "CyO", above.

Further preferred compounds of formula (I) are those in which B denotes $NHR^2$, wherein $NR^2$ corresponds to radical 136 of list "N", above, and A of formula (I) denotes one radical selected from list "CyO", above.

Further preferred compounds of formula (I) are those in which B denotes $NHR^2$, wherein $NR^2$ corresponds to radical 137 of list "N", above, and A of formula (I) denotes one radical selected from list "CyO", above.

Further preferred compounds of formula (I) are those in which B denotes $NHR^2$, wherein $NR^2$ corresponds to radical 138 of list "N", above, and A of formula (I) denotes one radical selected from list "CyO", above.

Further preferred compounds of formula (I) are those in which B denotes $NHR^2$, wherein $NR^2$ corresponds to radical 139 of list "N", above, and A of formula (I) denotes one radical selected from list "CyO", above.

Further preferred compounds of formula (I) are those in which B denotes $NHR^2$, wherein $NR^2$ corresponds to radical 140 of list "N", above, and A of formula (I) denotes one radical selected from list "CyO", above.

Further preferred compounds of formula (I) are those in which B denotes $NHR^2$, wherein $NR^2$ corresponds to radical 141 of list "N", above, and A of formula (I) denotes one radical selected from list "CyO", above.

Further preferred compounds of formula (I) are those in which B denotes $NHR^2$, wherein $NR^2$ corresponds to radical 142 of list "N", above, and A of formula (I) denotes one radical selected from list "CyO", above.

Further preferred compounds of formula (I) are those in which B denotes $NHR^2$, wherein $NR^2$ corresponds to radical 143 of list "N", above, and A of formula (I) denotes one radical selected from list "CyO", above.

Further preferred compounds of formula (I) are those in which B denotes $NHR^2$, wherein $NR^2$ corresponds to radical 144 of list "N", above, and A of formula (I) denotes one radical selected from list "CyO", above.

Further preferred compounds of formula (I) are those in which B denotes $NHR^2$, wherein $NR^2$ corresponds to radical 145 of list "N", above, and A of formula (I) denotes one radical selected from list "CyO", above.

Further preferred compounds of formula (I) are those in which B denotes $NHR^2$, wherein $NR^2$ corresponds to radical 146 of list "N", above, and A of formula (I) denotes one radical selected from list "CyO", above.

Further preferred compounds of formula (I) are those in which B denotes $NHR^2$, wherein $NR^2$ corresponds to radical 147 of list "N", above, and A of formula (I) denotes one radical selected from list "CyO", above.

Further preferred compounds of formula (I) are those in which B denotes $NHR^2$, wherein $NR^2$ corresponds to radical 148 of list "N", above, and A of formula (I) denotes one radical selected from list "CyO", above.

Further preferred compounds of formula (I) are those in which B denotes $NHR^2$, wherein $NR^2$ corresponds to radical 149 of list "N", above, and A of formula (I) denotes one radical selected from list "CyO", above.

Further preferred compounds of formula (I) are those in which B denotes $NHR^2$, wherein $NR^2$ corresponds to radical 150 of list "N", above, and A of formula (I) denotes one radical selected from list "CyO", above.

Further preferred compounds of formula (I) are those in which B denotes $NHR^2$, wherein $NR^2$ corresponds to radical 151 of list "N", above, and A of formula (I) denotes one radical selected from list "CyO", above.

Further preferred compounds of formula (I) are those in which B denotes NHR², wherein NR² corresponds to radical 152 of list "N", above, and A of formula (I) denotes one radical selected from list "CyO", above.

Further preferred compounds of formula (I) are those in which B denotes NHR², wherein NR² corresponds to radical 153 of list "N", above, and A of formula (I) denotes one radical selected from list "CyO", above.

Further preferred compounds of formula (I) are those in which B denotes NHR², wherein NR² corresponds to radical 154 of list "N", above, and A of formula (I) denotes one radical selected from list "CyO", above.

However, in the context of the present invention, and depending on the circumstances, each individual compound of the compounds of formula (Carb-II-R1H), in particular those defined by the CyO-N-code, may for technical or non-technical reasons, as the case may be, in some embodiments be more preferred or less preferred than other compounds of formula (Carb-II-R1H), in particular those defined by the CyO-N-code. Thus, in some cases, compounds of formula (Carb-II-R1H) as defined by the CyO-N-code do not necessarily share the same level of preference.

Further preferred compounds of formula (I) are those in which B denotes NR¹R², wherein NR¹R² corresponds to radical 201 of list "D", above, and A of formula (I) denotes one radical selected from list "CyO", above.

Further preferred compounds of formula (I) are those in which B denotes NR¹R², wherein NR¹R² corresponds to radical 202 of list "D", above, and A of formula (I) denotes one radical selected from list "CyO", above.

Further preferred compounds of formula (I) are those in which B denotes NR¹R², wherein NR¹R² corresponds to radical 203 of list "D", above, and A of formula (I) denotes one radical selected from list "CyO", above.

Further preferred compounds of formula (I) are those in which B denotes NR¹R², wherein NR¹R² corresponds to radical 204 of list "D", above, and A of formula (I) denotes one radical selected from list "CyO", above.

Further preferred compounds of formula (I) are those in which B denotes NR¹R², wherein NR¹R² corresponds to radical 205 of list "D", above, and A of formula (I) denotes one radical selected from list "CyO", above.

Further preferred compounds of formula (I) are those in which B denotes NR¹R², wherein NR¹R² corresponds to radical 206 of list "D", above, and A of formula (I) denotes one radical selected from list "CyO", above.

Further preferred compounds of formula (I) are those in which B denotes NR¹R², wherein NR¹R² corresponds to radical 207 of list "D", above, and A of formula (I) denotes one radical selected from list "CyO", above.

Further preferred compounds of formula (I) are those in which B denotes NR¹R², wherein NR¹R² corresponds to radical 208 of list "D", above, and A of formula (I) denotes one radical selected from list "CyO", above.

Further preferred compounds of formula (I) are those in which B denotes NR¹R², wherein NR¹R² corresponds to radical 209 of list "D", above, and A of formula (I) denotes one radical selected from list "CyO", above.

Further preferred compounds of formula (I) are those in which B denotes NR¹R², wherein NR¹R² corresponds to radical 210 of list "D", above, and A of formula (I) denotes one radical selected from list "CyO", above.

Further preferred compounds of formula (I) are those in which B denotes NR¹R², wherein NR¹R² corresponds to radical 211 of list "D", above, and A of formula (I) denotes one radical selected from list "CyO", above.

Further preferred compounds of formula (I) are those in which B denotes NR¹R², wherein NR¹R² corresponds to radical 212 of list "D", above, and A of formula (I) denotes one radical selected from list "CyO", above.

Further preferred compounds of formula (I) are those in which B denotes NR¹R², wherein NR¹R² corresponds to radical 213 of list "D", above, and A of formula (I) denotes one radical selected from list "CyO", above.

Further preferred compounds of formula (I) are those in which B denotes NR¹R², wherein NR¹R² corresponds to radical 214 of list "D", above, and A of formula (I) denotes one radical selected from list "CyO", above.

Further preferred compounds of formula (I) are those in which B denotes NR¹R², wherein NR¹R² corresponds to radical 215 of list "D", above, and A of formula (I) denotes one radical selected from list "CyO", above.

Further preferred compounds of formula (I) are those in which B denotes NR¹R², wherein NR¹R² corresponds to radical 216 of list "D", above, and A of formula (I) denotes one radical selected from list "CyO", above.

Further preferred compounds of formula (I) are those in which B denotes NR¹R², wherein NR¹R² corresponds to radical 217 of list "D", above, and A of formula (I) denotes one radical selected from list "CyO", above.

Further preferred compounds of formula (I) are those in which B denotes NR¹R², wherein NR¹R² corresponds to radical 218 of list "D", above, and A of formula (I) denotes one radical selected from list "CyO", above.

Further preferred compounds of formula (I) are those in which B denotes NR¹R², wherein NR¹R² corresponds to radical 219 of list "D", above, and A of formula (I) denotes one radical selected from list "CyO", above.

Further preferred compounds of formula (I) are those in which B denotes NR¹R², wherein NR¹R² corresponds to radical 220 of list "D", above, and A of formula (I) denotes one radical selected from list "CyO", above.

Further preferred compounds of formula (I) are those in which B denotes NR¹R², wherein NR¹R² corresponds to radical 221 of list "D", above, and A of formula (I) denotes one radical selected from list "CyO", above.

Further preferred compounds of formula (I) are those in which B denotes NR¹R², wherein NR¹R² corresponds to radical 222 of list "D", above, and A of formula (I) denotes one radical selected from list "CyO", above.

Further preferred compounds of formula (I) are those in which B denotes NR¹R², wherein NR¹R² corresponds to radical 223 of list "D", above, and A of formula (I) denotes one radical selected from list "CyO", above.

Further preferred compounds of formula (I) are those in which B denotes NR¹R², wherein NR¹R² corresponds to radical 224 of list "D", above, and A of formula (I) denotes one radical selected from list "CyO", above.

Further preferred compounds of formula (I) are those in which B denotes NR¹R², wherein NR¹R² corresponds to radical 225 of list "D", above, and A of formula (I) denotes one radical selected from list "CyO", above.

Further preferred compounds of formula (I) are those in which B denotes NR¹R², wherein NR¹R² corresponds to radical 226 of list "D", above, and A of formula (I) denotes one radical selected from list "CyO", above.

Further preferred compounds of formula (I) are those in which B denotes NR¹R², wherein NR¹R² corresponds to radical 227 of list "D", above, and A of formula (I) denotes one radical selected from list "CyO", above.

Further preferred compounds of formula (I) are those in which B denotes $NR^1R^2$, wherein $NR^1R^2$ corresponds to radical 228 of list "D", above, and A of formula (I) denotes one radical selected from list "CyO", above.

Further preferred compounds of formula (I) are those in which B denotes $NR^1R^2$, wherein $NR^1R^2$ corresponds to radical 229 of list "D", above, and A of formula (I) denotes one radical selected from list "CyO", above.

Further preferred compounds of formula (I) are those in which B denotes $NR^1R^2$, wherein $NR^1R^2$ corresponds to radical 230 of list "D", above, and A of formula (I) denotes one radical selected from list "CyO", above.

Further preferred compounds of formula (I) are those in which B denotes $NR^1R^2$, wherein $NR^1R^2$ corresponds to radical 231 of list "D", above, and A of formula (I) denotes one radical selected from list "CyO", above.

Further preferred compounds of formula (I) are those in which B denotes $NR^1R^2$, wherein $NR^1R^2$ corresponds to radical 232 of list "D", above, and A of formula (I) denotes one radical selected from list "CyO", above.

However, in the context of the present invention, and depending on the circumstances, each individual compound of the compounds of formula (Carb-II), in particular those defined by the CyO-D-code, may for technical or non-technical reasons, as the case may be, in some embodiments be more preferred or less preferred than other compounds of formula (Carb-II), in particular those defined by the CyO-D-code. Thus, in some cases, compounds defined by the CyO-D-code do not necessarily share the same level of preference.

Several compounds of formula (I), in particular the preferred compounds according to the present invention, are identified and referred to using an arbitrary internal reference-numbering system of the type "BIO", followed by a four-digit number.

In one preferred embodiment, preferred cyclohexyl carbamates of formula (Carb-II) are those wherein $R^1$ denotes an alkyl radical having 1 to 8 carbon atoms, preferably an alkyl radical having 1 to 4 carbon atoms and X, Y, Z and $R^2$ have the (preferred or particularly preferred) meaning given hereinbefore or hereinafter.

In a preferred embodiment, particularly preferred N,N-dialkyl-cyclohexyl carbamates of formula (Carb-II) are the following:

In another preferred embodiment, compounds of formulae (I), (Carb-I), (Carb-II) and (Carb-II-R1H), X, Y and Z each denote hydrogen.

Such cyclohexyl carbamates are derived from unsubstituted cyclohexanols, thus to compounds of formula (I) in which A denotes:

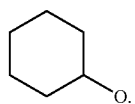

A particularly preferred cyclohexyl carbamate, derived from unsubstituted cyclohexanol is:

BIO1741: Phenyl-carbamic acid cyclohexyl ester (corresponding to CyO-N-code AA35)

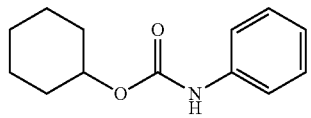

In another preferred embodiment, preferred compounds of formulae (I), (Carb-I), (Carb-II) and (Carb-II-R1H), are those in which X denotes $C_1$-$C_4$-alkyl or $C_2$-$C_4$-alkenyl and Y and Z both denote hydrogen.

Such cyclohexyl carbamates are derived from monosubstituted cyclohexanols, thus to compounds of formula (I) in which A denotes

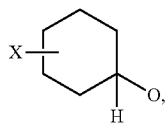

wherein X has the meaning given above.

Preferably, X denotes $C_1$-$C_4$-alkyl, more preferably X denotes methyl, isopropyl or tert.-butyl.

| Reference-number | Chemical Name | Structure | CyO—D-Code |
|---|---|---|---|
| BIO1692 | (N,N-Diethyl-carbamic acid (2,3,6-Trimethyl)-cyclohexyl ester | 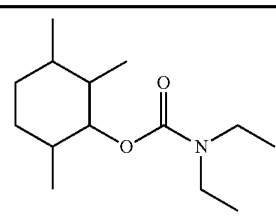 | BM202 |
| BIO1694 | Diethyl-carbamic acid 2-isopropyl-cyclohexyl ester | 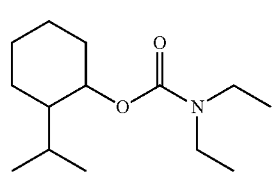 [SMILES: CCN(CC)C(=O)OC1CCCCC1C(C)C] | AK202 |

Most preferably A denotes

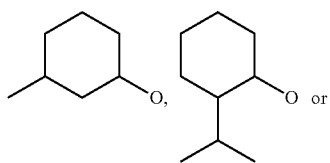O, 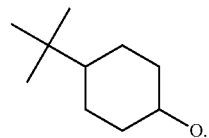O.

Particularly preferred cyclohexyl carbamates of formula (Carb-II-R1H), derived from monosubstituted cyclohexanols, are the following:

| Reference-number | Chemical Name | Structure | CyO—N-Code |
|---|---|---|---|
| BIO1825 | p-Tolyl-carbamic acid 3-methyl-cyclohexyl ester | 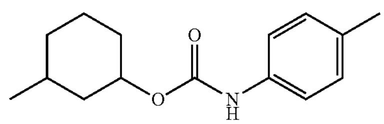 | AC38 |
| BIO1841 | Butyl-carbamic acid 2-isopropyl-cyclohexyl ester | 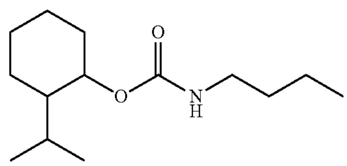 [SMILES: CCCCNC(=O)OC1CCCCC1C(C)C] | AK5 |
| BIO1824 | p-Tolyl-carbamic acid 2-isopropyl-cyclohexyl ester | 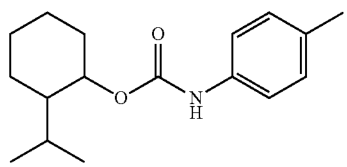 [SMILES: Cc1ccc(NC(=O)OC2CCCCC2C(C)C)cc1] | AK38 |
| BIO1744 | (2-Methoxy-phenyl)-carbamic acid 2-isopropyl-cyclohexyl ester | 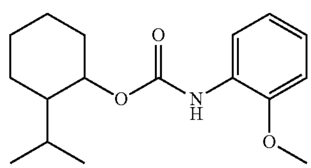 [SMILES: COc1ccccc1NC(=O)OC1CCCCC1C(C)C] | AK73 |
| BIO1690 | (2-Methyl-cyclohexyl)-carbamic acid 4-tert-butyl-cyclohexyl ester | 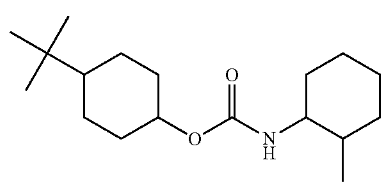 [SMILES: CC1CCCCC1NC(=O)OC1CCC(C(C)(C)C)CC1] | AX26 |
| BIO1707 | (4,4-Diethoxy-butyl)-carbamic acid 4-propyl-cyclohexyl ester | 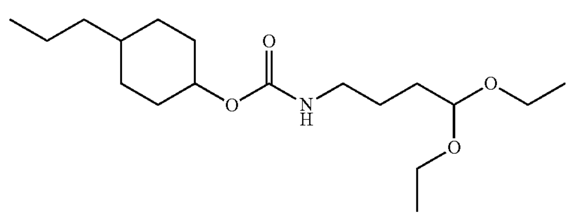 [SMILES: CCCC1CCC(OC(=O)NCCCC(OCC)OCC)CC1] | AJ121 |
| BIO1646 | (2-Hydroxy-phenyl)-carbamic acid 2-isopropyl-cyclohexyl ester | 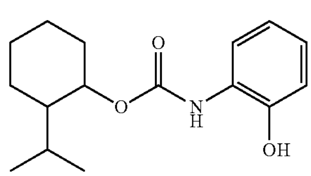 [SMILES: CC(C)C1CCCCC1OC(=O)Nc1ccccc1O] | AK111 |

-continued

| Reference-number | Chemical Name | Structure | CyO—N-Code |
|---|---|---|---|
| BIO1740 | Phenyl-carbamic acid 2-tert-butyl-cyclohexyl ester | 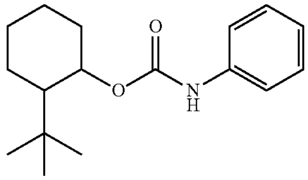 [SMILES: CC(C)(C)C1CCCCC1OC(=O)Nc1ccccc1] | AV35 |

The (preferred) compounds of formula (I) derived from monosubstituted cyclohexanols, in particular those explicitly listed above, were particularly active regarding the effects to be achieved in the context of the present invention.

In another preferred embodiment, preferred compounds of formulae (I), (Carb-I), (Carb-II) and (Carb-II-R1H), are those in which X and Y independently of one another denote C1-C4-alkyl or C2-C4-alkenyl and Z denotes hydrogen.

Such cyclohexyl carbamates are derived from disubstituted cyclohexanols, thus to compounds of formula (I) in which A denotes

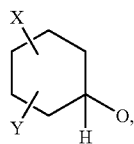

wherein X and Y have the meaning given above.

Preferably, X and Y independently of one another denote C1-C4-alkyl, more preferably methyl, isopropyl or tert.-butyl. In a preferred embodiment, X or Y denotes methyl.

More preferably, X and Y independently of one another denote methyl or isopropyl, most preferably A denotes

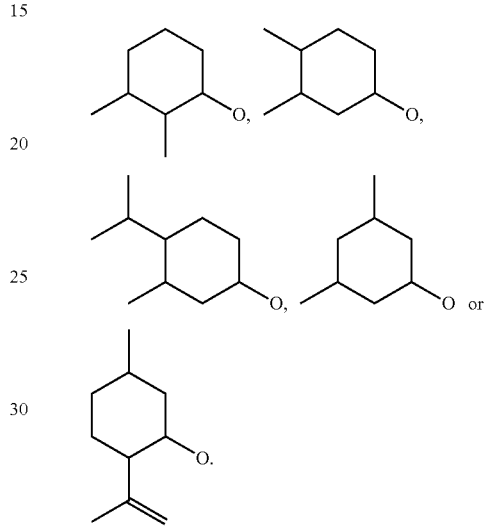

Particularly preferred cyclohexyl carbamates of formula (Carb-II-R1H), derived from disubstituted cyclohexanols, are the following:

| Reference-number | Chemical Name | Structure | CyO—N-Code |
|---|---|---|---|
| BIO1561 | Ethyl-carbamic acid 3,5-dimethyl-cyclohexyl ester | 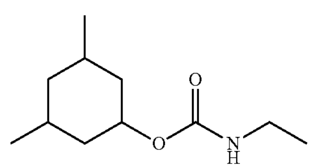 | BH2 |
| BIO1822 | p-Tolyl-carbamic acid 3,5-dimethyl-cyclohexyl ester | 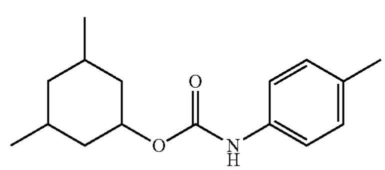 | BH38 |
| BIO1840 | Butyl-carbamic acid 3,5-dimethyl-cyclohexyl ester | 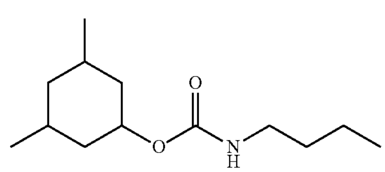 [SMILES: CCCCNC(=O)OC1CC(C)CC(C)C1] | BH5 |

-continued

| Reference-number | Chemical Name | Structure | CyO—N-Code |
|---|---|---|---|
| BIO1685 | Phenyl-carbamic acid 3,5-dimethyl-cyclohexyl ester | 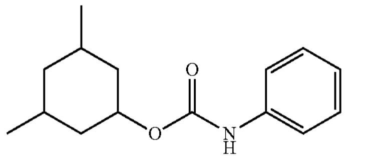 [SMILES: CC1CC(C)CC(OC(=O)Nc2ccccc2)C1] | BH35 |
| BIO1643 | (2-Hydroxy-phenyl)-carbamic acid 2,3-dimethyl-cyclohexyl ester | 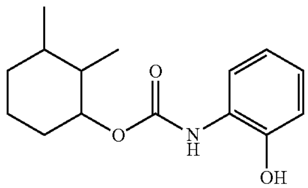 [SMILES: CC1CCCC(OC(=O)Nc2ccccc2O)C1C] | AZ111 |
| BIO1842 | Butyl-carbamic acid 2,3-dimethyl-cyclohexyl ester | 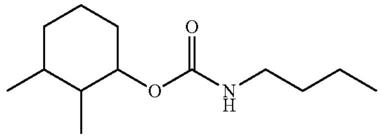 [SMILES: CCCCNC(=O)OC1CCCC(C)C1C] | AZ5 |
| BIO1615 | Butyl-carbamic acid 2-isopropenyl-5-methyl-cyclohexyl ester | 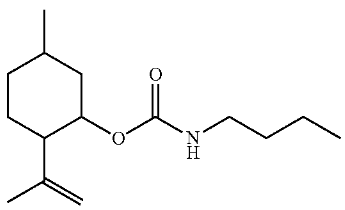 [SMILES: C=C(C)C1CCC(C)CC1OC(=O)NCCCC] | PK5 |
| BIO1551 | Ethyl-carbamic acid 2-isopropenyl-5-methyl-cyclohexyl ester | 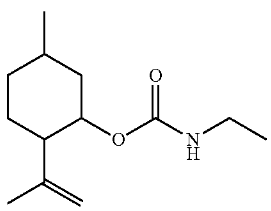 [SMILES: C=C(C)C1CCC(C)CC1OC(=O)NCC] | PK2 |

The (preferred) compounds of formula (I) derived from disubstituted cyclohexanols, in particular those explicitly listed above, were particularly active regarding the effects to be achieved in the context of the present invention.

In another preferred embodiment, preferred compounds of formulae (I), (Carb-I), (Carb-II) and (Carb-II-R1H) are those in which X, Y and Z independently of one another denote C1-C4-alkyl or C2-C4-alkenyl.

Such cyclohexyl carbamates are derived from trisubstituted cyclohexanols, thus to compounds of formula (I) in which A denotes

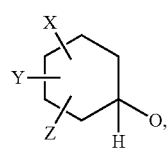

wherein X, Y and Z have the meaning given above.

Preferably, X, Y and Z independently of one another denote C1-C4-alkyl, more preferably methyl, isopropyl or tert.-butyl. In a preferred embodiment, at least one substituent of X, Y or Z denotes methyl.

More preferably, X, Y and Z independently of one another denote methyl or isopropyl, most preferably X, Y and Z each denote methyl, in particular A denotes

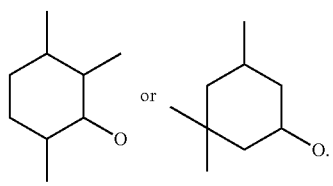

Also preferred cyclohexyl carbamates are derived from trisubstituted cyclohexanols are those wherein X denotes methyl and Y and Z together form a radical (a bridge) with 3 carbon atoms.

Among the compounds of formula (I) derived from bicyclic cyclohexanols, it was found that those wherein A denotes

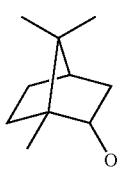

(i.e. borneyl or isoborneyl) were particularly active, in particular those of formula (Carb-II-R1H).

Particularly preferred cyclohexyl carbamates of formula (Carb-II-R1H), derived from trisubstituted cyclohexanols, are the following:

| Reference-number | Chemical Name | Structure | CyO—N-Code |
|---|---|---|---|
| BIO1701 | (2-Methoxy-phenyl)-carbamic acid 2,3,6-trimethyl-cyclohexyl ester | 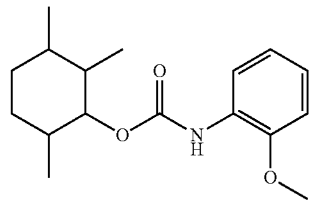 [SMILES: COc1ccccc1NC(=O)OC1C(C)CCC(C)C1C] | BM73 |
| BIO1617 | Butyl-carbamic acid 2,3,6-trimethyl-cyclohexyl ester | 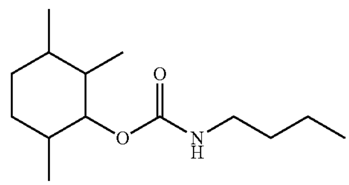 [SMILES: CCCCNC(=O)OC1C(C)CCC(C)C1C] | BM5 |
| BIO1850 | Hexyl-carbamic acid 3,3,5-trimethyl-cyclohexyl ester | 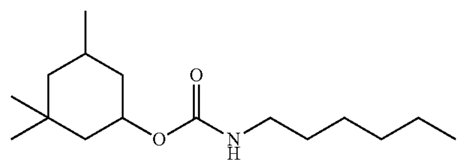 [SMILES: CCCCCCNC(=O)OC1CC(C)CC(C)(C)C1] | BU13 |
| BIO1703 | (2-Methoxy-phenyl)-carbamic acid 3,3,5-trimethyl-cyclohexyl ester | 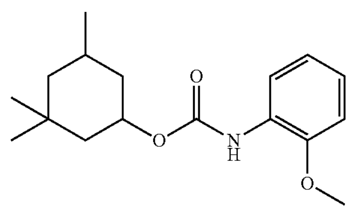 | BU73 |
| BIO1616 | Butyl-carbamic acid 3,3,5-trimethyl-cyclohexyl ester | 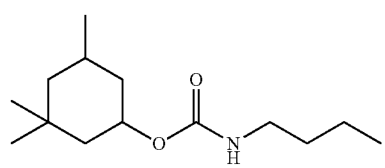 [SMILES: CCCCNC(=O)OC1CC(C)CC(C)(C)C1] | BU5 |
| BIO1844 | sec-Butyl-carbamic acid 3,3,5-trimethyl-cyclohexyl ester | 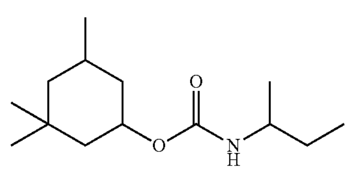 [SMILES: CCC(C)NC(=O)OC1CC(C)CC(C)(C)C1] | BU7 |
| BIO1572 | Ethyl-carbamic acid 3,3,5-trimethyl-cyclohexyl ester | 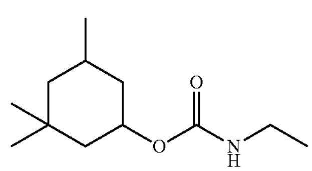 | BU2 |

-continued

| Reference-number | Chemical Name | Structure | CyO—N-Code |
|---|---|---|---|
| BIO1573 | Ethyl-carbamic acid 1,7,7-trimethyl-bicyclo[2.2.1]hept-2-yl ester | 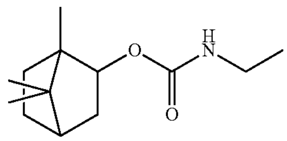 [SMILES: CCNC(=O)OC1CC2CCC1(C)C2(C)C] | TQ2 |
| BIO1574 | (3-Methoxy-propyl)-carbamic acid 3,3,5-trimethyl-cyclohexyl ester | 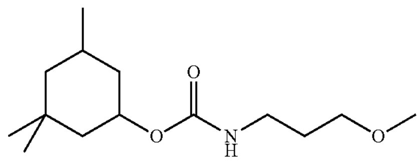 | BU109 |
| BIO1642 | (2-Hydroxy-phenyl)-carbamic acid 3,3,5-trimethyl-cyclohexyl ester | 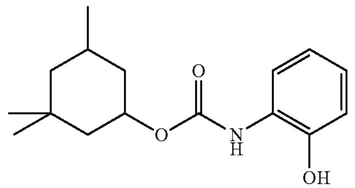 [SMILES: CC1CC(OC(=O)Nc2ccccc2O)CC(C)(C)C1] | BU111 |

The (preferred) compounds of formula (I) derived from trisubstituted cyclohexanols, in particular those explicitly listed above, were particularly active regarding the effects to be achieved in the context of the present invention.

The following compounds of formula (Carb-II-R1H) are particularly preferred since these were among the most active and effective compounds tested:

BIO1561, BIO1643, BIO1703, BIO1741, BIO1824, BIO1685, BIO1690, BIO1822, BIO1840, BIO1850, BIO1574, BIO1707, BIO1551 and BIO1615.

BIO1694 of formula (Carb-II) is also particularly preferred since it was one of the most active and effective compounds tested in the context of the present invention.

The compounds of formula (I) of the present invention may generally be obtained by procedures well-known in chemical synthesis. For example, reaction of

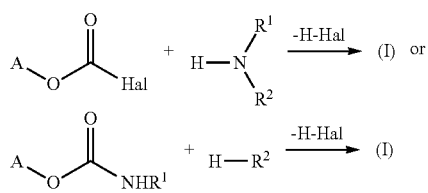

wherein

A, $R^1$ and $R^2$ denote a (preferred) radical as defined hereinabove, preferably $R^1$ denotes H, and Hal denotes a halide, preferably chloride or bromide.

In order to facilitate the dehydrohalogenation step and the formation of a compound of formula (I) it is preferred to carry out said reaction in the presence of a base, preferably a tertiary amine.

The preferred compounds of formula (I) wherein $R^1$ denotes H may preferably be obtained by reacting a cyclohexanol of formula A-H with a corresponding isocyanate O═C═N—$R^2$, as illustrated in the following reaction scheme:

A-H+O═C═N—$R^2$→ (I)

wherein A and $R^2$ denote a (preferred) radical as defined hereinabove. The reaction of the isocyanate and the cyclohexanol of formula A-H may be conducted in the absence or the presence of an inert solvent.

The present invention consequently relates to (preferably topical) cosmetic or pharmaceutical composition for lightening skin and/or hair, comprising (a) one, two or more (preferably of the preferred) compounds of formula (I) as defined herein and/or a cosmetically or pharmaceutically acceptable salt thereof, preferably in an amount having a lightening effect on skin and/or hair, and (b) one or more further active ingredients for skin and/or hair lightening suitable for cosmetic or pharmaceutical application which are not compounds of formula (I), preferably in an amount having a lightening effect on skin and/or hair.

Thus, in a (preferably topical) cosmetic or pharmaceutical composition according to the present invention for lightening skin and/or hair the amount of the one, two or more (preferably of the preferred) compounds of formula (I) as defined herein (component (a), above) alone and/or the amount of the one or more further active ingredients for skin and/or hair lightening (component (b), above) alone may not be sufficient to exhibit a lightening effect on skin and/or hair. However, the total amount, i.e. the sum, of components (a) and (b) in a composition according to the present invention is sufficient to exhibit a lightening effect on skin and/or hair.

As already indicated above, in preferred embodiments, the amount of the one, two or more (preferably of the preferred) compounds of formula (I) as defined herein (component (a), above) alone and/or the amount of the one or more further active ingredients for skin and/or hair lightening (component (b), above) alone in a composition according to the present invention are sufficient to exhibit a lightening effect on skin and/or hair.

A composition (preparation), preferably a topical composition, according to the present invention preferably contains one or more compounds of formula (I) (including all stereoisomers, enantiomers, diastereomers, cis/trans-isomers and epimers, without taking into account possible counterions) in a total amount of 0.001-30% by weight, more preferably 0.01-20% by weight, even more preferably 0.01-5% by weight, particularly preferably 0.05-3% by weight and most preferably 0.1-2% by weight, in each case based on the total weight of the preparation (composition).

In the context of the present invention an effective amount of compounds, preferably of the preferred compounds, of formula (I) relates to a total amount of one, two or more compounds, preferably of the preferred compounds, of formula (I) having a lightening effect on human skin and/or human hair.

The compounds of formula (I) can easily be incorporated in these concentrations in common cosmetic or dermatological formulations (preparations) such as pump sprays, aerosol sprays, creams, ointments, tinctures, lotions and the like.

The cosmetic, dermatological or pharmaceutical preparations according to the invention can be produced by conventional processes known per se, such that one or more compounds of formula (I) are incorporated into (topical) cosmetic, dermatological or pharmaceutical products which can have a conventional composition and which in addition to the effects mentioned hereinbefore or hereinafter can also be used for the treatment, care and cleansing of the skin or hair.

For use, topical cosmetic, dermatological or pharmaceutical preparations according to the invention or for use according to the invention comprising formula (I) are generally applied to the skin and/or hair in an adequate amount in the conventional manner for topical cosmetic, dermatological or pharmaceutical products.

As stated above, no mention or suggestion is made in the prior art of a cosmetic or therapeutic use of compounds of formula (I) as skin and/or hair lightening agents or of compounds of formula (I) having depigmenting action.

One area of application in this regard is the therapeutic treatment of melanin-induced pigmentation disorders such as hyperpigmentations (e.g. scar hyperpigmentations, posttraumatic drug-induced hyperpigmentations, post-inflammatory hyperpigmentations induced by phototoxic reactions, ephelides).

A cosmetic or pharmaceutical, preferably topical, preparation according to the present invention preferably contains as component (b) one or more active ingredients for skin and/or hair lightening selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, papaya extract, turmeric extract, mulberry extract, bengkoang extract, nutgrass extract, liquorice root extract or constituents concentrated or isolated therefrom, preferably glabridin or licochalcone A, artocarpus extract, extract of *rumex* and ramulus species, extracts of pine species (pinus), extracts of *vitis* species or stilbene derivatives isolated or concentrated therefrom, saxifrage extract, scutelleria extract and/or grape extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, papaya extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with one or more of the preferred or particularly preferred compounds of formula (I) according to the present invention. In addition, said preferred skin lighteners are readily available.

The skin and/or hair lightening activity of compounds of formula (I) is not based on tyrosinase inhibition.

A cosmetic or pharmaceutical, preferably topical, preparation according to the invention containing one or more active ingredients for skin and/or hair lightening selected from the above mentioned group of component (b) allows to achieve a more pronounced skin and/or hair lightening action which is, at least partly, based on synergistic effects.

Preparations according to the present invention including (a) one or more compounds of formula (I) and (b) one or more tyrosinase inhibitors have shown to exhibit particularly improved, in particular faster and/or stronger, activity, based on the modulation of two independent cellular mechanisms. In many cases a more than additive, often synergistic, lightening efficacy was observed.

Thus, in a preferred embodiment, preparations, preferably cosmetic preparations, according to the invention containing one or more compounds of formula (I) preferably comprise one or more active ingredients for skin and/or hair lightening which are tyrosinase inhibitors.

Preferred tyrosinase inhibitors are selected from the group consisting of kojic acid and skin and/or hair lightening resorcinol derivatives, preferably 4-alkylresorcinols, in particular 4-C3-C8-alkylresorcinols, and 4-(1-phenylethyl)1,3-dihydroxybenzene.

The total amount of the one or more further active ingredients for skin and/or hair lightening suitable for cosmetic or pharmaceutical application which are not compounds of formula (I), preferably selected from the aforementioned (preferred) group of further active ingredients for skin and/or hair lightening in the preparations according to the invention is preferably in the range of from 0.01 to 30 wt. %, more preferably in the range of from 0.01 to 20 wt. %, particularly preferably in the range of from 0.01 to 5 wt. %, in each case based on the total weight of the preparation.

In the context of the present text, in case a substance has skin and/or hair lightening properties as well as one or more further properties selected from the group consisting of antioxidant, anti-inflammatory, anti-irritant and/or exfoliating properties, said substance is considered as skin and/or hair lightening active of component (b), in particular for quantitative assessments.

For use in the conventional manner for cosmetics and pharmaceuticals, the compounds of formula (I) are applied to the skin and/or the hair in an adequate quantity. Particular advantages are offered here by preparations, preferably cosmetic and dermatological preparations, which contain one or more compounds of formula (I) and additionally act as a sun protection means, thereby providing a preparation which protects the hair and/or the skin from ultraviolet radiation.

Particular advantageous are cosmetic, dermatological and/or pharmaceutical preparations according to the invention which additionally include one or more sunscreen filters (UV absorbers, UV filters) and which thus act as both skin and/or lightening or age spot reducing agent and a sunscreen.

Preparations according to the invention in the cosmetics and pharmaceuticals area, which contain one or more compounds of formula (I), are advantageously combined with substances which absorb or reflect UV radiation, especially for cosmetic or skin-protecting purposes.

Cosmetic preparations preferred according to the invention can also contain anti-inflammatory and/or redness and/or itch ameliorating active ingredients. The compounds mentioned in WO 2005/123101 are advantageously used as anti-inflammatory or redness and/or itch ameliorating active ingredients.

In preferred embodiments anti-irritants are used in the preparations according to the present invention. Anti-irritants in this connection can be all anti-inflammatory active ingredients or active ingredients to relieve reddening and itching which are suitable for or commonly used in cosmetic (e.g. dermatological) and/or therapeutic applications. All substances which reduce the amount of histamine and cytokines, especially interleukins, prostaglandins and/or leukotrienes in cells and tissue are preferred.

The melanin production is often stimulated as a result of an inflammation, a process called postinflammatory hyperpigmentation. Skin insults that result in inflammation/irritation can induce postinflammatory hyperpigmentation. Among such insults are acne lesions, ingrown hairs, scratches, insect bites, and surfactant damage. One of the most common forms of postinflammatory hyperpigmentations is tanning following exposure to sunlight as a response to UV damage to skin. Although in the latter, there may not be visible erythema, histologically, such exposed skin has elevated inflammatory/irritant cell content, yielding a "subclinical" inflammatory/irritant process. Thus to prevent inflammation/irritation of the skin is beneficial regarding the inhibition of melanogenesis in the skin.

Preferred antioxidants within the meaning of the present text are substances which lower the amount of free radicals in cells and/or tissue.

Reactive oxygen species, such as superoxide and nitric oxide, generated in damaged skin (e.g. resulting from UV exposure) or released as by-products from inflammatory cells are known stimulators of melanogenesis in melanocytes. In such a case it is important to maintain the cellular redox by the suppression of reactive oxygen species, and to boost antioxidative defenses for the prevention of melanogenesis.

Thus, preferred preparations, preferably cosmetic preparations, according to the invention containing one or more compounds of formula (I) preferably additionally contain
one or more agents selected from the group of substances which absorb or reflect UV radiation, preferably for cosmetic purposes, in particular for skin- and/or hair-protecting purposes,
and/or
one or more agents selected from the group of anti-irritants and anti-inflammatory substances,
and/or
one or more agents selected from the group of antioxidants.

The total quantity of UV filter substances (UV absorbers) advantageously is in the range of from 0.01% to 40% by weight, preferably in the range of from 0.1% to 30% by weight, more preferably in the range of from 0.2 to 20% by weight, even more preferably in the range of from 0.5% to 15% by weight, in particular in the range of from 1.0 to 10.0% by weight, in each case based on the total weight of the preparation.

The total amount of anti-irritants (one or more compounds) and anti-inflammatory substances (one or more compounds) in the preparations according to the invention is preferably 0.01 to 20 wt. %, particularly preferably 0.03 to 10 wt. %, in particular 0.05 to 5 wt. %, based on the total weight of the preparation.

The total amount of antioxidants (one or more compounds) in the formulations according to the invention is preferably 0.01 to 20 wt. %, particularly preferably 0.05 to 10 wt. %, in particular 0.2 to 5 wt. %, based on the total weight of the formulation.

These preparations advantageously contain at least one UVA filter and/or at least one UVB filter and/or at least one inorganic pigment, so a light protection factor (sun protection factor, SPF) of 2 or higher (preferably of 5 or higher) is achieved.

Advantageous UV filters and inorganic light protection pigments are mentioned in WO 2005/123101. UV absorbers particularly suitable for combination are also mentioned in WO 2005/123101.

Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) such that the formulation according to the invention has a light protection factor of greater than or equal to 2 (preferably greater than or equal to 5). Such formulations according to the invention are particularly suitable for protecting the skin and hair.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Suitable UV filters are, for example, organic UV absorbers from the class comprising 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives, indole derivatives.

The compounds according to the invention or for use according to the invention having formula (I) are particularly preferably combined with water-soluble UV filters, in a preferred embodiment with phenylene bis-benzimidazyl tetrasulfonic acid disodium salt (Neo Heliopan®AP) and/or 2-phenylbenzimidazole sulfonic acid (Neo Heliopan®Hydro).

In addition, it is advantageous to combine compounds of formula (I) with active ingredients which penetrate into the skin and protect the skin cells from inside against sun light-induced damage such as skin ageing, skin inflammation and skin cancer. Respective ingredients, so called arylhydrocarbon receptor antagonists, are described in WO 2007/128723. Preferred is 2-benzylidene-5,6-dimethoxy-3,3-dimethylindan-1-one.

The UV filters cited below which can be used within the context of the present invention are preferred but naturally are not limiting.

UV filters which are preferably combined with one or more compounds of formula (I) in a preparation according to the present invention are selected from the group consisting of
- p-aminobenzoic acid
- p-aminobenzoic acid ethyl ester (25 mol) ethoxylated (INCI name: PEG-25 PABA)
- p-dimethylaminobenzoic acid-2-ethylhexyl ester
- p-aminobenzoic acid ethyl ester (2 mol) N-propoxylated
- p-aminobenzoic acid glycerol ester
- salicylic acid homomethyl ester (homosalates) (Neo Heliopan® HMS)
- salicylic acid-2-ethylhexyl ester (Neo Heliopan®OS)
- triethanolamine salicylate
- 4-isopropyl benzyl salicylate
- anthranilic acid menthyl ester (Neo Heliopan®MA)
- diisopropyl cinnamic acid ethyl ester
- p-methoxycinnamic acid-2-ethylhexyl ester (Neo Heliopan® AV)
- diisopropyl cinnamic acid methyl ester
- p-methoxycinnamic acid isoamyl ester (Neo Heliopan® E 1000)
- p-methoxycinnamic acid diethanolamine salt
- p-methoxycinnamic acid isopropyl ester
- 2-phenylbenzimidazole sulfonic acid and salts (Neo Heliopan® Hydro)
- 3-(4'-trimethylammonium) benzylidene bornan-2-one methyl sulfate
- beta-imidazole-4(5)-acrylic acid (urocanic acid)
- 3-(4'-sulfo)benzylidene bornan-2-one and salts
- 3-(4'-methyl benzylidene)-D,L-camphor (Neo Heliopan®MBC)
- 3-benzylidene-D,L-camphor
- N-[(2 and 4)-[2-(oxoborn-3-ylidene) methyl]benzyl]acrylamide polymer
- 4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb® HEB)
- benzylidene malonate polysiloxane (Parsol® SLX)
- glyceryl ethylhexanoate dimethoxycinnamate
- dipropylene glycol salicylate
- tris(2-ethylhexyl)-4,4',4"-(1,3,5-triazine-2,4,6-triyltriimino)tribenzoate (=2,4,6-trianilino-(p-carbo-2'-ethylhexyl-1'-oxy)-1,3,5-triazine) (Uvinul®T150)

Broadband filters which are preferably combined with one or more compounds of formula (I) in a preparation according to the present invention are selected from the group consisting of
- 2-ethylhexyl-2-cyano-3,3-diphenyl acrylate (Neo Heliopan®303)
- ethyl-2-cyano-3,3'-diphenyl acrylate
- 2-hydroxy-4-methoxybenzophenone (Neo Heliopan®BB)
- 2-hydroxy-4-methoxybenzophenone-5-sulfonic acid
- dihydroxy-4-methoxybenzophenone
- 2,4-dihydroxybenzophenone
- tetrahydroxybenzophenone
- 2,2'-dihydroxy-4,4'-dimethoxybenzophenone
- 2-hydroxy-4-n-octoxybenzophenone
- 2-hydroxy-4-methoxy-4'-methyl benzophenone
- sodium hydroxymethoxybenzophenone sulfonate
- disodium-2,2'-dihydroxy-4,4'-dimethoxy-5,5'-disulfobenzophenone
- phenol, 2-(2H-benzotriazol-2-yl)-4-methyl-6-(2-methyl-3 (1,3,3,3-tetramethyl-1-(trimethylsilyl)oxy)disiloxanyl)propyl)(Mexoryl®XL)
- 2,2'-methylene bis-(6-(2H-benzotriazol-2-yl)-4-1,1,3,3-tetramethylbutyl)phenol) (Tinosorb®M)
- 2,4-bis-[4-(2-ethylhexyloxy)-2-hydroxyphenyl]-1,3,5-triazine
- 2,4-bis-[{(4-(2-ethylhexyloxy)-2-hydroxy}phenyl]-6-(4-methoxyphenyl)-1,3,5-triazine (Tinosorb®S)
- 2,4-bis-[{(4-(3-sulfonato)-2-hydroxypropyloxy)-2-hydroxy}phenyl]-6-(4-methoxyphenyl)-1,3,5-triazine sodium salt
- 2,4-bis-[{(3-(2-propyloxy)-2-hydroxypropyloxy)-2-hydroxy}phenyl]-6-(4-methoxyphenyl)-1,3,5-triazine
- 2,4-bis-[{4-(2-ethylhexyloxy)-2-hydroxy}phenyl]-6-[4-(2-methoxyethyl carbonyl)phenylamino]-1,3,5-triazine
- 2,4-bis-[{4-(3-(2-propyloxy)-2-hydroxypropyloxy)-2-hydroxy}phenyl]-6-[4-(2-ethylcarboxyl)phenylamino]-1,3,5-triazine
- 2,4-bis-[{4-(2-ethylhexyloxy)-2-hydroxy}phenyl]-6-(1-methylpyrrol-2-yl)-1,3,5-triazine
- 2,4-bis-[{4-tris-(trimethylsiloxysilylpropyloxy)-2-hydroxy}phenyl]-6-(4-methoxyphenyl)-1,3,5-triazine
- 2,4-bis-[{4-(2"-methylpropenyloxy)-2-hydroxy}phenyl]-6-(4-methoxyphenyl)-1,3,5-triazine
- 2,4-bis-[{4-(1',1',1',3',5',5',5'-heptamethylsiloxy-2"-methylpropyloxy)-2-hydroxy}phenyl]-6-(4-methoxyphenyl)-1,3,5-triazine UV-A filters filters which are preferably combined with one or more compounds of formula (I) in a preparation according to the present invention are selected from the group consisting of
- 4-isopropyl dibenzoyl methane
- terephthalylidene dibornane sulfonic acid and salts (Mexoryl®SX)
- 4-t-butyl-4'-methoxydibenzoyl methane (avobenzone)/ (Neo Heliopan®357)
- phenylene bis-benzimidazyl tetrasulfonic acid disodium salt (Neo Heliopan®AP)
- 2,2'-(1,4-phenylene)-bis-(1H-benzimidazole-4,6-disulfonic acid), monosodium salt
- 2-(4-diethylamino-2-hydroxybenzoyl)benzoic acid hexyl ester (Uvinul® A Plus)
- indanylidene compounds in accordance with DE 100 55 940 (=WO 02/38537)

UV filters which are more preferably combined with one or more compounds of formula (I) in a preparation according to the present invention are selected from the group consisting of
- p-aminobenzoic acid
- 3-(4'-trimethylammonium) benzylidene bornan-2-one methyl sulfate
- salicylic acid homomethyl ester (Neo Heliopan®HMS)
- 2-hydroxy-4-methoxybenzophenone (Neo Heliopan®BB)
- 2-phenylbenzimidazole sulfonic acid (Neo Heliopan®Hydro)
- terephthalylidene dibornane sulfonic acid and salts (Mexoryl®SX)

4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan®303)
N-[(2 and 4)-[2-(oxoborn-3-ylidene) methyl]benzyl]acrylamide polymer
p-methoxycinnamic acid-2-ethylhexyl ester (Neo Heliopan®AV)
p-aminobenzoic acid ethyl ester (25 mol) ethoxylated (INCI name: PEG-25 PABA)
p-methoxycinnamic acid isoamyl ester (Neo Heliopan®E1000)
2,4,6-trianilino-(p-carbo-2'-ethylhexyl-1'-oxy)-1,3,5-triazine (Uvinul®T150)
phenol, 2-(2H-benzotriazol-2-yl)-4-methyl-6-(2-methyl-3 (1,3,3,3-tetramethyl-1-(trimethylsilyl)oxy)disiloxanyl)propyl)(Mexoryl®XL)
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb HEB)
3-(4'-methyl benzylidene)-D,L-camphor (Neo Heliopan®MBC)
3-benzylidene camphor
salicylic acid-2-ethylhexyl ester (Neo Heliopan®OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl)phenol) (Tinosorb®M)
phenylene bis-benzimidazyl tetrasulfonic acid disodium salt (Neo Heliopan®AP)
2,4-bis-[{(4-(2-ethylhexyloxy)-2-hydroxy}phenyl]-6-(4-methoxyphenyl)-1,3,5-triazine (Tinosorb®S)
benzylidene malonate polysiloxane (Parsol®SLX)
menthyl anthranilate (Neo Heliopan®MA)
2-(4-diethylamino-2-hydroxybenzoyl)benzoic acid hexyl ester (Uvinul® A Plus)
indanylidene compounds in accordance with DE 100 55 940 (=WO 02/38537).

Advantageous inorganic light protection pigments are finely dispersed metal oxides and metal salts which are also mentioned in WO 2005/123101. The total quantity of inorganic pigments, in particular hydrophobic inorganic micropigments in the finished cosmetic preparation according to the present invention is advantageously from 0.1 to 30% by weight, preferably 0.5 to 10.0% by weight, in each case based on the total weight of the preparation.

Furthermore, particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Steroidal anti-inflammatory substances of the corticosteroid type, such as e.g. hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004/047833, are preferred anti-itch ingredients in a composition according to the present invention. Alternatively, natural anti-inflammatory substances or substances to relieve reddening and itching can be used. Plant extracts, special highly active plant extract fractions and highly pure active substances isolated from plant extracts can be used. Particularly preferred are extracts, fractions and active substances from camomile, aloe vera, *commiphora* species, rubia species, echinacea species, willow, willowherb, oats, black and green tea, gingko, coffee, pepper, blackcurrant, tomato, vanilla, almonds, as well as pure substances such as inter alia bisabolol, apigenin-7-glucoside, boswellic acid, phytosterols, glycyrrhizinic acid, glabridin or licochalcone A.

In other preferred embodiments, a composition according to the present invention, comprises one or more actives providing a benefit for the skin, in particular skin irritation-reducing or skin-soothing agents, preferably selected from the group consisting of anti-inflammatory agents, compounds that alleviate itching and/or compounds that alleviate reddening which are suitable for cosmetic and/or dermatological applications, wherein the one or more actives are preferably selected from the groups consisting of:

steroidal anti-inflammatory substances of the corticosteroid type, in particular hydrocortisone, hydrocortisone derivatives such as hydrocortisone 17-butyrate, dexamethasone, dexamethasone phosphate, methylprednisolone or cortisone; and/or natural or naturally occurring anti-inflammatory mixtures of substances or mixtures of substances that alleviate reddening and/or itching, in particular extracts or fractions from camomile, Aloe vera, *Commiphora* species, *Rubia* species, willow, willow-herb, oats, *calendula*, arnica, St John's wort, honeysuckle, rosemary, *Passiflora incarnata*, witch hazel, ginger or Echinacea; preferably selected from the group consisting of extracts or fractions from camomile, Aloe vera, oats, *calendula*, arnica, honeysuckle, rosemary, witch hazel, ginger or Echinacea, and/or pure substances, preferably alpha-bisabolol, apigenin, apigenin-7-glucoside, gingerols, shogaols, gingerdiols, dehydrogingerdiones, paradols, natural or naturally occurring avenanthramides, preferably tranilast, avenanthramide A, avenanthramide B, avenanthramide C, non-natural or non-naturally occurring avenanthramides, preferably dihydroavenanthramide D, dihydroavenanthramide E, avenanthramide D, avenanthramide E, avenanthramide F, boswellic acid, phytosterols, glycyrrhizin, glabridin and licochalcone A; preferably selected from the group consisting of alpha-bisabolol, gingerols, shogaols, gingerdiols, dehydrogingerdiones, paradols, natural avenanthramides, non-natural avenanthramides, preferably dihydroavenanthramide D (as described in WO 2004/047833), boswellic acid, phytosterols, glycyrrhizin, and licochalcone A; and/or Preferably a preparation according to the present invention comprises one or more actives selected from the groups consisting of:

extracts or fractions from camomile, Aloe vera, oats, *calendula*, arnica, honeysuckle, rosemary, witch hazel, ginger or *Echinacea*; and/or alpha-bisabolol, gingerols, shogaols, gingerdiols, dehydrogingerdiones, paradols, natural avenanthramides, non-natural avenanthramides, preferably dihydroavenanthramide D, boswellic acid, phytosterols, glycyrrhizin, and licochalcone A; and/or

*urea*, hyaluronic acid, allantoin, panthenol, lanolin, alpha-hydroxy acids (preferably citric acid, lactic acid), vitamin E and derivatives (preferably tocopherol, tocopheryl acetate).

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of *Vanillosmopsis* (in particular *Vanillosmopsis erythropappa* or *Vanillosmopsis arborea*). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide ($CO_2$), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

The formulations according to the invention can also contain (additional) antioxidants or preservatives. All antioxidants which are suitable or commonly used for cosmetic (e.g. dermatological) and/or therapeutic applications can be used as antioxidants or preservatives.

Antioxidants as part of a preparation according to the present invention are preferably chosen from the group comprising amino acids (e.g. glycine, histidine, tyrosine, tryptophane) and derivatives thereof, imidazoles (e.g. urocanic acid) and derivatives thereof, peptides such as D,L-carnosine, D-carnosine, L-carnosine and derivatives thereof (e.g. anserine), carnitine, creatine, matrikine peptides (e.g. lysyl-threonyl-threonyllysyl-serine) and palmitoylated pentapeptides, carotenoids, carotenes (e.g. alphacarotene, beta-carotene, lycopene) and derivatives thereof, lipoic acid and derivatives thereof (e.g. dihydrolipoic acid), aurothioglucose, propyl thiouracil and other thiols (e.g. thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very small tolerated doses (e.g. pmol to μmol/kg), also (metal) chelators (e.g. alpha-hydroxy fatty acids, palmitic acid, phytic acid, lactoferrin, alpha-hydroxy acids (e.g. citric acid, lactic acid, malic acid), humic acid, bile acid, bile extracts, tannins, bilirubin, biliverdin, EDTA, EGTA and derivatives thereof), unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate, ascorbyl glucoside), tocopherols and derivatives (e.g. vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, e.g. alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids such as retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenium methionine), superoxide dismutase, stilbenes and derivatives thereof (e.g. stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, such as e.g. green tea, rooibos, honeybush, grape, rosemary, sage, melissa, thyme, lavender, olive, oats, cocoa, ginkgo, ginseng, liquorice, honeysuckle, *sophora, pueraria, pinus*, citrus, *Phyllanthus emblica* or St. John's wort, grape seeds, wheat germ, *Phyllanthus emblica*.

Also suitable are coenzymes, such as e.g. coenzyme Q10, plastoquinone, menaquinone, ubiquinols 1-10, ubiquinones 1-10 or derivatives of these substances.

If vitamin E and/or derivatives thereof are used as the antioxidant(s), it is advantageous to choose their concentrations from the range from 0.001 to 10 wt. %, based on the total weight of the formulation.

If vitamin A or vitamin A derivatives or carotenes or derivatives thereof are used as the antioxidant(s), it is advantageous to choose their concentrations from the range from 0.001 to 10 wt. %, based on the total weight of the formulation.

The present invention further relates to novel compounds of formula (Carb-II) or a cosmetically acceptable salt thereof

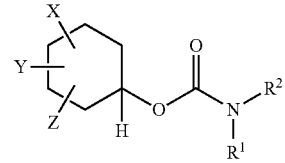

(Carb-II)

wherein $R^1$ denotes H, C1-C8-alkyl or C2-C8-alkenyl, $R^2$ denotes a radical having 1 to 14 carbon atoms, wherein $R^2$ consists of carbon, hydrogen and optionally oxygen and optionally silicon, wherein optionally $R^1$ and $R^2$ are covalently bonded to one another such that $NR^1R^2$ together denote a radical, selected from the group consisting of

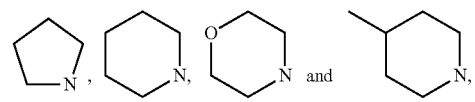

X, Y and Z independently of one another denote hydrogen, C1-C4-alkyl or C2-C4-alkenyl, wherein optionally two of the radicals X, Y and Z are covalently bonded to one another under formation of a bicyclic ring system, in such a bicyclic ring system two of the radicals X, Y and Z together preferably form a radical having 1 to 4 carbon atoms, preferably a hydrocarbon radical having 1 to 3 carbon atoms, wherein the compound of formula (Carb-II) contains a maximum number of 24 carbon atoms and has a molecular weight of at most 500 g/mol, preferably a molecular weight of at most 450 g/mol, with the proviso that the following compounds of formula (Carb-II) or a cosmetically acceptable salt thereof are excluded:

(i) menthyl-carbamates of formula (M-X)

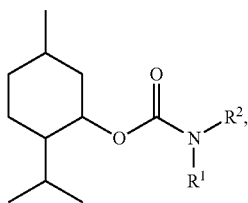

(M-X)

wherein $R^1$ and $R^2$ have the meaning given above, (ii) compounds of formula (Carb-II-R1H)

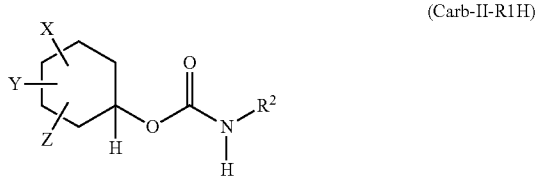

(Carb-II-R1H)

in which $R^2$ denotes phenyl or naphthyl, (iii) compounds of formula (Carb-II) in which X, Y, and Z each denote H, (iv) compounds of formula (Carb-II-R1H) wherein two of the radicals X, Y and Z are covalently bonded to one another under formation of a bicyclic ring system and wherein $R^2$ contains one or both of the following groups: —COOH and/ or =CH2, and (v) compounds known from the prior art of the formulae given above.

For the sake of clarity, it is noted that menthyl-carbamates of formula (M-X) and of formula (M-H) include all stereoisomeric forms of the carbamates of formula (M-X) and of formula (M-H), i.e. the menthyl-, neomenthyl-, isomenthyl- and neoisomenthylcarbamates, including their respective enantiomeric forms.

Preferably, the compounds of formula (I), in particular the novel compounds of formula (Carb-II) and more particularly of formula (Carb-II-R1H), are skin and/or hair lightening actives (in accordance with the definition and preferred embodiments given above).

Preferably, from the compounds according to the present invention additionally the following compounds and their cosmetically acceptable salts are excluded:

compounds of formula (Carb-II-R1H), preferably of formula (Carb-II), in which $R^2$ is 3-Me-phenyl, biphenyl, p-hydroxyphenyl, p-carboxyphenyl, methyl, and compounds of formula (Carb-II-R1H) in which $R^2$ contains one, several or all of the following groups:
—COOH in alpha-position of N,
=CH2,
carbon-carbon triple bond,
—COOR in alpha- or beta-position of N, wherein R is a C1-C4-alkyl-radical,
—O(CO)-Ph in alpha-position of N.

The (particularly) preferred compounds of formula (I) of the present invention are preferably used in the preferred compositions indicated hereinbefore or hereinafter.

The (particularly) preferred aspects and embodiments mentioned hereinbefore or hereinafter relating to compounds of formula (I) or compositions (preparations) comprising one or more compounds of formula (I) according to the present invention also apply to (particularly) preferred aspects and embodiments, uses and methods in accordance with the present invention.

The present invention further relates to a method for the cosmetic lightening skin and/or hair comprising the following step:

application, preferably topical application, of a cosmetically effective amount of a compound of formula (I) or a cosmetically acceptable salt of a compound of formula (I) or a mixture containing two or more of these compounds or the salts thereof as defined herein or of a cosmetic composition as defined herein.

A further aspect of the present invention is the use of a compound of formula (I) or a pharmaceutically acceptable salt of a compound of formula (I) or a mixture containing two or more of these compounds or the salts thereof as defined herein for the preparation of a pharmaceutical, preferably topical, composition for lightening skin and/or hair, in particular for the treatment of hyperpigmentation.

The present invention further relates to a compound of formula (I) or a pharmaceutically acceptable salt of a compound of formula (I) or a mixture containing two or more of these compounds or the salts thereof as defined herein as a drug, preferably as active for lightening skin and/or hair, in particular as active for the treatment of hyperpigmentation.

The present invention further relates to a pharmaceutical composition comprising a pharmaceutically active amount of one or more compounds of formula (I) as defined herein, preferably for lightening skin and/or hair, in particular for the treatment of hyperpigmentation.

Further, the present invention also relates to a method for lightening skin and/or hair, preferably for treating hyperpigmentation, comprising the following step:

application, preferably topical application, of a pharmaceutically effective amount of a compound of formula (I) or a pharmaceutically acceptable salt of a compound of formula (I) or a mixture containing two or more of these compounds or the salts thereof as defined herein or of a pharmaceutical composition as defined herein.

The present invention also relates to a cosmetic or therapeutic method for lightening human skin and/or hair, comprising the step of provision of one or more compounds of formula (I) or a cosmetically or pharmaceutically acceptable salt thereof, or of a cosmetic or pharmaceutical composition according to the present invention, application of the one or more compounds of formula (I) or of the composition to human skin and/or hair in an effective amount, said application preferably remaining for at least 10 minutes, more preferably for at least 30 minutes, most preferably for at least 60 minutes, on said skin and/or hair ("leave-on product").

Substances and auxiliaries which may additionally contain a preparation according to the invention containing one or more compounds of formula (I) are, for example:

preservatives, in particular those described in US 2006/0089413, antimicrobial agents, such as e.g. antibacterial agents or agents to treat yeast and mold, in particular those described in WO 2005/123101, antiacne and sebum reducing agents, in particular those described in WO 2008/046791, compounds against ageing of the skin, in particular those described in WO 2005/123101 and US 2009/0232915, anti-cellulite agents, in particular those described in WO 2007/077541, anti-dandruff agents, in particular those described in WO 2008/046795, anti-irritants (ant-inflammatory agents, irritation-preventing agents, irritation-inhibiting agents), in particular those described in WO 2007/042472 and US 2006/0089413, antioxidants, in particular those described in WO 2005/123101, carrier materials, in particular those described in WO 2005/123101, chelating agents, in particular those described in WO 2005/123101, deodorizing agents and antiperspirants, in particular those described in WO 2005/123101, moisture regulators (moisture-donating agents, moisturizing substance, moisture-retaining substances), in particular those described in WO 2005/123101, osmolytes, in particular those described in WO 2005/123101, compatible solutes, in particular those described in WO 01/76572 and WO 02/15868, proteins and protein hydrolysates, in particular those described in WO 2005/123101 and WO 2008/46676, skin-lightening agents, in particular those described in WO 2007/110415, cooling agents, in particular those described in WO 2005/123101, skin-cooling agents, in particular those described in WO 2005/123101, skin warming agents, in particular those described in WO 2005/123101, UV-absorbing agents, in particular those described in WO 2005/123101, UV filters, in particular those described in WO 2005/123101, benzylidene-beta-dicarbonyl compounds in accordance with WO 2005/107692 and alpha-benzoyl-cinnamic acid nitriles in accordance with WO 2006/015954, insect repellents, in particular those described in WO 2005/123101, plant parts, plant extracts, in particular those described in WO 2005/123101, vitamins, in particular those described in WO 2005/123101, emulsifiers, in particular those described in WO 2005/123101, gelling agents, in particular those described in WO 2005/123101, oils in particular those described in WO 2005/123101, waxes in particular those described in WO 2005/123101, fats in particular those described in WO 2005/123101, phospholipids, in particular those described in WO 2005/123101, saturated fatty acids and mono- or polyunsaturated fatty acids and α-hydroxy acids and polyhydroxy-fatty acids and esters of saturated and/or unsaturated branched and/or unbranched alkane carboxylic acids, in particular those described in WO 2005/123101, surface-active substances (surfactants), in particular those described in WO 2005/123101, skin repair agents comprising cholesterol and/or fatty acids and/or ceramides and/or pseudoceramides, in particular those described in WO 2006/053912, dyestuffs and colorants and pigments, in particular those described in WO 2005/123101, aroma chemicals and flavors and fragrances, in particular those described in S. Arctander, Perfume and Flavor Chemicals, private publishing house, Montclair, N.J., 1969 and Surburg, Panten, Common Fragrance and Flavor Materials, 5th Edition, Wiley-VCH, Weinheim 2006, preferably those explicitly mentioned in US 2008/0070825, alcohols and polyols, in particular those described in WO 2005/123101, organic solvents, in particular those described in WO 2005/123101, silicones and silicone oils and silicone derivatives in particular those described in WO 2008/046676, virucides, abrasives, astringents, antiseptic agents, antistatics, binders, buffers, cell stimulants, cleansing agents, care agents, depilatory agents, softeners, enzymes, essential oils, in particular those described in US 2008/0070825, fibres, film-forming agents (e.g. polyvinyl pyrrolidones, chitosan or chitosan derivatives), fixatives, foam-forming agents, foam stabilizers, substances for preventing foaming, foam boosters, gel-forming agents, hair growth activators, hair growth inhibitors, hair care agents, hair-setting agents, hair-straightening agents, hair-smoothening, bleaching agents, strengthening agents, stain-removing agents, optically brightening agents, impregnating agents, dirt-repellent agents, friction-reducing agents, lubricants, opacifying agents, plasticizing agents, covering agents, polish, gloss agents, polymers in particular those described in WO 2008/046676, powders, peptides, mono-, di- and oligosaccharides, re-oiling agents, abrading agents, skin-soothing agents, skin-cleansing agents, skin care agents, skin-healing agents, skin-protecting agents, skin-softening agents, skin-smoothing agents, nourishing agents, skin-warming agents, stabilizers, detergents, fabric conditioning agents, suspending agents, thickeners, yeast extracts, algae or microalgae extracts, animal extracts, liquefiers, color-protecting agents, and electrolytes.

In a preferred embodiment, a preparation according to the present invention comprises one or more compounds of formula (I) and one or more hair growth modulating actives, in particular one or more agents to stimulate hair growth.

Preferred agents to stimulate hair growth are selected from the group consisting of pyrimidine derivatives, in particular 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids, in particular caffeine, theobromine and theophylline and derivatives thereof, quercetin and derivatives, dihydroquercetin (taxifolin) and derivatives, potassium channel openers, anti-androgenic agents, synthetic or natural 5-reductase inhibitors, nicotinic acid esters, in particular tocopheryl nicotinate, benzyl nicotinate and C1-C6 alkyl nicotinate, proteins, in particular the tripeptide Lys-Pro-Val, diphencypren, hormones, finasteride, dutasteride, flutamide, bicalutamide, pregnane derivatives, progesterone and its derivatives, cyproterone acetate, spironolactone and other diuretics, calcineurin inhibitors, in particular FK506 (Tacrolimus, Fujimycin) and its derivatives, Cyclosporin A and derivatives thereof, zinc and zinc salts, polyphenols, procyanidins, proanthocyanidins, phytosterols, in particular betasitosterol, biotin, eugenol, (±)-beta-citronellol, panthenol, glycogen, in particular from mussels, hydrolysates from rice, hydrolysates from wheat, and extracts from microorganisms, algae, microalgae or plants and plant parts, in particular of the genera dandelion (*Leontodon* or *Taraxacum*), *Orthosiphon, Vitex, Coffea, Paullinia, Theobroma, Asiasarum, Cucurbita* or *Styphnolobium, Serenoa repens* (saw palmetto), *Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis*, licorice, grape, apple, barley and hops.

In another preferred embodiment, a preparation according to the present invention comprises one or more compounds of formula (I) and one or more agents to inhibit hair growth.

Preferred agents to inhibit hair growth are selected from the group consisting of activin, activin derivatives or activin agonists, ornithine decarboxylase inhibitors, in particular alpha-difluoromethylornithine or pentacyclic triterpenes, in particular ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, and extracts from microorganisms, algae, microalgae or plants and plant parts, in particular of the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* and *Gymnema sylvestre*.

Also advantageous are preparations according to the invention which are administered orally, for example in the form of tablets (for example film tablets), coated tablets, capsules (for example gelatin capsules), granulates, juices, solutions emulsions, micro emulsions, sprays or products which can be consumed orally in another form, or in the form of food, which, because of the compound(s) contained therein of formula (I) bring about "beauty from inside".

The following osmolytes may be a component of a preparation according to the invention: sugar alcohols (myo-inositol, mannitol, sorbitol), quaternary amines such as taurine, choline, betaine, betaine glycine, ectoine, diglycerol phosphate, phosphorylcholine, glycerophosphorylcholines, amino acids such as glutamine, glycine, alanine, glutamate, aspartate or proline, phosphatidylcholine, phosphatidylinositol, inorganic phosphates, and polymers of the cited compounds such as proteins, peptides, polyamino acids and polyols. Preferred osmolytes, which may be a component of a preparation according to the invention, are diglycerol phosphate and/or ectoine.

Preferred cosmetics carrier materials, which may be a component of a preparation according to the invention, are solid or liquid at 25° C. and 1013 mbar (including highly viscous substances).

Preferred liquid carrier substances, which may be a component of a preparation according to the invention are selected from the group consisting of glycerol, 1,2-propylene glycol, 1,2-butylene glycol, 1,3-butylene glycol, 1,2-pentanediol, 1,2-hexanediol, 1,2-octanediol, 1,2-decanediol, ethanol, water and mixtures of two or more of said liquid carrier materials with water. Optionally, these preparations according to the invention may be produced using preservatives, solubilizers or antioxidants.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

Furthermore, the preparations according to the invention may be present in encapsulated form, these preferably being encapsulated with a solid covering material, which is preferably selected from starches, degraded or chemically or physically modified starches (in particular dextrins and maltodexterins), gelatins, gum arabic, agar-agar, ghatti gum, gellan gum, modified and non-modified celluloses, pullulan, curdlan, carrageenans, alginic acid, alginates, pectin, inulin, xanthan gum and mixtures of two or more of said substances.

The solid covering material is preferably selected from gelatin (preferred are pork, beef, chicken and/or fish gelatins and mixtures thereof, preferably comprising at least one gelatin with a bloom value of greater than or equal to 200, preferably with a bloom value of greater than or equal to 240), maltodextrin (preferably obtained from maize (corn), wheat, tapioca or potato, preferred maltodextrins have a DE value of 10-20), modified cellulose (for example cellulose ether), alginates (for example Na-alginate), carrageenan (beta-, iota-, lambda- and/or kappa carrageenan), gum arabic, curdlan and/or agar-agar. Gelatin is preferably used, in particular, because of its good availability in different bloom values. Particularly preferred, especially for oral use are seamless gelatin or alginate capsules, the covering of which dissolves very rapidly in the mouth or bursts when chewing. Production may take place, for example, as described in EP 0 389 700, U.S. Pat. Nos. 4,251,195, 6,214,376, WO 03/055587 or WO 2004/050069.

Preferred cosmetic, dermatological or pharmaceutical preparations according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, in particular as defined above, compared to rinse-off products, so that the skin and/or hair lightening action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, after-sun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

It is also advantageous to administer the compounds having formula (I) in encapsulated form, e.g. in gelatine, wax materials, liposomes or cellulose capsules.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99 wt. %, preferably 10 to 80 wt. %, based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99 wt. %, preferably 5 to 80 wt. %, based on the total weight of the preparation.

The one or more substances with a physiological cooling effect (cooling agents), which can be used in combination with one or more compounds of formula (I) according to the invention, are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (I-menthoxy)-2-methyl-1,2-propandiol, I-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy)acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or N$^{\alpha}$-(menthanecarbonyl)glycmethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005/049553, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (I-(–)-isopulegol, I-(–)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840, further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2 033 688 A2).

The or the plurality of substances with a physiological cooling effect, which can be used in combination with one or more compounds of formula (I) according to the invention, are in particular preferably substances, which at least substantially cause a physiological cooling effect. Such preferred substances are: menthylethers (for example (I-menthoxy)-1,2-propandiol, (I-menthoxy)-2-methyl-1,2-propandiol), polar menthylesters (for example menthyllacetates, L-menthyl-L-lactate, L-menthyl-D-lactate, menthyl-(2-methoxy)acetate, menthyl-(2-methoxyethoxy)acetate, menthylpyroglutamate), menthylcarbonates (for example menthylpropyleneglycolcarbonate, menthylethyleneglycolcarbonate, menthylglycerolcarbonate), the semi-esters of menthols with a dicarboxylic acid or derivates thereof (for example mono-menthylsuccinate, mono-menthylglutarate, mono-menthylmalonate, O-menthyl succinic acid ester-N,N-(dimethyl)amide, O-menthyl succinic acid esteramide), not according to the invention, menthane carboxylic acid amides (for example menthane carboxylic acid-N-ethylamide [WS3], N$^{\alpha}$-(menthanecarbonyl)glycmethylester [WS5], menthane carboxylic acid-N-(4-cyanophenyl)amide, menthane carboxylic acid-N-(alkoxyalkyl)amides), menthone derivatives (for example L-menthone glycerol ketal), 2,3-dimethyl-2-(2-propyl)-butyric acid derivates (for example 2,3-dimethyl-2-(2-propyl)-butyric acid-N-methylamide), pyrrolidone derivatives of cycloalkyldione derivatives (for example 3-methyl-2(1-pyrrolidinyl)-2-cyclopentene-1-one) or tetrahydropyrimidine-2-ones (for example iciline or related compounds, which are described in WO 2004/026840), 1R,2S,5R)—N-(4-Methoxyphenyl)-5-methyl-2-(1-isopropyl)cyclohexane-carboxamide [WS12], L-Menthyl N-methyl oxamate, L-menthyl N-ethyl oxamate (as described in EP 2 033 688).

The total quantity of substances having a physiological cooling effect (one or more compounds) in the preparations according to the invention preferably is in the range of from 0.05-5% by weight, more preferably in the range of from 0.1-3% by weight, in particular in the range of from 0.25-1.5% by weight, in each case based on the total weight of the cosmetic or pharmaceutical preparation.

Components which cause a hot, sharp, tingly or prickly feeling on the skin or on the mucous membranes, in particular flavours with a heat-producing effect and/or sharp tasting compounds (sharp substances) which may, apart from one or more compounds of formula (I), be a component of a preparation according to the invention, are mentioned in WO 2005/123101.

Further, combinations with compounds which reduce the hypersensitivity of skin nerves based on their action as TRPV1 antagonists, e.g. trans-4-tert-butyl cyclohexanol (as described in WO 2009/087242), or indirect modulators of TRPV1 by an activation of the μ-receptor, e.g. acetyl tetrapeptide-15, are preferred.

The following anti-cellulite actives may be a component of a (preferably topical) preparation, preferably a cosmetic preparation, according to the invention: lipolysis stimulators like xanthines, in particular caffeine, extracts containing caffeine, or beta-adrenergic receptor agonists, for example synephrine and derivatives, and agents encouraging the activity of anti-cellulite agents, for example agents which stimulates and/or depolarises C nerve fibres such as capsaicin or vanillyl-nonylamid and derivatives thereof or extracts containing one or more of these substances like extracts obtainable from various species of the genus *Capsicum* (such as *Capsicum annum*), and compounds stimulating the microcirculation or draining, preferably selected from the group consisting of butcher's broom extract or its active component ruscogenin, horse chestnut extract or its active component escin, ivy extract and/or pineapple extract, (and) L-carnitine, coenzym A, isoflavonoides, soy extracts, conjugated linoleic acid (CLA). Preferably, anti-cellulite actives as a component of a preparation according to the invention are selected from the group consisting of caffeine, synephrine and/or L-carnitine.

Preferred preparations, preferably cosmetic preparations, according to the invention containing one or more compounds of formula (I) preferably additionally contain one or more active ingredients which prevent a breakdown of the connective tissue. Active ingredients are advantageous here which inhibit matrix-metallo-proteinases (MMPs). These enzymes are in a position to break down macromolecules of the extra-cellular matrix (ECM)/of the connective tissue, also including the collagens, proteolytically. In particular the matrix-metallo-proteinase-1 (MMP-1), matrix-metallo-proteinase-2 (MMP-2) and matrix-metallo-proteinase-9 (MMP-9) are responsible for the breakdown of the connective tissue of the skin. An inhibition of MMPs is possible, for example, by the addition of ursolic acid, retinyl palmitate, propyl gallate, precocenes, 6-hydroxy-7-methoxy-2,2-dimethyl-1 (2H)-benzopyran, 3,4-dihydro-6-hydroxy-7-methoxy-2,2-dimethyl-1(2H)-benzopyran. An addition of peptides, which inhibit MMPs, to preparations according to the invention, is also advantageous to inhibit MMPs. Proteins or glycoproteins from soya and hydrolysed proteins from rice, pea or lupine also inhibit MMPs and are therefore a suitable addition. A combination with a plant extract, which inhibits MMPs is also advantageous. To be mentioned here by way of example is an extract from shitake mushrooms. The combination with extracts from the leaves of the Rosaceae family, sub-family Rosoideae, is also advantageous. Quite particularly advantageous is the use of blackberry leaf extract, in particular as described in WO 2005/123101 A1.

MMP inhibitors to be preferably used in combination in the scope of the present invention are retinyl palmitate, propyl gallate, precocenes, 6-hydroxy-7-methoxy-2,2-dimethyl-1 (2H)benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsulfonylfluoride, collhibin (company Pentapharm; INCI: hydrolysed rice protein), oenotherol (company Soliance; INCI: propylene glycol, aqua, Oenothera biennis root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and *lentinus edodes* extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and numerous further plant extracts, which are listed in WO 02/069992 (see table 1-12 there).

In order to counteract the breakdown of the connective tissue, the combination of active ingredients, which encourage the formation of collagen in the tissue (collagen stimulants), is furthermore advantageous in preferred cosmetic preparations according to the invention containing one or more compounds of formula (I). Individual substances frequently used to increase collagen synthesis are, for example, ingredients such as ascorbic acid and their derivatives, retinol and derivatives of retinol or plant extracts such as, for example, extracts of aloe and centella species. Moreover peptidic materials and their derivatives, such as, for example, carnitine, carnosine, creatine, matrikine peptides (e.g. lysylthreonyl-threonyl-lysyl-serine) and further peptidic structures such as palmitoylated pentapeptides (for example matrixyl/company Sederma) or the oligopeptide with the trade name Vincipeptide (company Vincience/France) are also included in the frequently used active ingredients increasing collagen synthesis. Furthermore, compounds such as asiatic acid, madecassic acid, madecassoside, asiaticoside, extracts of Centella asiatica, niacinamide, astaxanthine, glucans, for example from yeast and oats, soya extracts and soya isoflavones such as genistein and daidzein, rutin, chrysin, morin, betel nut alkaloids, forskolin, betulinic acid, extracts of *Plantago* species, TGF-beta, extracts from *Ginkgo biloba*, glutamine and glycolic acid are also used as collagen synthesis stimulators. Particularly preferred here is the addition of a combination of aloe vera extract, raspberry extract and magnesium ascorbyl phosphate.

Formulations according to the invention, in particular dermatological formulations, can also advantageously contain dyes and/or coloured pigments, particularly if they are intended for use in the area of decorative cosmetics. The dyes and coloured pigments can be selected from the corresponding positive list in the German cosmetics ordinance or the EU list of cosmetic colorants. In most cases they are identical to the dyes approved for foodstuffs. Advantageous coloured pigments are for example titanium dioxide, mica, iron oxides (e.g. $Fe_2O_3$ $Fe_3O_4$, FeO(OH)) and/or tin oxide. Advantageous dyes are for example carmine, Berlin blue, chromium oxide green, ultramarine blue and/or manganese violet.

If the topical formulations according to the invention are intended for use in the facial area, it is convenient to choose as the dye one or more substances from the following group: 2,4-dihydroxyazobenzol, 1-(2'-chloro-4'-nitro-1'-phenylazo)-2-hydroxynaphthalene, Ceres red, 2-(4-sulfo-1-naphthylazo)-1-naphthol-4-sulfonic acid, calcium salt of 2-hydroxy-1,2'-azonaphthalene-1'-sulfonic acid, calcium and barium salts of 1-(2-sulfo-4-methyl-1-phenylazo)-2-naphthyl carboxylic acid, calcium salt of 1-(2-sulfo-1-naphthylazo)-2-hydroxynaphthalene-3-carboxylic acid, aluminium salt of 1-(4-sulfo-1-phenylazo)-2-naphthol-6-sulfonic acid, aluminium salt of 1-(4-sulfo-1-naphthylazo)-2-naphthol-3,6-disulfonic acid, 1-(4-sulfo-1-naphthylazo)-2-naphthol-6,8-disulfonic acid, aluminium salt of 4-(4-sulfo-1-phenylazo)-1-(4-sulfophenyl)-5-hydroxypyrazolone-3-carboxylic acid, aluminium and zirconium salts of 4,5-dibromofluorescein, aluminium and zirconium salts of 2,4,5,7-tetrabromofluorescein, 3',4',5',6'-tetrachloro-2,4,5,7-tetrabromofluorescein and its aluminium salt, aluminium salt of 2,4,5,7-tetraiodofluorescein, aluminium salt of quinophthalone disulfonic acid, aluminium salt of indigo disulfonic acid, red and black iron oxide (Colour Index Number (CIN): 77491 (red) and 77499 (black)), iron oxide hydrate (CIN: 77492), manganese ammonium diphosphate and titanium dioxide.

Also advantageous are oil-soluble natural dyes, such as e.g. paprika extracts, β-carotene or cochineal.

Also advantageous within the meaning of the present invention are dermatological formulations containing pearlescent pigments. The types of pearlescent pigment listed below are particularly preferred:
1. Natural pearlescent pigments, such as e.g.
    "pearl essence" (guanine/hypoxanthine mixed crystals obtained from fish scales) and
    "mother of pearl" (ground mussel shells)
2. Monocrystalline pearlescent pigments such as e.g. bismuth oxychloride (BiOCl)
3. Layered substrate pigments: e.g. mica/metal oxide The basis for pearlescent pigments is formed for example by powdered pigments or castor oil dispersions of bismuth oxychloride and/or titanium dioxide and bismuth oxychloride and/or titanium dioxide on mica. The lustre pigment listed under CIN 77163, for example, is particularly advantageous.

The list of cited pearlescent pigments is naturally not intended to be limiting. Advantageous pearlescent pigments within the meaning of the present invention are obtainable in many ways known per se. For example, substrates other than mica can be coated with other metal oxides, such as e.g. silica and the like. $SiO_2$ particles coated with $TiO_2$ and $Fe_2O_3$ ("Ronaspheres"), for example, which are sold by Merck and are particularly suitable for the optical reduction of fine lines, are advantageous.

It can also be advantageous to dispense altogether with a substrate such as mica. Iron pearlescent pigments, which are produced without the use of mica, are particularly preferred. Such pigments are available from BASF, for example, under the trade name Sicopearl Copper 1000.

Particularly advantageous also are special effect pigments, which are available from Flora Tech under the trade name Metasomes Standard/Glitter in various colours (yellow, red, green, blue). Here the glitter particles are mixed with various auxiliary substances and dyes (for example the dyes with CIN 19140, 77007, 77289, 77491).

The dyes and pigments can be present both individually and mixed together and coated with one another, wherein different colour effects can generally be obtained by means of varying coating thicknesses. The total amount of dyes and colouring pigments is advantageously chosen from the range from e.g. 0.1 wt. % to 30 wt. %, preferably 0.5 to 15 wt. %, in particular 1.0 to 10 wt. %, based in each case on the total weight of the (cosmetic) formulations.

A combination with (metal)-chelating agents may also be advantageous in some preparations. (Metal)-chelating agents to be preferably used are the compounds mentioned in WO 2005/123101.

The one or more compounds of formula (I) may advantageously be used, in particular, in cosmetic and dermatological preparations in combination with insect repellents such as, for example, DEET, IR 3225, Dragorepel™ (Symrise GmbH & Co. KG).

The one or more compounds of formula (I) can advantageously be used in particular in cosmetic and dermatological preparations in combination with hair care agents and anti-dandruff active ingredients (for example climbazole, ketoconazole, piroctone oleamine, zinc-pyrithione).

The compounds of formula (I) can also advantageously be used in numerous cases in combination with one or more preservatives in preparations according to the invention. The preservatives mentioned in WO 2005/123101 are preferably selected here.

Preparations according to the invention, apart from one or more compounds of formula (I), may also contain plant extracts which can be used for cosmetic purposes. The plant extracts are preferably selected from the table of listed substances beginning on page 44 of the third edition of the handbook on the contents declaration of cosmetic agents, published by the Industrieverband Körperpflegemittel and Waschmittel e.V. (IKW), Frankfurt. The extracts mentioned in WO 2005/123101 are also particularly advantageous.

In preferred embodiments, a composition according to the present invention, comprises one or more cosmetically acceptable carriers selected from the group consisting of (i) (alkane) diols having 3 to 10 carbon atoms, preferably selected from the group consisting of 1,2-propylene glycol, 2-methylpropane-1,3-diol, 1,2-butylene glycol, 1,3-butanediol, 1,2-pentanediol, 1,3-pentanediol, 1,5-pentanediol, 2,4-pentanediol, 2-methylpentane-2,4-diol, 1,2-hexanediol, 1,6-hexanediol, 1,2-octanediol, dipropylene glycol, preferably 1,2-butylene glycol, 1,2-pentanediol and/or dipropylene glycol, and/or (ii-1) esters having 6 to 36 carbon atoms, preferably monoesters, diesters or triesters, preferably selected from the group consisting of diethyl phthalate, diethylhexyl 2,6-naphthalate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 3,5,5-trimethylhexyl 3,5,5-trimethylhexanoate, 2-ethylhexyl isononanoate, 2-ethylhexyl 3,5,5-trimethylhexanoate, 2-ethylhexyl 2-ethylhexanoate, 2-ethylhexyl palmitate, 2-ethylhexyl laurate, 2-hexyldecyl stearate, cetearyl ethylhexanoate, stearyl heptanoate, stearyl caprylate, 2-octyldodecyl palmitate, oleyl oleate, oleyl erucate, erucyl oleate, erucyl erucate, 2-ethylhexyl isostearate, isotridecyl isononanoate, 2-ethylhexyl cocoate, $C_{12-15}$-alkyl benzoates, cetyl palmitate, triethyl citrate, triacetin (triacetyl citrate), benzyl benzoate, benzyl acetate, vegetable oils (preferably olive oil, sunflower oil, soya oil, groundnut oil, rapeseed oil, almond oil, palm oil, coconut oil, palm kernel oil) and triglycerides, in particular glyceryl stearate, glyceryl triisononanoate, glyceryl laurate or triglycerides with identical or different C6 to C10 fatty acid radicals (so-called medium-chain triglycerides, in particular caprylic/capric triglyceride, like glyceryl tricaprylate, glyceryl tricaprate), and/or (ii-2) branched and unbranched alkyl or alkenyl alkohols, preferably selected from the group consisting of decanol, decenol, octanol, octenol, dodecanol, dodecenol, octadienol, decadienol, dodecadienol, oleyl alcohol, ricinoleyl alcohol, erucyl alcohol, stearyl alcohol, isostearyl alcohol, cetyl alcohol, lauryl alcohol, myristyl alcohol, arachidyl alcohol, linoleyl alcohol, linolenyl alcohol, hexyldecanol, octyldodecanol (in particular 2-octyl-1-dodecanol) and cetearyl alcohol and behenyl alcohol, and/or (ii-3) branched and unbranched hydrocarbons and waxes, cyclic or linear silicone oils and dialkyl ethers having 6 to 24 carbon atoms, preferably selected from the group consisting of jojoba oil, isoeicosane, dicaprylyl ether, mineral oil, petrolatum, squalane, squalene, cyclomethicone, decamethylcyclopentasiloxane, undecamethylcyclotrisiloxane, polydimethylsiloxane and poly(methyl-phenyl siloxane.

In other preferred embodiments, a composition according to the present invention, comprises one or more skin care agents, preferably skin moisture retention regulators or skin repair agents, preferably selected from the group consisting of sodium lactate, urea and derivatives, glycerol, 1,2-pentanediol, collagen, elastin or hyaluronic acid, diacyl adipates, petrolatum, urocanic acid, lecithin, allantoin, panthenol, phytantriol, lycopene, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, cholesterol, phytosterols, chitosan, chondroitin sulfate, lanolin, lanolin esters, amino acids, vitamin E and derivatives (preferably tocopherol, tocopheryl acetate), alpha-hydroxy acids (preferably citric acid, lactic acid, malic acid) and derivatives thereof, mono-, di- and oligosaccharides, preferably glucose, galactose, fructose, mannose, laevulose and lactose, polysugars, such as β-glucans, in particular 1,3-1, 4-β-glucan from oats, alpha-hydroxy-fatty acids, triterpenic acids, such as betulic acid or ursolic acid, and algae extracts, preferably selected from the group consisting of glycerol, 1,2-pentanediol, *urea*, hyaluronic acid, allantoin, panthenol, lanolin, alpha-hydroxy acids (preferably citric acid, lactic acid), vitamin E and derivatives (preferably tocopherol, tocopheryl acetate).

Formulations according to the invention can also contain preservatives. The following can be used as preservatives: all antioxidants which are suitable or commonly used for cosmetic (e.g. dermatological) and/or therapeutic applications, traditional preservatives (e.g. formaldehyde, glutardialdehyde, parabens (e.g. methyl, ethyl, propyl and butyl paraben), dibromodicyanobutane, imidazolidinyl ureas ("Germall"), isothiazolinones ("Kathon"), methyl chlorothiazolidine, methyl thiazolidine, organic acids (e.g. benzoic acid, sorbic acid, salicylic acid) and salts and esters thereof, propionic acid and formic acid and salts thereof, glycols (e.g. propylene glycol, 1,2-dihydroxyalkanes), plant-based preservative aids such as e.g. lantadin A, caryophyllene, hesperidin, diosmin, phellandrene, pigenin, quercetin, hypericin, aucubin, diosgenin, plumbagin, corlilagin and the like.

The cosmetic or therapeutic, preferably topical, preparations according to the invention also preferably contain antimicrobial active ingredients. Suitable antimicrobial actives are:

Aryl- or aryloxy-substituted, unbranched or monoalkyl- and polyalkyl-branched saturated or mono- to pentaunsaturated (up to five double or triple bonds, also mixed ene/ine compounds) fatty alcohols, fatty aldehydes and fatty acids having chain lengths of $C_2$ to $C_{40}$.

Aryl- or aryloxy-substituted, unbranched or monoalkyl- and polyalkyl-branched saturated or mono- to pentaunsaturated (up to five double or triple bonds, also mixed ene/ine compounds) alkane diols, dialdehydes and dicarboxylic acids having chain lengths of $C_2$ to $C_{40}$, particularly preferably chain lengths of $C_4$ to $C_{12}$.

Mono- and oligoglycerides (up to 4 glycerol units) of aryl- or aryloxy-substituted unbranched or monoalkyl- and polyalkyl-branched saturated or mono- to pentaunsaturated (up to five double or triple bonds, also mixed ene/ine compounds) fatty alcohols (mono- and oligoglycerol monoalkyl ethers), fatty acids (mono- and oligoglycerol monoalkyl esters), alkanediols (mono- and oligoglycerol monoalkyl ethers; bis(mono/oligoglyceryl)alkyl diethers) and dicarboxylic acids (mono- and oligoglycerol monoalkyl esters; bis(mono-/oligoglyceryl) alkyl diesters) having chain lengths of $C_2$ to $C_{40}$.

Fatty acid esters of unbranched or monoalkyl- and polyalkyl-branched saturated or mono- to pentaunsaturated (up to five double or triple bonds, also mixed ene/ine compounds), optionally also aryl- or aryloxy-substituted, carboxylic acids having chain lengths of $C_2$ to $C_{40}$ with unbranched or monoalkyl- and polyalkyl-branched saturated or mono- to pentaunsaturated (up to five double or triple bonds, also mixed ene/ine compounds), optionally also aryl- or aryloxy-substituted, monohydric to hexahydric fatty alcohols having chain lengths of $C_2$ to $C_{40}$.

Plant and animal fatty acid cuts, containing unbranched or monoalkyl- and polyalkyl-branched saturated or mono- to pentaunsaturated (up to five double or triple bonds, also mixed ene/ine compounds) fatty alcohols, fatty aldehydes and fatty acids having chain lengths of $C_2$ to $C_{40}$ (e.g. coconut fatty acids, palm kernel fatty acids, wool wax acids).

Mono- and oligoglycerides of lanolin, of lanolin alcohols and lanolic acids (e.g. glyceryl lanolate, neocerite), glycyrrhetic acid and derivatives (e.g. glycyrrhetinyl stearate), natural and synthetic cardenolides (e.g. digitoxin, dogoxin, digoxygenin, gitoxygenin, strophanthin and strophanthidin), natural and synthetic bufadienolides (e.g. scillaren A, scillarenin and bufotalin), sapogenins and steroid sapogenins (e.g. amyrins, oleanolic acid, digitonin, gitogenin, tigogenin and diosgenin), steroid alkaloids of plant and animal origin (e.g. tomatidin, solanin, solanidin, conessin, batrachotoxin and homobatrachotoxin).

Mono- and polyhalogenated nitriles, dinitriles, trinitriles or tetranitriles.

Mono- and oligohydroxy fatty acids having chain lengths of $C_2$ to $C_{24}$ (e.g. lactic acid, 2-hydroxypalmitic acid), oligomers and/or polymers thereof and plant and animal raw materials containing these.

Acyclic terpenes: terpene hydrocarbons (e.g. ocimene, myrcene), terpene alcohols (e.g. geraniol, linalool, citronellol), terpene aldehydes and ketones (e.g. citral, pseudoionone, beta-ionone); monocyclic terpenes: terpene hydrocarbons (e.g. terpinene, terpinolene, limonene), terpene alcohols (e.g. terpineol, thymol, menthol), terpene ketones (e.g. pulegone, carvone); bicyclic terpenes: terpene hydrocarbons (e.g. carane, pinane, bornane), terpene alcohols (e.g. borneol, isoborneol), terpene ketones (e.g. camphor); sesquiterpenes: acyclic sesquiterpenes (e.g. farnesol, nerolidol), monocyclic sesquiterpenes (e.g. bisabolol), bicyclic sesquiterpenes (e.g. cadinene, selinene, vetivazulene, guajazulene), tricyclic sesquiterpenes (e.g. santalene), diterpenes (e.g. phytol), tricyclic diterpenes (e.g. abietic acid), triterpenes (squalenoids; e.g. squalene), tetraterpenes.

Ethoxylated, propoxylated or mixed ethoxylated/propoxylated cosmetic fatty alcohols, fatty acids and fatty acid esters having chain lengths of $C_2$ to $C_{40}$ with 1 to 150 E/O and/or P/O units.

Antimicrobial peptides and proteins having an amino acid value from 4 to 200, e.g. Skin Antimicrobial Peptides (SAPs), Lingual Antimicrobial Peptides (LAPs), human betadefensins (in particular h-BD1 and h-BD2), lactoferrins and hydrolysates thereof and peptides obtained therefrom, Bactericidal/Permeability Increasing Proteins [BPIs], Cationic Microbial Proteins [CAPs], lysozyme.

Very suitable carbohydrates or "carbohydrate derivatives", which in the interests of brevity can also be included under the term "carbohydrates", are compounds containing sugars and substituted sugars or sugar groups. The sugars include in particular also the deoxy and dideoxy forms, N-acetyl galactosamine-, N-acetyl glucosamine- and sialic acid-substituted derivatives as well as sugar esters and ethers. Preference is given to a) monosaccharides, including in particular pentoses and hexoses,
b) disaccharides, including in particular sucrose, maltose, lactobiose,
c) oligosaccharides, including in particular the tri- and tetrasaccharides, and
d) polysaccharides, including in particular starch, glycogen, cellulose, dextran, tunicin, inulin, chitin, in particular chitosans, chitin hydrolysates, alginic acid and alginates, plant gums, body mucosa, pectins, mannans, galactans, xylans, araban, polyoses, chondroitin sulfates, heparin, hyaluronic acid and glycosaminoglycanes, hemicelluloses, substituted cellulose and substituted starch, in particular the hydroxyalkyl-substituted polysaccharides in each case.

Amylose, amylopectin, xanthan, alpha-, beta- and gamma-dextrin are particularly suitable. The polysaccharides can consist of e.g. 4 to 1,000,000, in particular 10 to 100,000, monosaccharides. Chain lengths are preferably chosen in each case which ensure that the active ingredient is soluble in or can be incorporated into the particular formulation.

Sphingolipids such as sphingosine; N-monoalkylated sphingosines; N,N-dialkylated sphingosines; sphingosine-1-phosphate; sphingosine-1-sulfate; psychosine (sphingosine-beta-D-galactopyranoside); sphingosyl phosphoryl cholin; lysosulfatides (sphingosyl galactosyl sulfate; lysocerebroside sulfate); lecithin; sphingomyelin; sphinganine.

So-called "natural" antibacterial active ingredients can also be used, most of which are essential oils. Typical oils having an antibacterial action are, for example, oils of aniseed, lemon, orange, rosemary, wintergreen, clove, thyme, lavender, hops, citronella, wheat, lemongrass, cedarwood, cinnamon, geranium, sandalwood, violet, eucalyptus, peppermint, gum benzoin, basil, fennel, menthol and *Ocmea origanum, Hydastis carradensis, Berberidaceae daceae, Ratanhiae* or *Curcuma longa.*

Important substances having an antimicrobial action which can be found in essential oils are for example anethol, catechol, camphene, carvacrol, eugenol, eucalyptol, ferulic acid, farnesol, hinokitiol, tropolone, limonene, menthol, methyl salicylate, thymol, terpineol, verbenone, berberine, curcumin, caryophyllene oxide, nerolodol, geraniol.

Mixtures of the cited active systems or active ingredients and active ingredient combinations containing these active ingredients can also be used.

The amount of antimicrobial active ingredients in the formulations is preferably 0.01 to 20 wt. %, based on the total weight of the formulations, particularly preferably 0.05 to 10 wt. %.

In another preferred embodiment a topical, preferably cosmetic, preparation according to the present invention additionally comprises one or more fragrance materials, preferably having a Clog P value of at least 3, preferably of at least 4, more preferably of at least 5. Suitable fragrance materials are mentioned in S. Arctander, Perfume and Flavor Chemicals, Vol. I and II, Montclair, N.J., 1969, self-published or H. Surburg and J. Panten, Common Fragrance and Flavor Materials, 5th. Ed., Wiley-VCH, Weinheim 2006, particularly those explicitly mentioned in US 2008/0070825.

Preparations according to the present invention advantageously comprise a total amount of 0.1 to 5 wt. %, preferably 0.2 to 4 wt. %, more preferably 0.25 to 3 wt. %, even more preferably 0.3-2.5 wt. %, of the one or more (preferred) fragrance materials, in each case based on the total weight of the preparation.

In a further preferred embodiment a preparation, preferably a cosmetic leave-on product, according to the present invention additionally comprises one or more of fragrance materials having a boiling point of 250° C. or greater (at 1013 mbar). The total amount of fragrance materials having a boiling point of 250° C. or greater (at 1013 mbar) preferably is at least 10 wt. %, more preferably at least 20 wt. %, based on the total amount of fragrance materials present in a preparation according to the present invention.

More preferably the fragrance materials, preferably having a boiling point of 250° C. or greater at 1013 mbar, are selected from (here in some cases the normal industrial product names and registered trademarks of various firms are given):

alpha-amyl cinnamic aldehyde, alpha-hexyl cinnamic aldehyde, 2-phenoxyethylisobutyrate (Phenirat), methyl dihydrojasmonate [preferably with a content of cis-isomers of >60 by weight (Hedione, Hedione HC)], 4,6,6,7,8,8-hexamethyl-1,3,4,6,7,8-hexahydrocyclopenta[g]benzopyran (Galaxolide), benzylsalicylate, 2-methyl-3-(4-tert-butylphenyl)propanal (Lilial), 4,7-methano-3a,4,5,6,7,7a-hexahydro-5-indenyl acetate and/or 4,7-methano-3a,4,5,6,7,7a-hexahydro-6-indenyl acetate (Herbaflorat), styrallyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthaline (Iso E Super), hexylsalicylate, 4-tert.-butylcyclohexyl acetate (Oryclon), 2-tert.-butylcyclohexyl acetate (Agrumex HC), alpha-ionone (4-(2,2,6-trimethyl-2-cyclohexen-1-yl)-3-buten-2-one), 4-(4-hydroxy-4-methylpentyl)-3-cyclohexene carboxaldehyde (Lyral), (E)- and/or (Z)-3-methylcyclopentadec-5-enone (Muscenone), 15-pentadec-11-enolide and/or 15-pentadec-12-enolide (Globalide), 15-cyclopentadecanolide (Macrolide), 1-(5,6,7,8-tetrahydro-3,5,5,6,8,8-hexamethyl-2-naphthalenyl)ethanone (Tonalide), ethylene brassylate, 2-ethyl-4-(2,2,3-trimethyl-3-cyclopenten-1-yl)-2-buten-1-ol (Sandranol), alpha-Santalol, 2,2-dimethyl-3-(3-methylphenyl)-propanol (Majantol), allyl heptanoate, 4-methylacetophenone, (4aR, 5R,7aS,9R)-octahydro-2,2,5,8,8,9a-hexamethyl-4H-4-a,9-methanoazuleno(5,6-d)-1,3-dioxol) (Ambrocenide), Timberol (1-(2,2,6-trimethylcyclohexyl)hexan-3-ol), benzylacetone, methyl cinnamate, 3a,6,6,9a-tetramethyldodecahydronaphtho[2,1-b]furan (Ambroxid).

Cosmetic or pharmaceutical preparations containing one or more compounds of formula (I) may, in particular if crystalline or microcrystalline solid bodies such as, for example, inorganic micropigments are to be incorporated in the preparations, according to the invention also contain anionic, cationic, non-ionic and/or amphoteric surfactants mentioned in WO 2005/123101.

Anionic surfactants generally have carboxylate, sulfate or sulfonate groups as functional groups. In aqueous solution they form negatively charged organic ions in the acid or neutral environment. Cationic surfactants are almost exclusively characterised by the presence of a quaternary ammonium group. In aqueous solution they form positively charged organic ions in the acid or neutral environment. Amphoteric surfactants contain both anionic and cationic groups and therefore behave in aqueous solution in the same way as anionic or cationic surfactants, depending on the pH. They have a positive charge in a strongly acid environment and a negative charge in an alkaline environment. In the neutral pH range, by contrast, they are zwitterionic. Polyether chains are typical of non-ionic surfactants. Non-ionic surfactants do not form ions in the aqueous medium.

A. Anionic Surfactants

Anionic surfactants which can advantageously be used are acyl amino acids (and salts thereof), such as acyl glutamates, for example sodium acyl glutamate, di-TEA-palmitoyl aspartate and sodium caprylic/capric glutamate, acyl peptides, for example palmitoyl-hydrolysed milk protein, sodium cocoyl-hydrolysed soya protein and sodium/potassium cocoyl-hydrolysed collagen, sarcosinates, for example myristoyl sarcosin, TEA-lauroyl sarcosinate, sodium lauroyl sarcosinate and sodium cocoyl sarcosinate, taurates, for example sodium lauroyl taurate and sodium methyl cocoyl taurate, acyl lactylates, lauroyl lactylate, caproyl lactylate alaninates carboxylic acids and derivatives, such as for example lauric acid, aluminium stearate, magnesium alkanolate and zinc undecylenate, ester carboxylic acids, for example calcium stearoyl lactylate, laureth-6 citrate and sodium PEG-4 lauramide carboxylate, ether carboxylic acids, for example sodium laureth-13 carboxylate and sodium PEG-6 cocamide carboxylate, phosphoric acid esters and salts, such as e.g. DEA-oleth-10-phosphate and dilaureth-4 phosphate, sulfonic acids and salts, such as acyl isothionates, e.g. sodium/ammonium cocoyl isothionate, alkyl aryl sulfonates, alkyl sulfonates, for example sodium cocomonoglyceride sulfate, sodium $C_{12-14}$ olefin sulfonate, sodium lauryl sulfoacetate and magnesium PEG-3 cocamide sulfate, sulfosuccinates, for example dioctyl sodium sulfosuccinate, disodium laureth sulfosuccinate, disodium lauryl sulfosuccinate and disodium undecylenamido MEA sulfosuccinate and sulfuric acid esters, such as alkyl ether sulfate, for example sodium, ammonium, magnesium, MIPA, TIPA laureth sulfate, sodium myreth sulfate and sodium $C_{12-13}$ pareth sulfate, alkyl sulfates, for example sodium, ammonium and TEA lauryl sulfate.

B. Cationic Surfactants

Cationic surfactants which can advantageously be used are
alkyl amines,
alkyl imidazoles,
ethoxylated amines and
quaternary surfactants.
$RNH_2CH_2CH_2COO^-$ (where pH=7)
$RNHCH_2CH_2COO-B^+$ (where pH=12) $B^+$=any cation, e.g. $Na^+$
esterquats Quaternary surfactants contain at least one N atom, which is covalently bonded to 4 alkyl or aryl groups. This leads to a positive charge, regardless of the pH. Alkyl betaine, alkyl amidopropyl betaine and alkyl amidopropyl hydroxysulfaine are advantageous. The cationic surfactants used can also preferably be chosen from the group of quaternary ammonium compounds, in particular benzyl trialkyl ammonium chlorides or bromides, such as benzyl dimethylstearyl ammonium chloride for example, also alkyl trialkyl ammonium salts, for example cetyl trimethyl ammonium chloride or bromide, alkyl dimethyl hydroxyethyl ammonium chlorides or bromides, dialkyl dimethyl ammonium chlorides or bromides, alkyl amide ethyl trimethyl ammonium ether sulfates, alkyl pyridinium salts, for example lauryl or cetyl pyrimidinium chloride, imidazoline derivatives and compounds having a cationic character such as amine oxides, for example alkyl dimethyl amine oxides or alkyl aminoethyl dimethyl amine oxides. Cetyl trimethyl ammonium salts are particularly advantageously used.

C. Amphoteric Surfactants

Amphoteric surfactants which can advantageously be used are
acyl/dialkyl ethylene diamine, for example sodium acyl amphoacetate, disodium acyl amphodipropionate, disodium alkyl amphodiacetate, sodium acyl amphohydroxypropyl sulfonate, disodium acyl amphodiacetate and sodium acyl amphopropionate,
N-alkyl amino acids, for example aminopropyl alkyl glutamide, alkyl aminopropionic acid, sodium alkyl imidodipropionate and lauroamphocarboxyglycinate.

D. Non-Ionic Surfactants

Non-ionic surfactants which can advantageously be used are
alcohols,
alkanolamides, such as cocamides MEA/DEA/MIPA,
amine oxides, such as cocamidopropylamine oxide,
esters produced by esterification of carboxylic acids with ethylene oxide, glycerol, sorbitan or other alcohols,
ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides such as lauryl glucoside, decyl glycoside and cocoglycoside,
sucrose esters, ethers,
polyglycerol esters, diglycerol esters, monoglycerol esters, methyl glucose esters, esters of hydroxy acids.

The use of a combination of anionic and/or amphoteric surfactants with one or more non-ionic surfactants is also advantageous.

The surface-active substance (surfactant) or the combination of surface-active substances can be present in the formulations according to the invention in a concentration of between 1 and 98 wt. %, based on the total weight of the formulations.

Cosmetic (e.g. dermatological) or pharmaceutical formulations according to the invention containing one or more compounds according to the invention or for use according to the invention having formula (I) can also take the form of emulsions.

The oil phase of preparations according to the invention, which contain one or more compounds of formula (I) may advantageously be selected from the substance groups mentioned in WO 2005/123101.

The oil phase (lipid phase) in the formulations according to the invention (in particular topical cosmetic formulations) can advantageously be selected from the following group of substances:
mineral oils (advantageously paraffin oil), mineral waxes
fatty oils, fats, waxes and other natural and synthetic fat bodies, preferably esters of fatty acids with low C-number alcohols, for example with isopropanol, propylene glycol or glycerol, or esters of fatty alcohols with low C-number alkanoic acids or with fatty acids;
alkyl benzoates (e.g. mixtures of n-dodecyl, n-tridecyl, n-tetradecyl or n-pentadecyl benzoate);
cyclic or linear silicone oils such as dimethyl polysiloxanes, diethyl polysiloxanes, diphenyl polysiloxanes and mixed forms thereof.

(Natural or synthetic) esters are advantageously used, in particular (a) esters of saturated and/or unsaturated branched and/or unbranched alkane carboxylic acids having a chain length of 3 to 30 C atoms and saturated and/or unsaturated, branched and/or unbranched alcohols having a chain length of 3 to 30 C atoms, (b) esters of aromatic carboxylic acids and saturated and/or unsaturated, branched and/or unbranched alcohols having a chain length of 3 to 30 C atoms. Preferred ester oils are isopropyl myristate, isopropyl palmitate, isopropyl stearate, isopropyl oleate, n-butyl stearate, n-hexyl laurate, n-decyl laurate, n-decyl oleate, isooctyl stearate, isononyl stearate, isononyl isononanoate, 3,5,5-trimethylhexyl-3,5,5-trimethylhexanoate, 2-ethylhexyl isononanoate, 2-ethylhexyl-3,5,5-trimethyl hexanoate, 2-ethyl hexyl-2-ethyl hexanoate, cetearyl-2-ethylhexanoate, 2-ethylhexyl palmitate, 2-ethylhexyl laurate, 2-hexyldecyl stearate, 2-octyldecyl palmitate, 2-octyldodecyl palmitate, oleyl oleate, oleyl erucate, erucyl oleate, erucyl erucate and synthetic, semisynthetic and natural mixtures of such esters, e.g. jojoba oil.

The oil phase can also advantageously be chosen from the group consisting of branched and unbranched hydrocarbons and hydrocarbon waxes, silicone oils, dialkyl ethers, the group consisting of saturated or unsaturated, branched or unbranched alcohols, and of fatty acid triglycerides, in particular the triglycerol esters of saturated and/or unsaturated, branched and/or unbranched alkane carboxylic acids having a chain length of 8 to 24, in particular 12 to 18 C atoms. The fatty acid triglycerides can advantageously be selected from the group of synthetic, semisynthetic and natural oils, e.g. triglycerides of capric or caprylic acid, apricot kernel oil, avocado oil, cottonseed oil, borage seed oil, thistle oil, groundnut oil, gamma-oryzanol, rosehip seed oil, hemp oil, hazelnut oil, blackcurrant seed oil, coconut oil, cherry kernel oil, salmon oil, flax oil, maize oil, *macadamia* nut oil, almond oil, evening primrose oil, mink oil, olive oil, palm oil, palm kernel oil, pecan nut oil, peach kernel oil, pistachio nut oil, rapeseed oil, rice bran oil, castor oil, safflower oil, sesame oil, soya oil, sunflower oil, teatree oil, grape seed oil or wheat germ oil, and the like. Any blends of such oil and wax components can also advantageously be used. In some cases it is also advantageous to use waxes, for example cetyl palmitate, as the sole lipid component of the oil phase, the oil phase advantageously being chosen from the group consisting of 2-ethylhexyl isostearate, octyl dodecanol, isotridecyl isononanoate, isoeicosane, 2-ethylhexyl cocoate, $C_{12-15}$-alkyl benzoate, caprylic-capric acid triglyceride and dicaprylyl ether. Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous. The hydrocarbons paraffin oil, squalane and squalene can also advantageously be used. The oil phase can advantageously also have a content of cyclic or linear silicone oils or consist entirely of such oils, it being preferable, however, to use an additional content of other oil phase components along with the silicone oil or silicone oils. Cyclomethicone (e.g. decamethyl cyclopentasiloxane) can advantageously be used as the silicone oil. Other silicone oils can also advantageously be used, however, for example undecamethyl cyclotrisiloxane, polydimethyl siloxane and poly(methylphenyl siloxane). Mixtures of cyclomethicone and isotridecyl isononanoate and of cyclomethicone and 2-ethylhexyl isostearate are also particularly advantageous.

The aqueous phase of formulations according to the invention (in particular topical cosmetic formulations) in the form of an emulsion can advantageously include: alcohols, diols or polyols having a low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, also alcohols having a low C number, e.g. ethanol, isopropanol, 1,2-propanediol, glycerol and in particular one or more thickeners, which can advantageously be chosen from the group comprising silicon dioxide, aluminium silicates such as e.g. bentonites, polysaccharides or derivatives thereof, e.g. hyaluronic acid, guar gum, xanthan gum, hydroxypropyl methyl cellulose, or allulose derivatives, particularly advantageously from the group of polyacrylates, preferably a polyacrylate from the group of so-called carbopols, for example type 980, 981, 1382, 2984, 5984 carbopols, either individually or in combination, or from the group of polyurethanes, also alpha- or beta-hydroxy acids, preferably lactic acid, citric acid or salicylic acid, also emulsifiers, which can advantageously be selected from the group of ionic, non-ionic, polymeric, phosphate-containing and zwitterionic emulsifiers.

Formulations according to the invention in the form of an emulsion advantageously include one or more emulsifiers. O/W emulsifiers, for example, can advantageously be chosen from the group of polyethoxylated or polypropoxylated or polyethoxylated and polypropoxylated products, e.g.:
fatty alcohol ethoxylates,
ethoxylated wool wax alcohols,
polyethylene glycol ethers having the general formula R—O—(—CH$_2$—CH$_2$—O—)$_n$—R',
fatty acid ethoxylates having the general formula R—COO—(—CH$_2$—CH$_2$—O—)$_n$—H,
etherified fatty acid ethoxylates having the general formula R—COO—(—CH$_2$—CH$_2$—O—)$_n$—R', esterified fatty acid ethoxylates having the general formula R—COO—(—CH$_2$—CH$_2$—O—)$_n$—C(O)—R', polyethylene glycol glycerol fatty acid esters,
ethoxylated sorbitan esters,
cholesterol ethoxylates,
ethoxylated triglycerides,
alkyl ether carboxylic acids having the general formula R—COO—(—CH$_2$—CH$_2$—O—)$_n$—OOH, where n represents a number from 5 to 30, polyoxyethylene sorbitol fatty acid esters,
alkyl ether sulfates having the general formula R—O—(—CH$_2$—CH$_2$—O—)$_n$—SO$_3$—H,
fatty alcohol propoxylates having the general formula R—O—(—CH$_2$—CH(CH$_3$)—O—)$_n$—H,
polypropylene glycol ethers having the general formula R—O—(—CH$_2$—CH(CH$_3$)—O—)$_n$—R', propoxylated wool wax alcohols,
etherified fatty acid propoxylates R—COO—(—CH$_2$—CH(CH$_3$)—O—)$_n$—R',
esterified fatty acid propoxylates having the general formula R—COO—(—CH$_2$—CH(CH$_3$)—O—)$_n$—C(O)—R', fatty acid propoxylates having the general formula R—COO—(—CH$_2$—CH(CH$_3$)—O—)$_n$—H, polypropylene glycol glycerol fatty acid esters,
propoxylated sorbitan esters,
cholesterol propoxylates,
propoxylated triglycerides,
alkyl ether carboxylic acids having the general formula R—O—(—CH$_2$—CH(CH$_3$)—O—)$_n$—CH$_2$—COOH, alkyl ether sulfates or the acids on which these sulfates are based having the general formula R—O—(—CH$_2$—CH(CH$_3$)—O—)$_n$—SO$_3$—H,
fatty alcohol ethoxylates/propoxylates having the general formula R—O—X$_n$—Y$_m$—H,
polypropylene glycol ethers having the general formula R—O—X$_n$—Y$_m$—R',
etherified fatty acid propoxylates having the general formula R—COO—X$_n$—Y$_m$—R',
fatty acid ethoxylates/propoxylates having the general formula R—COO—X$_n$—Y$_m$—H.

Particularly advantageously according to the invention the polyethoxylated or polypropoxylated or polyethoxylated and polypropoxylated O/W emulsifiers used are chosen from the group of substances having HLB values of 11 to 18, most particularly advantageously having HLB values of 14.5 to 15.5, if the O/W emulsifiers have saturated R and R' radicals. If the O/W emulsifiers have unsaturated R and/or R' radicals, or if isoalkyl derivatives are present, the preferred HLB value of such emulsifiers can also be lower or higher.

It is advantageous to choose the fatty alcohol ethoxylates from the group of ethoxylated stearyl alcohols, cetyl alcohols, cetyl stearyl alcohols (cetearyl alcohols). Particularly preferred are:
polyethylene glycol (n) stearyl ether (steareth-n) where n=13-20,
polyethylene glycol (n) cetyl ether (ceteth-n) where n=13-20,
polyethylene glycol (n) isocetyl ether (isoceteth-n) where n=13-20,
polyethylene glycol (n) cetyl stearyl ether (ceteareth-n) where n=13-20,
polyethylene glycol (m) isostearyl ether (isosteareth-m) where m=12-20,
polyethylene glycol (k) oleyl ether (oleth-k) where k=12-15,
polyethylene glycol (12) lauryl ether (laureth-12),
polyethylene glycol (12) isolauryl ether (isolaureth-12).

It is also advantageous to choose the fatty acid ethoxylates from the following group:
polyethylene glycol (n) stearate where n=20-25,
polyethylene glycol (m) isostearate where m=12-25,
polyethylene glycol (k) oleate where k=12-20.

Sodium laureth-11 carboxylate can advantageously be used as the ethoxylated alkyl ether carboxylic acid or its salt. Sodium laureth 1-4 sulfate can advantageously be used as the alkyl ether sulfate. Polyethylene glycol (30) cholesteryl ether can advantageously be used as the ethoxylated cholesterol derivative. Polyethylene glycol (25) soya sterol has also proved itself.

Polyethylene glycol (60) evening primrose glycerides can advantageously be used as ethoxylated triglycerides.

It is also advantageous to choose the polyethylene glycol glycerol fatty acid esters from the group comprising polyethylene glycol (n) glyceryl laurate where n=20-23, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise beneficial to choose the sorbitan esters from the group comprising polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be used as advantageous W/O emulsifiers: fatty alcohols having 8 to 30 carbon atoms, monoglycerol esters of saturated and/or unsaturated, branched and/or unbranched alkane carboxylic acids having a chain length of 8 to 24, in particular 12 to 18 C atoms, diglycerol esters of saturated and/or unsaturated, branched and/or unbranched alkane carboxylic acids having a chain length of 8 to 24, in particular 12 to 18 C atoms, monoglycerol ethers of saturated and/or unsaturated, branched and/or unbranched alcohols having a chain length of 8 to 24, in particular 12 to 18 C atoms, diglycerol ethers of saturated and/or unsaturated, branched and/or unbranched alcohols having a chain length of 8 to 24, in particular 12 to 18 C atoms, propylene glycol esters of saturated and/or unsaturated, branched and/or unbranched alkane carboxylic acids having a chain length of 8 to 24, in particular 12 to 18 C atoms, and sorbitan esters of saturated and/or unsaturated, branched and/or unbranched alkane carboxylic acids having a chain length of 8 to 24, in particular 12 to 18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

The formulations according to the invention (in particular cosmetic, including dermatological formulations) can contain deodorants, i.e. active ingredients having a deodorising and perspiration-inhibiting action. These include, for example, odour maskers, such as the common perfume constituents, antiperspirants based on aluminium, zirconium or zinc salts, odour absorbers, for example the layered silicates described in DE-P 40 09 347, in particular montmorillonite, kaolinite, nontronite, saponite, hectorite, bentonite, smectite, and also zinc salts of ricinoleic acid, for example. They also include bactericidal or bacteriostatic deodorising substances, such as e.g. hexachlorophene, 2,4,4'-trichloro-2'-hydroxydiphenyl ether (Irgasan), 1,6-di-(4-chlorophenylbiguanido) hexane (chlorhexidine), 3,4,4'-trichlorocarbanilide, and the active agents described in the laid-open patent specifications DE-37 40 186, DE-39 38 140, DE-42 04 321, DE-42 29 707, DE-42 29 737, DE-42 37 081, DE-43 09 372, DE-43 24 219 and containing cation-active substances, such as e.g. quaternary ammonium salts and odour absorbers such as e.g. Grillocin® (combination of zinc ricinoleate and various additives) or triethyl citrate, optionally in combination with ion-exchange resins.

The amount of deodorising and/or antiperspirant active ingredients in the formulations is preferably 0.01 to 20 wt. %, based on the total weight of the formulations, particularly preferably 0.05 to 10 wt. %.

Preferred embodiments and further aspects of the present invention emerge from the attached patent claims and the following examples.

The examples describe the invention in more detail, without limiting the area of protection of the claims. Unless stated otherwise, all the data, in particular amounts and percentages, relate to the weight.

EXAMPLES 1

Synthesis of Compounds of Formula (I)

EXAMPLES 1.1

Di-substituted cyclohexyl carbamates of formula (Carb-II-R1H)

The following cyclohexyl carbamates were produced analogously to the methodology as described for BIO1824 in example 1.3.1., below. The cyclohexyl carbamates were obtained in comparable yields and purities (generally >99%, generally as a mixture of stereoisomers, depending on the structure):

EXAMPLE 1.1.1

(2-Hydroxy-phenyl)-carbamic acid 2,3-dimethyl-cyclohexyl ester (BIO1643)

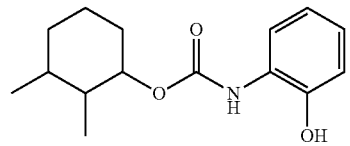 [SMILES: CC1CCCC(OC(=O)Nc2ccccc2O)C1C]

main signals of isomer mixture:
$^1$H-NMR (400 MHz, CDCl$_3$, TMS): δ=7.93 (m, H), 7.15 (d, 7.5 Hz, H), 7.05 (d,d, 7.7 Hz, 8.1 Hz, H), 6.97 (d, 8.1 Hz, H), 6.87 (d,d, 7.3 Hz, 7.7 Hz, H), 6.7 (m, H), 4.81 (t,d, 4.5 Hz, 11.6 Hz, H), 1.10-2.18 (m, 8 H), 0.92 (d, 6.9 Hz, 3 H), 0.86 (d, 7.1 Hz, 3 H) ppm.
$^{13}$C-NMR (400 MHz, CDCl$_3$, TMS): δ=155.4 (s), 147.2 (s), 125.6 (d), 125.4 (s), 121.2 (d), 120.9 (d), 118.6 (d), 78.6 (d), 37.3 (d), 34.6 (t), 34.2 (d), 27.2 (t), 25.4 (t), 19.1 (q), 6.2 (q) ppm.
MS (EI): m/z=263 (15), 153 (100), 135 (15), 110 (21), 109 (64), 95 (9), 81 (9), 69 (51), 55 (27), 41 (11).

EXAMPLE 1.1.2

Ethyl-carbamic acid 3,5-dimethyl-cyclohexyl ester (BIO1561)

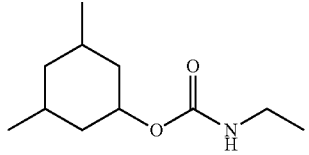

main signals of isomer mixture:
$^1$H-NMR (400 MHz, CDCl$_3$, TMS): δ=4.61 (m, 2 H), 3.20 (m, 2 H), 1.96 (d, 11.9 Hz, 2 H), 1.60 (d, 14.4 Hz, H), 1.52 (m, 2 H), 1.13 (t, 7.2 Hz, 3 H), 0.92 (d, 6.6 Hz, 6 H), 0.80-1.05 (m, 2 H), 0.53 (q, 11.9 Hz, H) ppm.
$^{13}$C-NMR (400 MHz, CDCl$_3$, TMS): δ=156.3 (s), 73.1 (d), 43.1 (t), 40.5 (t), 40.5 (t), 38.4 (t), 30.6 (d), 30.6 (d), 22.2 (q), 22.2 (q), 15.3 (q) ppm.
MS (EI, major isomer): m/z=199 (not detected), 127 (4), 95 (41), 90 (100), 69 (65), 55 (39), 41 (62), 29 (26).

EXAMPLE 1.1.3 p-Tolyl-carbamic acid 3,5-dimethyl-cyclohexyl ester (BIO1822)

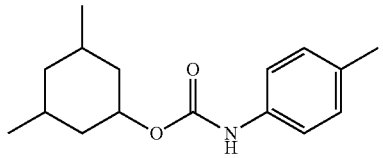

main signals of isomer mixture:
$^1$H-NMR (400 MHz, CDCl$_3$, TMS): δ=7.25 (d, 8.1 Hz, 2 H), 7.10 8d, 8.3 Hz, 2 H), 6.45 (m, H), 4.71 (t,t, 4.4 Hz, 11.3 Hz, H), 2.30 (s, 3 H), 2.03 (d, 12.0 Hz, 2 H), 1.62 (d, 14.1 Hz, H), 1.55 (m, 2 H), 0.97 (q, 11.3 Hz, 2 H), 0.94 (d, 6.6 Hz, 6 H), 0.56 (d,t, 11.5 Hz, 12.6 Hz, H) ppm.
$^{13}$C-NMR (400 MHz, CDCl$_3$, TMS): δ=153.4 (s), 135.5 (s), 132.8 (s), 129.5 (d), 129.5 (d), 118.7 (d), 118.7 (d), 73.9 (d), 43.0 (t), 40.3 (t), 40.3 (t), 30.6 (d), 30.6 (d), 22.2 (q), 22.2 (q), 20.7 (q) ppm.
MS (EI): m/z=262 (5), 261 (24), 151 (100), 107 (72), 106 (20), 69 (45), 55 (20), 41 (11).

EXAMPLE 1.1.4 n-Butyl-carbamic acid 3,5-dimethyl-cyclohexyl ester (BIO1840)

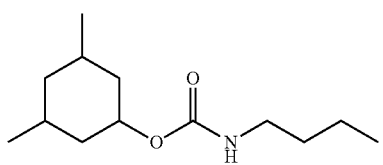 [SMILES: CCCCNC(=O)OC1CC(C)CC(C)C1]

main signals of isomer mixture:
$^1$H-NMR (400 MHz, CDCl$_3$, TMS): δ=4.58 (m, 2 H), 3.14 (q, 6.3 Hz, 2 H), 1.94 (d, 11.7 Hz, 2 H), 1.58 (d, 12.6 Hz, H), 1.40-1.54 (m, 4 H), 1.32 (m, 2 H), 0.90 (d, 6.5 Hz, 6 H), 0.90 (t, 7.2 Hz, 3 H), 0.89 (q, 11.8 Hz, 2 H), 0.50 (q, 12.0 Hz, H) ppm.
$^{13}$C-NMR (400 MHz, CDCl$_3$, TMS): δ=156.4 (s), 73.1 (d), 43.1 (t), 40.6 (t), 40.5 (t), 40.5 (t), 32.1 (t), 30.6 (d), 30.6 (d), 22.2 (q), 22.2 (q), 19.9 (t), 13.7 (q) ppm.
MS (EI): m/z=227 (1), 184 (1), 118 (100), 111 (43), 95 (28), 69 (77), 55 (28), 41 (29), 30 (19).

EXAMPLE 1.1.5

Phenyl-carbamic acid 3,5-dimethyl-cyclohexyl ester (BIO1685)

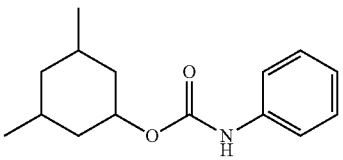 [SMILES: CC1CC(C)CC(OC(=O)Nc2ccccc2)C1]

main signals of isomer mixture:
$^1$H-NMR (400 MHz, CDCl$_3$, TMS): δ=7.37 (d, 7.9 Hz, 2 H), 7.30 (m, 2 H), 7.05 (m, H), 6.53 (m, H), 4.72 (t,t, 4.3 Hz, 11.4 Hz, H), 2.04 (d, 11.7 Hz, 2 H), 1.63 (d, 12.5 Hz, H), 1.55 (m, 2 H), 0.94 (q, 11.7 Hz, 2 H), 0.94 (d, 6.5 Hz, 6 H), 0.56 (d,t, 11.6 Hz, 12.6 Hz, H) ppm.
$^{13}$C-NMR (400 MHz, CDCl$_3$, TMS): δ=153.2 (s), 138.1 (s), 129.0 (d), 129.0 (d), 123.2 (d), 118.6 (d), 118.6 (d), 74.0 (d), 43.0 (t), 40.3 (t), 40.3 (t), 30.6 (d), 30.6 (d), 22.1 (q), 22.1 (q) ppm.
MS (EI): m/z=248 (3), 247 (15), 137 (29), 111 (29), 95 (34), 93 (84), 69 (100), 55 (47), 41 (35).

EXAMPLE 1.1.6

Butyl-carbamic acid 2-isopropenyl-5-methyl-cyclohexyl ester (BIO1615)

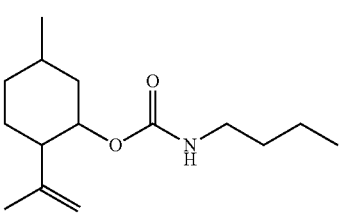 [SMILES: C=C(C)C1CCC(C)CC1OC(=O)NCCCC]

main signals of isomer mixture:
$^1$H-NMR (400 MHz, CDCl$_3$, TMS): δ=4.73 (m, 2 H), 4.65 (d,t, 4.3 Hz, 10.9 Hz, H), 4.54 (m, H), 3.13 (d,t, 6.0 Hz, 6.0 Hz, 2 H), 2.07 (m, 2 H), 1.63-1.73 (m, 2 H), 1.69 (t, 1.2 Hz, 3 H), 1.56 (m, H), 1.26-1.49 (m, 5 H), 0.87-1.02 (m, 2 H), 0.92 (d, 6.5 Hz, 3 H), 0.91 (t, 7.2 Hz, 3 H) ppm.
$^{13}$C-NMR (400 MHz, CDCl$_3$, TMS): δ=156.4 (s), 146.8 (s), 111.5 (t), 73.8 (d), 51.0 (d), 41.0 (t), 40.6 (t), 34.2 (t), 32.1 (t), 31.4 (d), 30.7 (t), 22.0 (q), 19.9 (t), 19.5 (q), 13.7 (q) ppm.
MS (EI, major isomer): m/z=254 (1), 253 (4), 136 (100), 118 (87), 107 (35), 93 (40), 81 (56), 67 (20), 57 (20), 41 (32), 29 (10).

EXAMPLE 1.1.7

Ethyl-carbamic acid 2-isopropenyl-5-methyl-cyclohexyl ester (BIO1551)

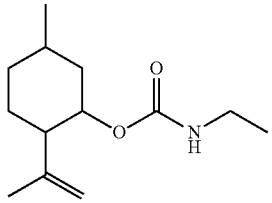 [SMILES: C=C(C)C1CCC(C)CC1OC(=O)NCC]

main signals of isomer mixture:
$^1$H-NMR (400 MHz, CDCl$_3$, TMS): δ=4.74 (m, 2 H), 4.65 (d,t, 4.3 Hz, 10.9 Hz, H), 4.58 (m, H), 3.18 (m, 2 H), 1.87-2.11 (m, 2 H), 1.48-1.75 (m, 3 H), 1.69 (t, 1.2 Hz, 3 H), 1.39 (m, H), 1.10 (t, 7.2 Hz, 3 H), 0.82-1.03 (m, 2 H), 0.92 (d, 6.6 Hz, 3 H) ppm.
$^{13}$C-NMR (400 MHz, CDCl$_3$, TMS): δ=156.3 (s), 146.6 (s), 111.5 (t), 73.7 (d), 51.0 (d), 41.1 (t), 35.7 (t), 34.2 (t), 31.4 (d), 30.7 (t), 22.1 (q), 19.5 (q), 15.2 (q) ppm.
MS (EI, major isomer): m/z=226 (1), 225 (2), 136 (100), 121 (58), 107 (37), 90 (62), 81 (48), 69 (19), 55 (21), 41 (21), 29 (20).

EXAMPLE 1.1.8

Butyl-carbamic acid 2,3-dimethyl-cyclohexyl ester (BIO1842)

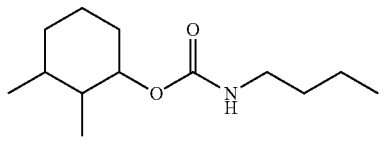 [SMILES: CCCCNC(=O)OC1CCCC(C)C1C]

main signals of isomer mixture:
$^1$H-NMR (400 MHz, CDCl$_3$, TMS): δ=4.66 (m, 2 H), 3.17 (q, 6.3 Hz, 2 H), 2.05 (m, H), 1.24-1.80 (m, 11 H), 0.92 (t, 7.3 Hz, 3 H), 0.89 (d, 6.6 Hz, 3 H), 0.79 (d, 6.9 Hz, 3 H) ppm.
$^{13}$C-NMR (400 MHz, CDCl$_3$, TMS): δ=156.8 (s), 76.3 (d), 40.6 (t), 37.4 (d), 34.8 (t), 34.2 (t), 32.2 (t), 27.4 (t), 25.6 (t), 20.0 (t), 19.1 (q), 13.8 (q), 6.1 (q) ppm.
MS (EI, major isomer): m/z=227(<1), 118 (100), 111 (49), 110 (88), 95 (53), 81 (55), 69 (83), 57 (35), 55 (54), 41 (35).

EXAMPLES 1.2

Unsubstituted Cyclohexyl Carbamates of Formula (Carb-II-R1H)

EXAMPLE 1.2.1

Phenyl-Carbamic Acid Cyclohexyl Ester (BIO1741)

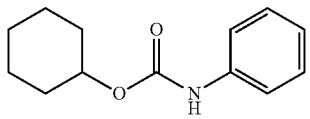 [SMILES: O=C(Nc1ccccc1)OC1CCCCC1]

$^1$H-NMR (400 MHz, CDCl$_3$, TMS): δ=7.38 (m, 2 H), 7.30 (m, 3 H), 7.05 (m, H), 6.51 (m, H), 4.76 (t,t, 3.9 Hz, 9.0 Hz, H), 1.94 (m, 2 H), 1.75 (m, 2 H), 1.56 (m, H), 1.42 (m, 4 H), 1.27 (m, H) ppm.
$^{13}$C-NMR (400 MHz, CDCl$_3$, TMS): δ=153.2 (s), 138.1 (s), 129.0 (d), 129.0 (d), 123.2 (d), 118.5 (d), 118.5 (d), 73.7 (d), 31.9 (t), 31.9 (t), 25.4 (t), 23.8 (t), 23.8 (t) ppm.
MS (EI): m/z=220 (4), 219 (25), 137 (59), 132 (15), 119 (30), 93 (100), 83 (54), 67 (24), 55 (83), 41 (40).

EXAMPLES 1.3

Mono-Substituted Cyclohexyl Carbamates of Formula (Carb-II-R1H)

EXAMPLE 1.3.1 p-Tolyl-carbamic acid 2-isopropyl-cyclohexyl ester (BIO1824)

75.6 g (0.56 mol) of para-tolylisocyanate were placed with 500 ml toluene in a one litre vessel and subsequently 73.4 g (0.51 mol) of 2-isopropylcyclohexanol were added. The reaction mixture was heated to reflux for 6 hours. After cooling to room temperature 50 g of water were added and the mixture was refluxed for one more hour. After phase separation the solvent was stripped off and the crude product recrystallized from 235 g of n-heptane. The product (79.8 g) was obtained in form of off-white crystals in 99.2% purity. This corresponds to a theoretical yield of 56%.

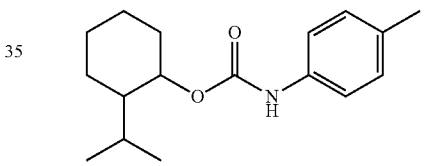

main signals of isomer mixture:
$^1$H-NMR (400 MHz, CDCl$_3$, TMS): δ=7.28 (m, 2 H), 7.10 (m, 2 H), 6.50 (m, H), 5.19 (m, H); 2.30 (s, 3 H), 2.07 (m, H), 1.70-1.81 (m, 2 H), 1.22-1.55 (m, 6 H), 1.07 (m, H), 0.92 (d, 6.7 Hz, 3 H), 0.90 (d, 6.7 Hz, 3 H) ppm.
$^{13}$C-NMR (400 MHz, CDCl$_3$, TMS): δ=153.4 (s), 135.6 (s), 132.7 (s), 129.5 (d), 129.5 (d), 118.6 (d), 118.6 (d), 71.7 (d), 47.2 (d), 30.9 (t), 29.5 (d), 26.0 (t), 25.1 (t), 20.8 (q), 20.7 (q), 20.7 (q), 20.4 (t) ppm.
MS (EI): m/z=276 (5), 275 (30), 151 (89), 125 (17), 107 (100), 83 (32), 69 (74), 57 (21), 41 (18).

EXAMPLE 1.3.2

Butyl-carbamic acid 2-isopropyl-cyclohexyl ester (BIO1841)

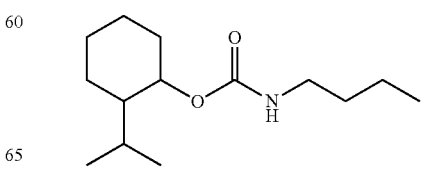

main signals of isomer mixture:

¹H-NMR (400 MHz, CDCl₃, TMS): δ=5.06 (m, H), 4.65 (m, H), 3.17 (q, 6.4 Hz, 2 H), 2.01 (t, 13.8 Hz, H), 1.74 (m, H), 1.68 (d, 10.3 Hz, H), 1.41-1.53 (m, 3 H), 1.35 (m, 2 H), 1.26 (m, H), 1.24 (m, H), 1.02 (m, H), 0.93 (t, 7.3 Hz, 3 H), 0.90 (d, 6.5 Hz, 6 Hz) ppm.

¹³C-NMR (400 MHz, CDCl₃, TMS): δ=156.5 (s), 70.8 (d), 47.2 (d), 40.7 (t), 32.2 (t), 31.1 (t), 29.5 (d), 26.1 (t), 25.0 (t), 20.8 (q), 20.7 (q), 20.5 (t), 19.9 (t), 13.8 (q) ppm.

MS (EI, major isomer): m/z=241 (<1), 198 (2), 124 (84), 118 (100), 109 (36), 99 (26), 81 (64), 69 (71), 57 (61), 41 (37).

MS (EI, minor isomer): m/z=241 (<1), 198 (1), 124 (100), 118 (97), 109 (41), 99 (12), 81 (65), 69 (71), 57 (61), 41 (41).

EXAMPLE 1.3.3

(2-Methoxy-phenyl)-carbamic acid 2-isopropyl-cyclohexyl ester (BIO1744)

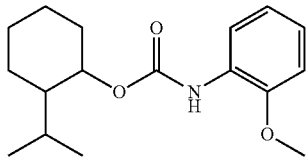 [SMILES: COc1ccccc1NC(=O)OC1CCCCC1C(C)C]

main signals of isomer mixture:

¹H-NMR (400 MHz, CDCl₃, TMS): δ=8.12 (m, H), 7.18 (d, 7.4 Hz, H), 6.98 (m, H), 6.95 (m, H), 6.85 (m, H), 5.21 (m, H), 3.88 (s, 3 H), 2.04-2.15 (m, 2 H), 1.15-1.82 (m, 7 H), 1.08 (m, H), 0.92 (d, 6.9 Hz, 3 H), 0.92 (d, 7.0 Hz, 3 H) ppm.

¹³C-NMR (400 MHz, CDCl₃, TMS): δ=153.3 (s), 147.4 (s), 128.0 (s), 122.5 (d), 121.1 (d), 118.0 (d), 109.9 (d), 71.6 (d), 55.6 (q), 47.2 (d), 30.9 (t), 29.4 (t), 26.0 (t), 25.1 (t), 20.8 (q), 20.8 (q), 20.4 (t) ppm.

MS (EI, major isomer): m/z=292 (3), 291 (21), 167 (45), 123 (100), 108 (46), 81 (46), 69 (87), 55 (29), 41 (36).

MS (EI, minor isomer): m/z=292 (3), 291 (21), 167 (43), 123 (100), 108 (38), 81 (35), 69 (76), 55 (25), 41 (32).

EXAMPLE 1.3.4

(2-Methyl-cyclohexyl)-carbamic acid 4-tert-butyl-cyclohexyl ester (BIO1690)

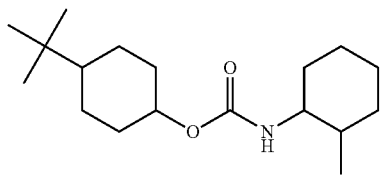 [SMILES: CC1CCCCC1NC(=O)OC1CCC(C(C)(C)C)CC1]

main signals of isomer mixture:

¹H-NMR (400 MHz, CDCl₃, TMS): =4.50 (m, 2 H), 3.15 (m, H), 2.05 (m, 2 H), 1.79 (m, 2 H), 1.72 (m, 2 H), 0.99-1.38 (m, 12 H), 0.94 (d, 6.4 Hz, 3 H), 0.85 (s, 9 H) ppm.

¹³C-NMR (400 MHz, CDCl₃, TMS): =156.0 (s), 73.7 (d), 55.8 (d), 47.2 (d), 38.9 (d), 34.4 (t), 34.1 (t), 34.1 (t), 32.6 (t), 32.6 (t), 32.3 (s), 27.6 (q), 27.6 (q), 27.6 (q), 25.5 (t), 25.5 (t), 25.5 (t), 19.1 (q) ppm.

MS (EI): m/z=296 (1), 295 (3), 238 (1), 158 (100), 139 (32), 96 (58), 83 (30), 70 (17), 57 (56), 41 (17).

EXAMPLE 1.3.5

(2-Hydroxy-phenyl)-carbamic acid 2-isopropyl-cyclohexyl ester (BIO1646)

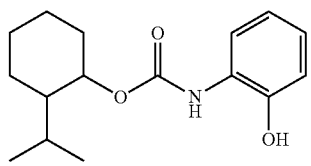

main signals of isomer mixture:

¹H-NMR (400 MHz, CDCl₃, TMS): =8.00 (m, H), 7.19 (d, 7.8 Hz, H), 7.04 (d, d, 7.3 Hz, 8.1 Hz, H), 6.96 (d, 8.1 Hz, 1 H), 6.88 (d,d, 7.3 Hz, 7.9 Hz, H), 6.81 (m, H), 5.22 (m, H), 2.08 (d, 13.1 Hz, H), 1.35-1.55 (m, 4 H), 1.30 m, 2 H), 1.09 (m, H), 0.93 (d, 6.5 Hz, 3 H), 0.91 (d, 6.5 Hz, 3 H) ppm.

¹³C-NMR (400 MHz, CDCl₃, TMS): =155.4 (s), 147.3 (s), 125.7 (d), 125.4 (s), 121.3 (d), 129.9 (d), 118.8 (d), 73.4 (d), 47.1 (d), 30.8 (t), 29.4 (d), 25.9 (t), 25.0 (t), 20.8 (q), 20.7 (q), 20.3 (t) ppm.

MS (EI): m/z=278 (1), 277 (5), 153 (100), 124 (20), 109 (82), 83 (34), 69 (84), 55 (29), 41 (27).

EXAMPLE 1.3.6

Phenyl-carbamic acid 2-tert-butyl-cyclohexyl ester (BIO1740)

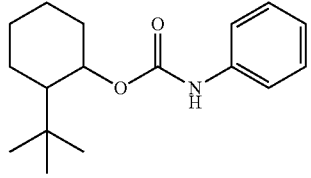 [SMILES: CC(C)(C)C1CCCCC1OC(=O)Nc1ccccc1]

main signals of isomer mixture:

¹H-NMR (400 MHz, CDCl₃, TMS): =7.41 (m, 2 H), 7.30 (m, 2 H), 7.05 (m, H), 6.57 (m, H), 5.32 (m, H), 2.04 (d, 13.6 Hz, H), 1.84 (d, 12.7 Hz, H), 1.67 (d, 12.7 Hz, H), 1.21-1.56 (m, 5 H), 1.17 (d, 12.6 Hz, H), 0.91 (s, 9 H) ppm.

¹³C-NMR (400 MHz, CDCl₃, TMS): =153.0 (s), 138.2 (s), 129.0 (d), 129.0 (d), 123.2 (d), 11.8 (d), 118.5 (d), 72.0 (d), 50.2 (d), 32.6 (s), 31.8 (t), 28.5 (q), 28.5 (q), 28.5 (q), 26.6 (t), 22.3 (t), 20.7 (t) ppm.

MS (EI, major isomer): m/z=276 (1), 275 (6), 123 (32), 93 (71), 83 (39), 67 (18), 57 (100), 41 (25).

MS (EI, minor isomer): m/z=276 (1), 275 (7), 123 (25), 93 (69), 83 (34), 67 (22), 57 (100), 41 (30).

EXAMPLE 1.3.7 p-Tolyl-carbamic acid 3-methyl-cyclohexyl ester (BIO1825)

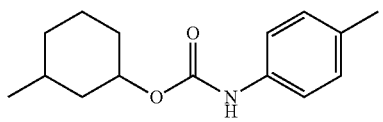

main signals of isomer mixture:

$^1$H-NMR (400 MHz, CDCl$_3$, TMS): =7.25 (m, 2 H), 7.09 (m, 2 H), 6.51 (m, H), 4.67 (t,t, 4.3 Hz, 11.2 Hz, H), 2.30 (s, 3 H), 2.04 (d, 12.2 Hz, 2 H), 1.78 (d, 13.3 Hz, H), 1.63 (d, 13.1 Hz, H), 1.51 (m, H), 1.35 (t,q, 3.6 Hz, 13.1 Hz, H), 1.22 (d,d,d, 11.2 Hz, 11.9 Hz, 13.3 Hz, H), 0.99 (d,t, 11.5 Hz, 12.0 Hz, H), 0.93 (d, 6.5 Hz, 3 H), 0.82 (d,t, 11.9 Hz, 12.9 Hz, H) ppm.

$^{13}$C-NMR (400 MHz, CDCl$_3$, TMS): =153.3 (s), 135.5 (s), 132.7 (s), 129.5 (d), 129.5 (d), 118.7 (d), 118.7 (d), 74.1 (d), 40.9 (t), 34.0 (t), 31.9 (t), 31.4 (d), 24.0 (t), 22.3 (q), 20.7 (q) ppm.

MS (EI): m/z=248 (7), 247 (45), 151 (100), 133 (13), 107 (71), 106 (22), 97 (33), 55 (64), 41 (11).

EXAMPLES 1.4

Tri-Substituted Cyclohexyl Carbamates of Formula (Carb-II-R1H)

EXAMPLE 1.4.1 n-Butyl-carbamic acid 2,3,6-trimethyl-cyclohexyl ester (BIO1617)

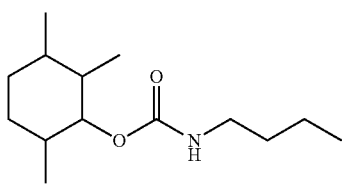

main signals of isomer mixture:

$^1$H-NMR (400 MHz, CDCl$_3$, TMS): δ=4.72 (m, H), 4.15 (t, 10.2 Hz, H), 3.18 (m, 2 H), 1.92 (m, H), 1.49 (m, 2 H), 1.35 (m, 2 H), 0.92-1.78 (m, 6 H), 0.85-0.95 (m, 12 H) ppm.

$^{13}$C-NMR (400 MHz, CDCl$_3$, TMS): δ=157.4 (s), 82.7 (d), 40.7 (t), 40.6 (d), 36.6 (d), 34.6 (t), 32.9 (t), 32.2 (t), 20.0 (q), 19.9 (d), 19.9 (t), 18.6 (q), 15.1 (q), 13.8 (q) ppm.

MS (EI, major): m/z=241 (8), 198 (5), 124 (73), 118 (100), 109 (39), 95 (31), 82 (31), 69 (65), 55 (23), 41 (22).

EXAMPLE 1.4.2

(2-Methoxy-phenyl)-carbamic acid 2,3,6-trimethyl-cyclohexyl ester (BIO1701)

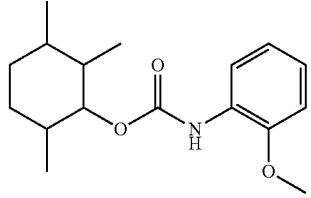 [SMILES: COc1ccccc1NC(=O)OC1C(C)CCC(C)C1C]

main signals of isomer mixture:

$^1$H-NMR (400 MHz, CDCl$_3$, TMS): δ=8.13 (m, H), 7.24 (m, H), 6.92-7.00 (m, 2 H), 6.85 (m, H), 4.29 (t, 10.0 Hz, H), 3.86 (s, 3 H), 0.99-1.76 (m, 7 H), 0.94 (d, 6.4 Hz, 6 H), 0.94 (d, 6.6 Hz, 3H) ppm.

$^{13}$C-NMR (400 MHz, CDCl$_3$, TMS): δ=154.0 (s), 147.5 (s), 128.1 (s), 122.4 (d), 121.1 (d), 118.0 (d), 109.9 (d), 83.4 (d), 55.6 (q), 44.4 (d), 38.1 (d), 37.8 (d), 34.6 (t), 32.9 (t), 20.0 (q), 18.6 (q), 15.2 (q) ppm.

MS (EI, major isomer): m/z=291 (50), 190 (5), 167 (55), 150 (12), 123 (100), 108 (25), 83 (19), 69 (57), 55 (21), 41 (14).

EXAMPLE 1.4.3 sec-Butyl-carbamic acid 3,3,5-trimethyl-cyclohexyl ester (BIO1844)

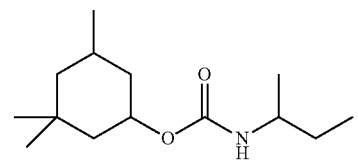 [SMILES: CCC(C)NC(=O)OC1CC(C)CC(C)(C)C1]

main signals of isomer mixture:

$^1$H-NMR (400 MHz, CDCl$_3$, TMS): δ=4.75 (t,t, 4.1 Hz, 11.5 Hz, H), 4.38 (m, H), 3.60 (m, H), 2.00 (d, 11.4 Hz, H), 1.70 (d, 12.3 Hz, H), 1.66 (m, H), 1.43 (m, 2 H), 1.31 (d, 13.2 Hz, H), 1.10 (d, 6.8 Hz, 3 H), 1.04 (m, H), 0.93 (s, 6 H), 0.89 (t, 7.5 Hz, 3 H), 0.89 (d, 6.5 Hz, 3 H), 0.80 (m, H), 0.76 (t, 12.5 HZ, H) ppm.

$^{13}$C-NMR (400 MHz, CDCl$_3$, TMS): δ=155.8 (s), 71.1 (d), 48.2 (d), 47.6 (t), 44.4 (t), 41.0 (t), 33.1 (q), 32.2 (s), 30.0 (t), 27.1 (d), 25.6 (q), 22.3 (q), 20.7 (q), 10.3 (q) ppm.

MS (EI, major isomer): m/z=241 (not detected), 226 (<1), 212 (38), 168 (28), 125 (35), 109 (23), 83 (39), 69 (100), 57 (31), 44 (86), 41 (32).

EXAMPLE 1.4.4 n-Butyl-carbamic acid 3,3,5-trimethyl-cyclohexyl ester (BIO1616)

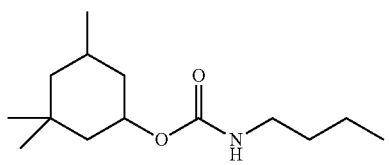 [SMILES: CCCCNC(=O)OC1CC(C)CC(C)(C)C1]

main signals of isomer mixture:

$^1$H-NMR (400 MHz, CDCl$_3$, TMS): δ=4.77 (t,t, 4.1 Hz, 11.6 Hz, H), 4.64 (m, H), 3.16 (q, 6.3 Hz, 2 H), 2.01 (d, 11.6 Hz, H), 1.63-1.75 (m, 3 H), 1.47 (m, 2 H), 1.29-1.39 (m, 3 H), 1.03 (m, H), 0.94 (s, 6 H), 0.92 (t, 7.3 Hz, 3 H), 0.90 (d, 6.5 Hz, 3 H), 0.71-0.85 (m, 2 H) ppm.

$^{13}$C-NMR (400 MHz, CDCl$_3$, TMS): δ=156.4 (s), 71.2 (d), 47.6 (t), 44.4 (t), 40.9 (t), 40.6 (t), 33.1 (q), 32.2 (t), 32.1 (s), 27.1 (d), 25.5 (q), 22.3 (q), 19.9 (t), 13.7 (q) ppm.

MS (EI): m/z=242 (<1), 241 (<1), 125 (17), 118 (100), 109 (36), 83 (29), 69 (57), 57 (18), 55 (17), 41 (21).

EXAMPLE 1.4.5

(2-Methoxy-phenyl)-carbamic acid 3,3,5-trimethyl-cyclohexyl ester (BIO1703)

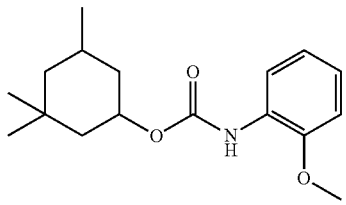

main signals of isomer mixture:

$^1$H-NMR (400 MHz, CDCl$_3$, TMS): δ=8.09 (m, H), 7.17 (m, H), 6.96 (m, 2 H), 6.84 (m, H), 4.89 (t,t, 4.4 Hz, 11.6 Hz, H), 3.85 (s, 3 H), 2.08 (d, 12.0 Hz, H), 1.78 (d, 12.1 Hz, H), 1.73 (m, H), 1.35 (d, 13.2 Hz, H), 1.14 (t, 12.0 Hz, H), 0.97 (s, 3 H), 0.96 (s, 3 H), 0.92 (d, 6.5 Hz, 3 H), 0.90 (m, H), 0.80 (t, 12.7 Hz, H) ppm.

$^{13}$C-NMR (400 MHz, CDCl$_3$, TMS): δ=153.2 (s), 147.5 (s), 127.9 (s), 122.5 (d), 121.1 (d), 118.1 (d), 109.9 (d), 71.9 (d), 55.6 (q), 47.6 (t), 44.3 (t), 40.8 (t), 33.1 (q), 32.3 (s), 27.1 (d), 25.5 (q), 22.3 (q) ppm.

MS (EI): m/z=292 (12), 291 (62), 167 (53), 123 (100), 108 (31), 83 (18), 69 (52), 55 (17), 41 (19).

EXAMPLE 1.4.6 n-Hexyl-carbamic acid 3,3,5-trimethyl-cyclohexyl ester (BIO1850)

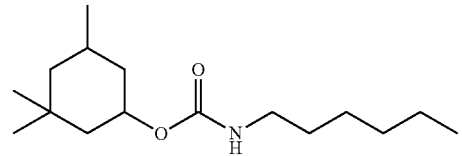 [SMILES: CCCCCCNC(=O)OC1CC(C)CC(C)(C)C1]

main signals of isomer mixture:

$^1$H-NMR (400 MHz, CDCl$_3$, TMS): δ=4.77 (t, 11.5 Hz, H), 4.62 (m, H), 3.15 (q, 6.5 Hz, 2 H), 2.00 (d, 11.4 Hz, H), 1.62-1.75 (m, 2 H), 1.47 (m, 2 H), 1.24-1.35 (m, 8 H), 1.04 (m, H), 0.94 (s, 6 H), 0.90 (d, 6.4 Hz, H), 0.88 (t, 6.9 Hz, 3 H), 0.76 (m, H) ppm.

$^{13}$C-NMR (400 MHz, CDCl$_3$, TMS): δ=156.4 (s), 71.2 (d), 47.6 (t), 44.5 (t), 41.0 (t), 41.0 (t), 33.1 (q), 32.2 (s), 31.5 (t), 30.0 (t), 27.1 (d), 26.4 (t), 25.6 (q), 22.6 (t), 22.3 (q), 14.0 (q) ppm.

MS (EI, minor isomer): m/z=270 (<1), 269 (1), 146 (100), 125 (16), 109 (35), 83 (36), 69 (82), 55 (23), 41 (32), 30 (24).

MS (EI, major isomer): m/z=270 (<1), 269 (1), 146 (100), 125 (28), 109 (34), 83 (39), 69 (89), 55 (23), 41 (28), 30 (24).

EXAMPLE 1.4.7

Ethyl-carbamic acid 1,7,7-trimethyl-bicyclo[2.2.1]hept-2-yl ester (BIO1573)

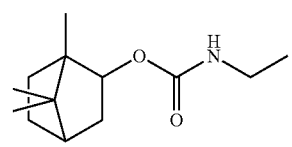 [SMILES: CCNC(=O)OC1CC2CCC1(C)C2(C)C]

main signals of isomer mixture:

$^1$H-NMR (400 MHz, CDCl$_3$, TMS): δ=4.83 (d,d,d, 10.0 Hz, 3.4 Hz, 2.0 Hz, H), 4.63 (m, H), 3.22 (d,q, 5.9 Hz, 7.2 Hz, 2H), 2.33 (m, H), 1.88 (m, H), 1.73 (m, H), 1.66 (m, H), 1.17-1.32 (m, 2 H), 1.15 (t, 7.2 Hz, 3 H), 1.01 (m, H), 0.90 (s, 3 H), 0.86 (s, 3 H), 0.84 (s, 3 H) ppm.

$^{13}$C-NMR (400 MHz, CDCl$_3$, TMS): δ=157.0 (s), 79.9 (d), 48.7 (s), 47.8 (s), 44.9 (d), 36.9 (t), 35.8 (t), 28.1 (t), 27.1 (t), 19.8 (q), 18.8 (q), 15.3 (q), 13.5 (q) ppm.

MS (EI): m/z=226 (2), 225 (12), 136 (49), 121 (34), 108 (21), 95 (100), 55 (12), 41 (19), 29 (13).

EXAMPLE 1.4.8

(3-Methoxy-propyl)-carbamic acid 3,3,5-trimethyl-cyclohexyl ester (BIO1574)

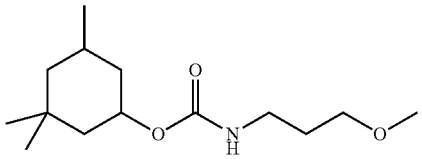

main signals of isomer mixture:

$^1$H-NMR (400 MHz, CDCl$_3$, TMS): =4.94 (m, H), 4.76 (t,t, 4.3 Hz, 11.6 Hz, H), 3.35 (t, 5.9 Hz, 2 H), 3.33 (s, 3 H), 3.27 (q, 5.9 Hz, 2 H), 2.00 (d, 12.3 Hz, H), 1.76 (q, 6.2 Hz, 2 H), 1.62-1.74 (m, 2 H), 1.32 (d, 13.1 Hz, H), 1.03 (m, H), 0.94 (s, 6 H), 0.90 (d, 6.6 Hz, 3 H), 0.78 (m, 2 H) ppm.

$^{13}$C-NMR (400 MHz, CDCl$_3$, TMS): =156.4 (s), 71.3 (d), 71.1 (t), 58.7 (q), 47.6 (t), 44.5 (t), 41.0 (t), 39.0 (t), 33.1 (q), 32.2 (s), 29.7 (t), 27.1 (d), 25.6 (q), 22.3 (q) ppm.

MS (EI, minor isomer): m/z=257 (2), 242 (1), 109 (100), 101 (35), 90 (48), 69 (96), 55 (39), 45 (39), 41 (63), 30 (37).

MS (EI, major isomer): m/z=257 (3), 242 (1), 109 (65), 101 (34), 83 (53), 69 (100), 55 (33), 45 (44), 41 (57), 30 (33).

EXAMPLE 1.4.9

(2-Hydroxy-phenyl)-carbamic acid 3,3,5-trimethyl-cyclohexyl ester (BIO1642)

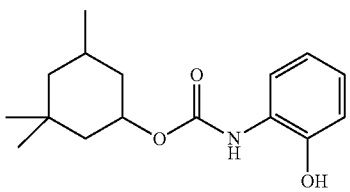 [SMILES: CC1CC(OC(=O)Nc2ccccc2O)CC(C)(C)C1]

main signals of isomer mixture:

$^1$H-NMR (400 MHz, CDCl$_3$, TMS): =7.90 (m, H), 7.20 (d, 8.0 Hz, H), 7.03 (d,d, 8.1 Hz, 7.3 Hz, H) 6.95 (d, 8.1 Hz, H), 6.86 (d,d, 7.2 Hz, 7.9 Hz, H), 6.80 (m, H), 4.89 (t, t, 4.4 Hz, 11.6 Hz, H), 2.08 (d, 11.8 Hz, H), 1.65-1.83 (m, 3 H), 1.36 (d, 13.2 Hz, H), 1.15 (t, 12.0 Hz, H), 0.97 (s, 3 H), 0.96 (s, 3 H), 0.93 (d, 6.6 Hz, 3 H), 0.80 (t, 12.7 Hz, H) ppm.

$^{13}$C-NMR (400 MHz, CDCl$_3$, TMS): =155.2 (s), 147.2 (s), 125.6 (s), 125.5 (d), 121.2 (d), 120.8 (d), 118.5 (d), 73.5 (d), 47.5 (t), 44.2 (t), 40.6 (t), 22.0 (q), 32.3 (s), 27.1 (d), 25.5 (q), 22.3 (q) ppm.

MS (EI): m/z=278 (2), 277 (9), 153 (100), 109 (83), 83 (22), 69 (75), 55 (25), 41 (29).

EXAMPLE 1.4.10

Ethyl-carbamic acid 3,3,5-trimethyl-cyclohexyl ester (BIO1572)

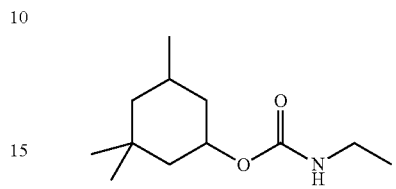

$^1$H-NMR (400 MHz, CDCl$_3$, TMS): =0.70-0.87 (m, 2 H), 0.90 (d, J=6.5 Hz, 3 H), 0.94 (s, 6 H), 0.95-1.16 (m, 2 H), 1.13 (t, J=7.2 Hz, 3 H), 1.29-1.36 (m, 1 H), 1.62-1.76 (m, 1 H), 2.01 (d, br., J=11 Hz, 1 H), 3.14-3.25 (m, 2 H), 4.57 (s, br., 1 H), 4.71-4.83 (m, 1 H) ppm.

$^{13}$C-NMR (400 MHz, CDCl$_3$, TMS): =15.30 (CH$_3$), 22.32 (CH$_3$), 25.56 (CH$_3$), 27.10 (CH), 32.23 (C), 33.07 (CH$_3$), 35.72 (CH$_2$), 40.95 (CH$_2$), 44.46 (CH$_2$), 47.61 (CH$_2$), 71.23 (CH), 156.28 (CO) ppm.

MS (EI): m/z=214 (1), 141 (4), 124 (12), 109 (52), 95 (9), 90 (100), 83 (19), 69 (34), 55 (11).

EXAMPLES 1.5

N,N-Dialkyl cyclohexyl carbamates of formula (Carb-II)

EXAMPLE 1.5.1

Diethyl-carbamic acid 2,3,6-trimethyl-cyclohexyl ester (BIO1692)

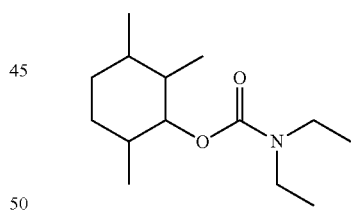

4.27 g (30 mmol) of 2,3,6-trimethylcyclohexanol were placed with 110 ml dichlormethane in a 250 ml vessel at room temperature and 3.08 g (39 mmol) of pyridine were added. The reaction mixture was cooled to 0° C. and 3.56 g (12 mmol) of triphosgene in 15 ml dichlormethane were added dropwise. After five minutes 2.37 g (30 mmol) pyridine were added. Subsequently, 2.19 g (30 mmol) of diethylamine in 15 ml dichlormethane were added dropwise, the resulting mixture was allowed to come to ambient temperature and then quenched with water. After separation of the phases, the water phase was extracted once with dichlormethane and the combined organic phases were concentrated. The raw product was purified by distillation and column chromatography to yield 1.5 g of the desired product as a mixture of isomers with a purity of 99.4%.

Main signals of isomer mixture:

$^1$H-NMR (400 MHz, CDCl$_3$, TMS): δ=4.48 (t, 10.3 Hz, H), 3.29 (q, 4.8 Hz, 4 H), 1.92 (m, H), 1.70 (m, H), 1.44-1.65 (m, 4 H), 1.35 (m, H), 1.12 (t, 7.2 Hz, 6 H), 0.91 (d, 7.4 Hz, 6 H), 0.89 (d, 6.9 Hz, 3 H) ppm.

$^{13}$C-NMR (400 MHz, CDCl$_3$, TMS): δ=156.5 (s), 79.4 (d), 41.8 (t), 41.0 (t), 40.6 (d), 39.0 (d), 34.6 (d), 32.6 (t), 28.7 (t), 18.5 (q), 15.9 (q), 14.4 (q), 13.6 (q), 12.9 (q) ppm.

MS (EI, major isomer): m/z=242 (2), 241 (O), 124 (21), 118 (100), 100 (16), 83 (22), 69 (56), 55 (13), 41 (10).

EXAMPLE 1.5.2

Diethyl-carbamic acid 2-isopropyl-cyclohexyl ester (BIO1694)

BIO1694 was produced analogously to the methodology as described for BIO1692 in example 1.5.1 and obtained in comparable yield and puritiy (>99%) as a mixture of stereoisomers.

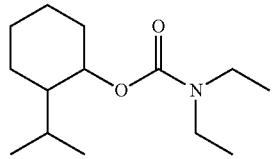 [SMILES: CCN(CC)C(=O)OC1CCCCC1C(C)C]

main signals of isomer mixture:

$^1$H-NMR (400 MHz, CDCl$_3$, TMS): δ=5.10 (m, H), 3.28 (m, 4 H), 2.01 (m, H), 1.66-1.81 (m, 3 H), 0.99-1.52 (m, 6 H), 1.13 (t, 7.1 Hz, 6 H), 0.90 (d, 6.7 Hz, 3 H), 0.89 (d, 6.7 Hz, 3 H) ppm.

$^{13}$C-NMR (400 MHz, CDCl$_3$, TMS): δ=155.6 (s), 70.9 (d), 47.6 (d), 41.3 (t), 41.3 (t), 31.0 (t), 29.7 (d), 26.2 (t), 25.5 (t), 20.9 (q), 20.7 (q), 20.7 (t), 14.1 (q), 14.1 (q) ppm.

MS (EI): m/z=242 (2), 241 (8), 124 (82), 118 (100), 100 (28), 83 (48), 69 (97), 57 (29), 41 (17).

EXAMPLE 2

Depigmenting Effect on Melanoma Cell Cultures

B16V mouse melanoma cells are disseminated in a 96-well microtitre plate in a concentration of 5×10$^3$ cells/well. After cultivation for 24 h at 37° C. and 5% CO$_2$ in RPMI medium, enriched with 10% foetal calf serum, various concentrations of the test substances and 0.3 mM tyrosine and 10 nM α-MSH (α-melanocyte stimulating hormone) are added and incubated for a further 96 h. The maximum concentration of the test substances used corresponds to 0.1 times the value of the IC$_{20}$ value of the cytotoxicity assay. Standards are incubated with kojic acid in concentrations of 0.01 mM, 0.1 mM and 1 mM in addition to tyrosine and α-MSH. Only tyrosine and α-MSH are added to the controls. After incubation, sodium lauryl sulfate and sodium hydroxide solution (final concentrations: 1 mM and 1 M respectively) are added to the culture medium and the absorption (A) is measured after 3 h at 400 nm.

The inhibition of pigmentation in the presence of the test compounds or kojic acid was calculated using the following equation:

Inhibition of pigmentation (%)=100−[($A_{test\ compound}$/$A_{control}$)×100]

wherein $A_{test\ compound}$=absorption of the wells with test substance and with cells $A_{control}$=absorption of the wells without test substance, but with cells From the inhibition of pigmentation (%) in a series of dilutions of test compounds, the IC$_{50}$ for each test compound is calculated. This is the concentration of a test compound at which pigmentation is inhibited by 50%.

TABLE 2

| | test substance | IC50 [μM] |
|---|---|---|
| reference | Kojic acid | 452.3 |
| reference | beta-Arbutin | 67.0 |
| BIO1741 | Phenyl-carbamic acid cyclohexyl ester | 12.9 |
| BIO1841 | Butyl-carbamic acid 2-isopropyl-cyclohexyl ester tested as following mixture of isomeres: 79% Butyl-carbamic acid (1R*,2R*)-2-isopropyl-cyclohexyl ester 20% Butyl-carbamic acid (1R*,2S*)-2-isopropyl-cyclohexyl ester | 28.5 |
| BIO1744 | (2-Methoxy-phenyl)-carbamic acid 2-isopropyl-cyclohexyl ester | 18.3 |
| BIO1824 | p-Tolyl-carbamic acid 2-isopropyl-cyclohexyl ester tested as following mixture of isomers: 92% (1S*,2S*)-2-(1-methylethyl)cyclohexyl (4-methylphenyl)carbamate 8% (1S*,2R*)-2-(1-methylethyl)cyclohexyl (4-methylphenyl)carbamate | 4.7 |
| BIO1646 | (2-Hydroxy-phenyl)-carbamic acid 2-isopropyl-cyclohexyl ester | 4.7 |
| BIO1694 | Diethyl-carbamic acid 2-isopropyl-cyclohexyl ester | 38.5 |
| BIO1740 | Phenyl-carbamic acid 2-tert-butyl-cyclohexyl ester | 5.5 |
| BIO1690 | (2-Methyl-cyclohexyl)-carbamic acid 4-tert-butyl-cyclohexyl ester | 10.9 |
| BIO1825 | p-Tolyl-carbamic acid 3-methyl-cyclohexyl ester | 72.5 |
| BIO1707 | (4,4-Diethoxy-butyl)-carbamic acid 4-propyl-cyclohexyl ester | 12.7 |
| BIO1842 | Butyl-carbamic acid 2,3-dimethyl-cyclohexyl ester | 94.1 |
| BIO1840 | Butyl-carbamic acid 3,5-dimethyl-cyclohexyl ester | 89.5 |
| BIO1561 | Ethyl-carbamic acid 3,5-dimethyl-cyclohexyl ester tested as following mixture of isomeres: 61.8% Ethyl carbamic acid (1alpha,3alpha,5alpha)-3,5-dimethyl-cyclohexylester 27.6% Ethyl carbamic acid (1alpha,3beta,5beta)-3,5-dimethyl-cyclohexylester 9.9% Ethyl carbamic acid (1alpha*,3alpha*,5beta*)-3,5-dimethyl-cyclohexylester | 32.7 |
| BIO1643 | (2-Hydroxy-phenyl)-carbamic acid 2,3-dimethyl-cyclohexyl ester | 0.7 |
| BIO1685 | Phenyl-carbamic acid 3,5-dimethyl-cyclohexyl ester tested as following mixture of isomeres: 94% Phenyl-carbamic acid (1alpha,3alpha,5alpha)-3,5-dimethyl-cyclohexyl ester + Phenyl-carbamic acid (1alpha*,3alpha*,5beta*)-3,5-dimethyl-cyclohexyl ester 5% Phenyl-carbamic acid (1alpha,3beta,5beta)-3,5-dimethyl-cyclohexyl ester | 18.9 |
| BIO1822 | p-Tolyl-carbamic acid 3,5-dimethyl-cyclohexyl ester tested as following mixture of isomers: 81% p-Tolyl-carbamic acid (1alpha,3alpha,5alpha)-3,5-dimethyl-cyclohexyl ester + p-Tolyl-carbamic acid (1alpha*,3alpha*,5beta*)-3,5-dimethyl-cyclohexyl ester 19% p-Tolyl-carbamic acid (1alpha,3beta,5beta)-3,5-dimethyl-cyclohexyl ester | 52.5 |
| BIO1617 | Butyl-carbamic acid 2,3,6-trimethyl-cyclohexyl ester | 15.4 |
| BIO1701 | (2-Methoxy-phenyl)-carbamic acid 2,3,6-trimethyl-cyclohexyl ester | 10.2 |
| BIO1692 | Diethyl-carbamic acid 2,3,6-trimethyl-cyclohexyl ester | 41.7 |
| BIO1844 | sec-Butyl-carbamic acid 3,3,5-trimethyl-cyclohexyl ester tested as following mixture of isomeres: 91% sec-Butyl-carbamic acid (1R*,5R*)-3,3,5-trimethyl-cyclohexyl ester 7% sec-Butyl-carbamic acid (1R*,5S*)-3,3,5-trimethyl-cyclohexyl ester | 219.4 |

TABLE 2-continued

| test substance | | IC50 [µM] |
|---|---|---|
| BIO1616 | Butyl-carbamic acid 3,3,5-trimethyl-cyclohexyl ester tested as following mixture of isomers: 92% Butyl-carbamic acid (1R*,5R*)-3,3,5-trimethyl-cyclohexyl ester 7% Butyl-carbamic acid (1R*,5S*)-3,3,5-trimethyl-cyclohexyl ester | 10.9 |
| BIO1850 | Hexyl-carbamic acid 3,3,5-trimethyl-cyclohexyl ester tested as following mixture of isomers: 90% Hexyl-carbamic acid (1R*,5R*)-3,3,5-trimethyl-cyclohexyl ester 7% Hexyl-carbamic acid (1R*,5S*)-3,3,5-trimethyl-cyclohexyl ester | 14.3 |
| BIO1703 | (2-Methoxy-phenyl)-carbamic acid 3,3,5-trimethyl-cyclohexyl ester tested as following mixture of isomers: 92% (2-Methoxy-phenyl)-carbamic acid (1R*,5R*)-3,3,5-trimethyl-cyclohexyl ester 7% (2-Methoxy-phenyl)-carbamic acid (1R*,5S*)-3,3,5-trimethyl-cyclohexyl ester | 25.1 |
| BIO1572 | Ethyl-carbamic acid 3,3,5-trimethyl-cyclohexyl ester | 63.1 |
| BIO1574 | (3-Methoxy-propyl)-carbamic acid 3,3,5-trimethyl-cyclohexyl ester | 9.5 |
| BIO1642 | (2-Hydroxy-phenyl)-carbamic acid 3,3,5-trimethyl-cyclohexyl ester | 5.6 |
| BIO1573 | Ethyl-carbamic acid (R)-1,7,7-trimethyl-bicyclo[2.2.1]hept-2-yl ester | 74.9 |
| BIO1551 | Ethyl-carbamic acid 2-isopropenyl-5-methyl-cyclohexyl ester | 40.9 |
| BIO1615 | Butyl-carbamic acid 2-isopropenyl-5-methyl-cyclohexyl ester | 43.0 |

These data show that compounds of formula (I) according to the present invention have an up to 90 times stronger depigmenting effect on B16V melanoma cells than kojic acid and an up to 14.9 fold stronger depigmenting effect on B16V melanoma cells than β-arbutin.

EXAMPLE 3

Depigmenting Effect on Ex Vivo Skin

Pigmented pig skin was excised from animals (slaughtered for meat production; the pig skin model included the subcutis fat layer as described in EP 1 939 27), cut into 4×4×3 mm pieces (length×width×height) and placed in culture at the air-liquid interface on a sterilized cotton pad soaked with 5 ml of customized DMEM (Dulbecco's Modified Eagle Medium). Assays were started 24 h after sample acclimatization at 37° C., 5% $CO_2$. O/W emulsions (as described in more detail below) without (=control) and with the test compounds, respectively, were applied topically and incubated for 6 days. Histological sections were prepared and melanin granules stained by Fontana-Masson technique. The granules were quantified by image analysis.

| Test substance | Amount in wt. % | Melanin score vs. Control |
|---|---|---|
| BIO1703 | 0.5% | −37% |
| BIO1824 | 1% | −44% |
| BIO1561 | 1% | −26% |
| BIO1741 | 1% | −28% |
| BIO1643 | 0.5% | −26% |

These data show that compounds of formula (I) according to the present invention have a depigmenting effect per quantity on ex vivo skin.

The O/W emulsions used had the following composition:

| Phase | Ingredient | INCI-Name | % by weight |
|---|---|---|---|
| A | Water | Water (Aqua) | Ad 100 |
|   | Hydrolite-5 | 1,2 Pentylene Glycol | 2.00 |
| B | PCL liquid 100 | Cetearyl Octanoate | 3.00 |
|   | Lanette O | Cetearyl Alcohol | 2.00 |
|   | Paraffin oil 5 °E | Mineral Oil | 3.00 |
|   | Eutanol G | Octyldodecanol | 4.00 |
|   | Abil 350 | Dimethicone | 0.50 |
| C | Pemulen TR1 | Acrylates/C10-30 Alkyl Acrylate Crosspolymer | 0.20 |
|   | Ultrez-21 | Acrylates/C10-30 Alkyl Acrylate Crosspolymer | 0.05 |
| D | Sodium Hydroxide, 10% solution | Sodium Hydroxide | 0.50 |
| E | Compound of formula (I) | | 0.50 or 1.00 wt. %, as indicated above |
|   | Hydrolite-5 | 1,2 Pentylene Glycol | 3.00 |

Manufacturing Procedure:

Phases A and B are heated to 70° C. separately. Pemulen TR1 as well as Ultrez-21 are dispersed in phase B when heated to 70° C. Phase B/C is added to phase A by mixing with an Ultra Turrax, followed by emulsifying. Phase D is slowly added to phase A/B/C using a paddle mixer and a pH 5.5-6 is adjusted. The formulation is cooled down while mixing with a paddle mixer. Phase E is prepared by dissolving one or more compounds of formula (I) in Hydrolite-5. Subsequently, phase E is added to the mixture of phase A-D.

FORMULATION EXAMPLES

"Compound of List A"

Unless indicated otherwise in the respective formulation example, each compound from the following List A was formulated separately into each single formulation of the formulation examples K1-K11 and F1-F10 given below.

List A:
BIO01561, BIO1643, BIO1703, BIO1741, BIO1824, BIO1685, BIO1690, BIO1822, BIO1840, BIO1850, BIO1574, BIO1707, BIO1551, BIO1615 and BIO1694.

Additionally, several formulations were produced including mixtures of two, three of four different compounds selected from list A. In such a case, the amount used in the formulation example refers to the sum of the compounds selected from list A used therein.

In case two different compounds of list A were used as a mixture in the formulation examples given herein, generally the ratio by weight of the two compounds was chosen in the range of from 10:1 to 1:10, preferably in the range of from 5:1 to 1:5, more preferably in the range of from 3:1 to 1:3.

In formulation examples K1-K9 and K11 the following two perfume oils PFO1 and PFO2 were each used as fragrance (DPG=dipropylene glycol).

Perfume Oil PFO1 with Rose Smell

| Component/NAME | Parts by weight |
|---|---|
| Acetophenone, 10% in DPG | 10.00 |
| n-Undecanal | 5.00 |
| Aldehyde C14, so-called (peach aldehyde) | 15.00 |
| Allylamyl glycolate, 10% in DPG | 20.00 |
| Amyl salicylate | 25.00 |
| Benzyl acetate | 60.00 |
| Citronellol | 80.00 |
| d-Limonene | 50.00 |

| Component/NAME | Parts by weight |
|---|---|
| Decenol trans-9 | 15.00 |
| Dihydromyrcenol | 50.00 |
| Dimethylbenzylcarbinyl acetate | 30.00 |
| Diphenyloxide | 5.00 |
| Eucalyptol | 10.00 |
| Geraniol | 40.00 |
| Nerol | 20.00 |
| Geranium oil | 15.00 |
| Hexenol cis-3, 10% in DPG | 5.00 |
| Hexenyl salicylate cis-3 | 20.00 |
| Indole, 10% in DPG | 10.00 |
| Alpha-Ionone | 15.00 |
| Beta-Ionone | 5.00 |
| Lilial ® (2-methyl-3-(4-tert-butyl-phenyl)propanal) | 60.00 |
| Linalool | 40.00 |
| Methylphenyl acetate | 10.00 |
| Phenylethyl alcohol | 275.00 |
| Styrolyl acetate | 20.00 |
| Terpineol | 30.00 |
| Tetrahydrolinalool | 50.00 |
| Cinnamyl alcohol | 10.00 |
| Total: | 1,000.00 |

Perfume Oil PFO2 with White Blossom and Musk Smell

| Component/NAME | Parts by weight |
|---|---|
| Benzyl acetate | 60.00 |
| Citronellyl acetate | 60.00 |
| Cyclamenaldehyde (2-methyl-3-(4-isopropylphenyl)propanal | 20.00 |
| Dipropylene glycol (DPG) | 60.00 |
| Ethyllinalool | 40.00 |
| Florol (2-isobutyl-4-methyltetrahydro-2H-pyran-4-ol) | 30.00 |
| Globanone ® [(E/Z)-8-cyclohexadecen-1-one] | 180.00 |
| Hedione ® (methyldihydrojasmonate) | 140.00 |
| Hexenyl salicylate, cis-3 | 10.00 |
| Vertocitral (2,4-dimethyl-3-cyclohexenecarboxaldehyde) | 5.00 |
| Hydratropaaldehyde, 10% in DPG | 5.00 |
| Isodamascone (1-(2,4,4-trimethyl-2-cyclohexen-1-yl)-2-buten-1-one, 10% in DPG | 5.00 |
| Isomuscone (cyclohexadecanone) | 40.00 |
| Jacinthaflor (2-methyl-4-phenyl-1,3-dioxolane) | 10.00 |
| Cis-jasmone, 10% in DPG | 20.00 |
| Linalool | 50.00 |
| Linalyl acetate | 30.00 |
| Methyl benzoate, 10% in DPG | 25.00 |
| para-Methyl cresol, 10% in DPG | 10.00 |
| Nerol | 20.00 |
| Phenylpropylaldehyde | 5.00 |
| 2-Phenylethyl alcohol | 82.00 |
| Tetrahydrogeraniol | 13.00 |
| 2,2-Dimethyl-3-cyclohexyl-1-propanol | 80.00 |
| Total: | 1,000.00 |

Formulation Examples K1-K11:
Formulations according to the invention with compositions according to Table 1
K1=Skin Care Gel (SPF 6)
K2=Sun Protection Lotion SPF 24 (UVA/UVB Balance)
K3=Tinted Anti Aging Balm, SPF 15
K4=Body Lotion, SPF 15
K5=Skin Soothing Night Cream O/W
K6=Cream W/O
K7=Skin Care Ampoule
K8=Skin Oil
K9=Shower & Shampoo
K10=Tinted Skin Care Stick SPF 50
K11=Hair Gel

TABLE 1

Compositions of formulations according to the invention (Examples K1 - K11)

| Ingredients | INCI-Name | K1 | K2 | K3 | K4 | K5 | K6 | K7 | K8 | K9 | K10 | K11 |
|---|---|---|---|---|---|---|---|---|---|---|---|---|
| Skin Lightening Ingredients | | | | | | | | | | | | |
| Compound of list A | | 0.1 | 5 | 0.05 | 0.2 | 1 | 0.5 | 0.1 | 0.5 | 0.2 | 1 | 0.5 |
| SymWhite 377 (Symrise) | Phenylethyl resorcinol | | 0.5 | | | | | 0.1 | | | | |
| beta-Arbutin | Arbutin | 1 | | | | | 0.5 | | | | 0.2 | |
| Nicotinamide | Niacinamide | | | | | 0.5 | | | | | 1 | |
| Kojic acid | Kojic acid | | | | 0.5 | | | | | | | 1 |
| Mg ascorbyl phosphate | Magnesium ascorbyl phosphate | | | | 5 | | | | | | 3 | |
| Other Ingredients | | | | | | | | | | | | |
| (−) alpha Bisabolol nat. | Bisabolol | | | 0.1 | 0.2 | | | | | | 0.1 | |
| Abil 350 | Dimethicone | | | 2 | | | | | | | | |
| Actipone ® Laminaria SaccharinaGW | Glycerin, Water (Aqua), Laminaria Saccharina Extract | | | | | 1 | | | | | | |
| Aloe Vera Gel Conc.10:1 | Aloe Barbadensis Leaf Juice | | | 1 | | | | | | | | |
| Aluminium Stearate | Aluminium Stearate | | | | | | | | 1.2 | | | |

TABLE 1-continued

Compositions of formulations according to the invention (Examples K1 - K11)

| Ingredients | INCI-Name | K1 | K2 | K3 | K4 | K5 | K6 | K7 | K8 | K9 | K10 | K11 |
|---|---|---|---|---|---|---|---|---|---|---|---|---|
| Amaze XT | Dehydroxanthan Gum | 1.4 | | | | | | | | | | |
| Betulin 90% (1079) | Betulin | | | | | 0.15 | | | | | | |
| Biotive ® L-Arginine | Arginine | 3.2 | 0.5 | 0.6 | 0.9 | | | | | | | |
| Biotive ® Troxerutin | Troxerutin | | 0.5 | 0.5 | | | | | | | | |
| Carbopol ETD 2020 | Acrylates/C10-30 Alkyl Acrylate Crosspolymer | 0.2 | | | | | | | | | | |
| Carbopol ETD 2050 | Carbomer | | | 0.2 | | 0.2 | | | | | | |
| Carbopol Ultrez-21 | Acrylates/C10-30 Alkyl Acrylate Crosspolymer | | | | 0.5 | | | | | | | |
| Citric Acid 10% sol. in water | Citric Acid | | | | | | | | | 3.1 | | |
| Comperlan 100 | Cocamide MEA | | | | | | | | | 1 | | |
| Corapan TQ | Diethylhexyl 2,6 Naphtalate | | | | | 3 | | | | | | |
| Crinipan ® AD | Climbazole | | | | | | | | | | | 0.1 |
| Cutina GMS V | Glyceryl Stearate | | | | | | 2 | | | | | |
| Cutina PES | Pentaerythrityl Distearate | | | 2 | | | | | | | | |
| Cutina TS | PEG-3 Distearate | | | | | | | | | 2.5 | | |
| DC9701 Cosmetic Powder | Dimethicone/Vinyl Dimethicone Crosspolymer, Silica | | | | | | | | | | 2 | |
| Dermacryl AQF | Acrylates Copolymer | | 2 | | | | | | | | | |
| Dipropylene Glycol | Dipropylene Glycol | | | | | | | | | | | 1 |
| Dow Corning 193 surfactant | PEG-12 Dimethicone | 1 | | | | | | | | | | |
| Dow Corning 246 fluid | Cyclohexasiloxane | | | 3 | | 1 | | | | | | |
| D-Panthenol 75 L | Panthenol | | | | | | | 1 | | 0.3 | | 0.5 |
| Dracorin ® CE | Glyceryl Stearate/Citrate | | | | | 3 | | | | | | |
| Dracorin ® GOC | Glyceryl Oleate Citrate, Caprylic Capric Triglyceride | | | | 1.5 | | | | | 0.5 | | |
| Drago-Beta-Glucan | Water (Aqua), Butylene Glycol, Glycerin, Avena Sativa (Oat) Kernel Extract | | | | | 1 | | | | | | |
| DragoCalm ® | Water, Glycerin, Avena Sativa (Oat Kernel Extract) | | | | | | | | 1 | | | |
| Dragocide ® Liquid | Phenoxyethanol, Methylparaben, Ethylparaben, Butylparaben, Propylparaben, Isobutylparaben | | | | | 0.8 | 0.8 | | | | | |
| Dragoderm ® | Glycerin, Triticum Vulgare (Wheat) Gluten, Water (Aqua) | | | | | 2 | | | | | | |
| Dragosan W/O P | Sorbitan Isostearate, Hydrogenated Castor Oil, Ceresin, Beeswax (Cera Alba) | | | | | | 8 | | | | | |
| Dragosantol ® 100 | Bisabolol | | | 0.1 | | 0.2 | | | | | | |

TABLE 1-continued

Compositions of formulations according to the invention (Examples K1 - K11)

| Ingredients | INCI-Name | K1 | K2 | K3 | K4 | K5 | K6 | K7 | K8 | K9 | K10 | K11 |
|---|---|---|---|---|---|---|---|---|---|---|---|---|
| Dragosine ® | Carnosine | 0.2 | | | | | | | 0.2 | | | |
| Dragoxat ® 89 | Ethylhexyl Isononanoate | | 2 | 5 | | 4 | 7 | | 15 | | 5 | |
| EDTA B | Tetrasodium EDTA | | | | | | | | 0.1 | | | |
| EDTA BD | Disodium EDTA | | 0.1 | 0.1 | 0.1 | | | | | | | 0.1 |
| Emulsiphos ® | Potassium Cetyl Phosphate, Hydrogenated Palm Glycerides | | 2 | 2 | | | | | | | | |
| Ethanol | Ethanol | 10 | | | | | | | | | | |
| Extrapone ® Ginkgo Biloba | Propylene Glycol, Water (Aqua), Ginkgo Biloba Leaf Extract, Glucose, Lactic Acid | | | | | | 1 | | | | | |
| Food Color Brown E172+E171 Powder | Color | | | 2 | | | | | | | 3 | |
| Fragrance PFO1 or PFO2 | Parfum | 0.1 | 0.2 | 0.3 | 0.2 | 0.4 | 0.3 | 0.1 | 0.5 | 1 | | 0.1 |
| Frescolat ® MGA | Menthone Glycerin Acetal | | | | | 0.1 | | | | | | |
| Frescolat ® ML | Menthyl Lactate | | | | | | | | | | 0.2 | |
| Fruitapone ® Orange B | Propylene Glycol, Water (Aqua), Citric Acid, Citrus Aurantium Dulcis (Orange) Juice, Trideceth-9, Bisabolol | | | | | | | | | | | 0.5 |
| Glycerine 99.5% | Glycerin | 2.5 | 3 | | | 5 | 3 | | | 0.5 | | 10 |
| Hydrolite ®-5 | Pentylene Glycol | 3 | 2 | | 5 | | | | | 1 | | |
| Hydroviton ®-24 | Water, Pentylene Glycol, Glycerin, Lactic Acid, Sodium Lactate, Serine, Urea, Sorbitol, Sodium Chloride, Allantoin | | | | | 1 | 1 | | 10 | | | |
| Iso Adipat | Diisopropyl Adipate | | | | 1 | | | | 5 | | | |
| Isodragol ® | Triisononanoin | | 2 | | | | | | | | | |
| Isopropyl Palmitate | Isopropyl Palmitate | | | | | | | | | | 13 | |
| Jaguar C-162 | Hydroxypropyl Guar, Hydroxypropyltrimonium Chloride | | | | | | | | | 0.1 | | |
| Jojoba Oil | Simmondsia Chinensis (Jojoba) Seed Oil | 1 | | | | | 2 | | | | | |
| Keltrol CG RD | Xanthan Gum | | 0.4 | 0.2 | 0.2 | 0.1 | | 0.05 | | | | |
| Lanette 16 | Cetyl Alcohol | | 1 | | | | | | | | | |
| Lanette O | Cetearyl Alcohol | | 0.5 | | | 3 | | | | | 5 | |
| Lara Care A-200 | Galactoarabinan | | 0.3 | | | | | | | | | |
| Luviskol K30 Powder | PVP | | | | | | | | | | | 3 |
| Magnesium Sulfate | Magnesium Sulfate | | | | | | 0.7 | | | | | |
| Mineral Oil | Mineral Oil | | | | | | | 8 | ad 100 | | | |
| Neo Heliopan ® 303 | Octocrylene | | 10 | 4 | | | | | | | 10 | |
| Neo Heliopan ® 357 | Butylmethoxydibenzoylmethane | | 3 | 2 | 3 | | | | | | 5 | |
| Neo Heliopan ® AP | Disodium Phenyl Dibenzimidazole Tetrasulfonate | 3 | | | | | | | | | | |

TABLE 1-continued

Compositions of formulations according to the invention (Examples K1 - K11)

| Ingredients | INCI-Name | K1 | K2 | K3 | K4 | K5 | K6 | K7 | K8 | K9 | K10 | K11 |
|---|---|---|---|---|---|---|---|---|---|---|---|---|
| | | % w/w | | | | | | | | | | |
| Neo Heliopan ® AP, 15% sol., neutralized with Biotive ® L-Arginine | Aqua, Disodium Phenyl Dibenzimidazole Tetrasulfonate, Arginin | | 6.7 | 6.7 | | | | | | | | |
| Neo Heliopan ® E 1000 | Isoamyl p.Methoxycinnamate | | 1 | | | | | | | | | |
| Neo Heliopan ® HMS | Homosalate | | 5 | | 5 | | | | | | | |
| Neo Heliopan ® Hydro, 20% sol., neutralized with Biotive ® L-Arginine | Aqua, Phenylbenzimidazole Sulphonic Acid, Arginin | | 10 | 10 | 10 | | | | | | | |
| Neo Heliopan ® MBC | 4-Methylbenzylidene Camphor | 1 | | | | | | | | | | |
| Neo Heliopan ® OS | Ethylhexyl Salicylate | | | 3 | 5 | | | | | | | |
| Neutral Oil | Caprylic/Capric Triglyceride | | | | | 6 | | | | | 13.7 | |
| Ozokerite Wax 2389 | Ozokerite | | | | | | 2 | | | | | |
| PCL-liquid 100 | Cetearyl Ethylhexanoate | | | 2 | | 4 | 5 | | | | | |
| PCL-Solid | Stearyl Heptanoate, Stearyl Caprylate | | | | | 3 | | | 0.5 | | | |
| Phytoconcentrole ® Coconut | Caprylic/Capric Triglyceride, Coconut (Cocos Nucifera) Oil | | | | | | | | 1 | | | |
| Rewoderm Ll S80 | PEG-200 Hydrogenated Palmitate, PEG-7 Glyceryl Cocoate | | | | | | | | | 0.25 | | |
| Rewopol SBFA30 | Disodium Laureth Sulfosuccinate | | | | | | | | | 8 | | |
| Silcare Silicone 41 M65 | Stearyl Dimethicone | | 1 | | | | | | 21 | | | |
| Sodium Chloride | Sodium Chloride | | | | | | | | | 1.7 | | |
| Sodium Hydroxide 10% sol. | Sodium Hydroxide | | | | | 0.9 | | | | | | |
| Solubilizer | PEG-40 Hydrogenated Castor Oil, Trideceth-9, Propylene Glycol, Water (Aqua) | | | | | | | 1.5 | | | | 0.5 |
| SymCalmin ® | Pentylene Glycol, Butylene Glycol, Hydroxyphenyl Propamidobenzois Acid | | | | | 1 | | | | | | |
| SymClariol ® | Decylene Glycol | | | 0.5 | | | | | | | | |
| SymDiol ® 68 | 1,2 Hexanediol, Caprylyl Glycol | 0.6 | | | | | | 1 | | | | |
| SymGlucan ® | Water (Aqua), Glycerin, Beta Glucan | | 2 | | 2 | 1 | | 5 | | | | |
| SymHelios ® 1031 | Benzylidene Dimethoxydimethylindanone | | | 0.5 | 0.5 | | | | | | | |
| SymMatrix ® | Maltodextrin, Rubus Fruticosus (Blackberry) Leaf Extract | | | | | 0.5 | | | | | | |
| SymMollient ® L | Neopentyl Glycol Diisononanoate | | | | 2 | | | | | | 5 | |

TABLE 1-continued

Compositions of formulations according to the invention (Examples K1 - K11)

| Ingredients | INCI-Name | K1 | K2 | K3 | K4 | K5 | K6 | K7 | K8 | K9 | K10 | K11 |
|---|---|---|---|---|---|---|---|---|---|---|---|---|
| | | % w/w | | | | | | | | | | |
| SymMollient ® S | Cetearyl Nonanoate | | | | 1 | | | | | | 4 | |
| SymMollient ® W/S | Trideceth-9, PEG-5 Isononanoate | | | | | | | 2 | | | | |
| SymRelief ® | Bisabolol, Zingiber Officinale (Ginger) Root Extract | | 0.1 | | | 0.2 | | | 0.1 | | | |
| SymRepair ® | Hexyldecanol, Bisabolol, Cetylhydroxyproline Palmitamide, Stearic Acid, Brassica Campestris (Rapeseed Sterols) | | | 1 | | | 3 | | | | | |
| SymSitiye ®1609 | Pentylene Glycol, 4-t-Butylcyclohexanol | | | | | 0.5 | | | | | | |
| SymVital ® | Aloe Barbadensis Leaf Juice Powder, Magnesium Ascorbyl Phosphate, Rubus Idaeus (Raspberry) Leaf Extract | 0.5 | | | | | | 0.1 | | | | |
| Tinosorb S | Bis-Ethylhexyloxyphenol, Methoxyphenyl Triazine | | | | | | | | | | 3 | |
| Tapioca Pure | Tapioca Starch | | 5 | | | | | | | | | |
| TeCe-Ozokerit N502 | Ozokerite | | | | | | | | | | ad 100 | |
| Tego Betain L7 | Cocoamidopropyl Betaine | | | | | | | | | 5 | | |
| Tegosoft TN | C12-15 Alkyl Benzoate | | | | 5 | | | | | | | |
| Texapon N70 | Sodium Laureth Sulfate | | | | | | | | | 15 | | |
| Triethanolamine 99% | Triethanolamine | | | | | | | | | | | 0.5 |
| Vitamin E acetat | Tocopherol Acetate | | 0.5 | 0.5 | 0.5 | | 0.2 | | 0.5 | | 0.7 | |
| Wacker-Belsil CDM3526 VP | C26-C28 Alkyl Dimethicone | | | | | | | | | | 2 | |
| Water, demin. | Water (Aqua) | ad 100 | ad 100 | ad 100 | ad 100 | ad 100 | ad 100 | ad 100 | | ad 100 | | ad 100 |

EXAMPLES: F1-F10

Orally Consumable Use Examples ["Beauty from Inside"]

EXAMPLE F1

Fruit Gums

| | % by weight |
|---|---|
| Water | Ad 100 |
| Saccharose | 34.50 |

-continued

| | % by weight |
|---|---|
| Glucose syrup, DE 40 | 31.89 |
| Iso Syrup C* Tru Sweet 01750 (Cerestar GmbH) | 1.50 |
| Gelatin 240 Bloom | 8.20 |
| Yellow and red food colourants | 0.01 |
| Citric acid | 0.20 |
| Compound of list A | 0.075 |

EXAMPLE F2

Hard Boiled Candy

|  | I (% by weight) | II (% by weight) |
|---|---|---|
| Sugar (Saccharose) | Ad 100 | Ad 100 |
| High fructose corn syrup | 41.00 | 41.00 |
| Maltose | 3.00 | 3.00 |
| Palm kernel oil | 0.90 | 0.90 |
| Citric acid | 0.30 | 0.30 |
| Ginger extract | 0.40 | — |
| Ginseng extract | — | 0.40 |
| Blue colourant | 0.01 | 0.01 |
| Compound of list A | 0.10 | 0.25 |
| Honey | — | 1.50 |
| Honey flavour | — | 0.30 |

EXAMPLE F3

Gelatin Capsules Suitable for Direct Consumption

|  | % by weight | | |
|---|---|---|---|
|  | I | II | III |
| Gelatin shell: | | | |
| Glycerin | 2.014 | 2.014 | 2.014 |
| Gelatin 240 Bloom | 7.91 | 7.91 | 7.91 |
| Aspartame | 0.05 | — | — |
| Sucralose | 0.035 | 0.050 | 0.070 |
| Allura Red (red colourant) | 0.006 | 0.006 | 0.006 |
| Brilliant Blue (blue colourant) | 0.005 | 0.005 | 0.005 |
| Core composition: | | | |
| Plant oil triglyceride (coconut oil fraction) | to 100 | to 100 | to 100 |
| Flavour G | 9.95 | 12.0 | 12.0 |
| Compound of list A | 0.07 | 0.20 | 0.50 |

Flavour G had the following composition here (in wt. %): 0.1% neotam powder, 29.3% peppermint oil arvensis, 29.35% peppermint piperta oil Willamette, 2.97% sucralose, 2.28% triacetin, 5.4% diethyl tartrate, 12.1% peppermint oil yakima, 0.7% ethanol, 3.36% 2-hydroxyethylmenthylcarbonate, 3.0% 2-hydroxypropylmenthylcarbonate, 5.77% D-limonene, 5.67% L-menthylacetate.

The gelatin capsules I, II, III suitable for direct consumption were produced according to WO 2004/050069 and in each case had a diameter of 5 mm and the weight ratio of the core material to the shell material was 90:10. The capsules in each case opened in the mouth within less than 10 seconds and dissolved completely within less than 50 seconds.

EXAMPLE F4

Tablets in Round Tablet Form

|  | % by weight | | |
|---|---|---|---|
|  | I | II | III |
| Magnesium stearate | 0.9 | 0.9 | 0.9 |
| Citric acid | 0.2 | 0.2 | 0.2 |
| Compound of list A | 0.05 | 0.20 | 0.50 |
| Dextrose | to 100 | to 100 | to 100 |

EXAMPLE F5

Chewing Gum (with Sugar and Sugar-Free)

|  | % by weight | |
|---|---|---|
|  | I | II |
| Chewing gum base | 21.0 | 30.0 |
| Glycerin | 0.5 | 1.0 |
| Menthol spearmint eucalyptus flavour P1 | 1.0 | 1.4 |
| Glucose syrup | 16.5 | — |
| Powder sugar | to 100 | — |
| Compound of list A | 0.15 | 0.20 |
| Sorbitol (in powder form) | — | to 100 |
| Palatinit | | 9.5 |
| Xylitol | | 2.0 |
| Mannitol | | 3.0 |
| Aspartame | | 0.1 |
| Acesulfame K | | 0.1 |
| Emulgum (emulsifier) | | 0.3 |
| Sorbitol 70%, in water | | 14.0 |

Flavour P1 had the following composition (in wt. %): 0.05% isobutyraldehyde, 0.05% 3-octanol, 0.05% dimethylsulfide, 0.1% trans-2-hexanal, 0.1% cis-3-hexanol, 0.1% natural 4-terpineol, 0.1% isopulegol, 0.2% natural piperiton, 0.3% linalool, 1.0% isoamylalcohol, 1.0% isovaleraldehyde, 2.5% natural alpha-pinene, 2.5% natural beta-pinene, 8.0% eucalyptol, 7.0% I-menthylacetate, 12.0% 1-menthone, 5.0% isomenthone, 20.5% I-carvone, 39.45% I-menthol.

The Following Table Relates to Examples F6-F10:
Example F6=Instant drink powder
Example F7=Instant drink powder, sugar-free
Example F8=Carbonated lemonade (soft drink)
Example F9=Soya fruit drink
Example F10=Reduced-fat yoghourt

|  | % by weight | | | | |
|---|---|---|---|---|---|
|  | F6 | F7 | F8* | F9 | F10 |
| Compound of list A | 0.50 | 0.70 | 0.10 | 0.05 | 0.20 |
| Sugar (Saccharose) | to 100 | | | | |
| Citric acid | 4.00 | 33.33 | 0.2 | | |
| Trisodiumcitrate | 0.26 | | | | |
| Tricalciumphosphate | 0.22 | | | | |
| Ascorbic acid (Vitamin C) | 0.24 | 0.44 | | | |
| Opacifier and Titanium dioxide (E 171) | 0.20 | | | | |
| Xanthan gum (E 415) | 0.072 | | | | |
| Sodiumcarboxy-methylcellulose (E 467) | 0.064 | | | | |
| Pectin (E 440) | 0.04 | | | | |
| Spray-dried pineapple flavour, contains yellow colourant tartrazine | 0.40 | | | | |
| Spray-dried raspberry flavour, contains red colorant | | 11.50 | | | |
| Lemon-lime flavour | | | 0.01 | | |
| D-Limonene | | | 0.005 | | |
| Maltodextrin (powder) | | to 100 | | | |
| Aspartame | | 3.30 | | | |
| Saccharose | | | 8.0 | 6.0 | 5.0 |
| Hesperetin (1% by weight in 1,2-propyleneglycol) | | | 0.05 | | |

-continued

|  | % by weight | | | | |
| --- | --- | --- | --- | --- | --- |
|  | F6 | F7 | F8* | F9 | F10 |
| Ethylhydroxymethyl furanone |  |  | 0.01 ppb |  |  |
| Vanilla flavour |  |  |  | 0.10 | 0.125 |
| Vanillin |  |  | 15 ppb |  |  |
| Maltol |  |  | 350 ppb |  |  |
| 2,5-dimethyl-4-hydroxy-2H-furan-3-one |  |  | 3 ppb |  |  |
| 1,2-Propylene glycol |  |  | 0.1 |  |  |
| Mixture of fruit juice concentrates |  |  |  | 45.0 |  |
| Soya powder |  |  |  | 5.0 |  |
| Yoghurt (1.5% by weight fat) |  |  |  |  | to 100 |
| Water |  |  | to 100 | to 100 |  |

*Carbon dioxide is added after filling into bottles.

The invention claimed is:

1. A method for lightening skin or for treating hyperpigmentation of the skin comprising applying to the skin 0.001 to 30 wt. % of a carbamate compound selected from the group consisting of:

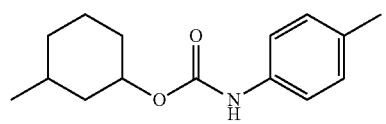
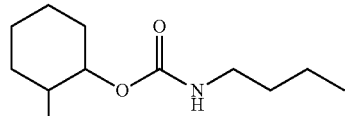
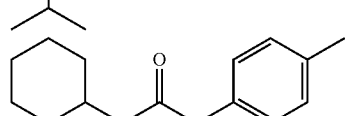
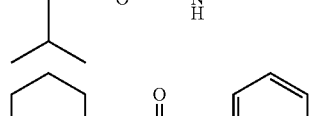
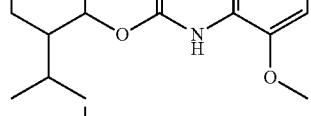
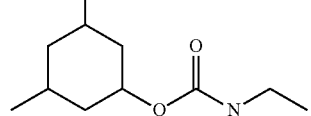
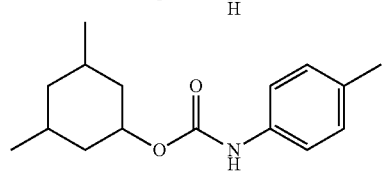
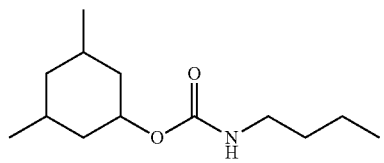
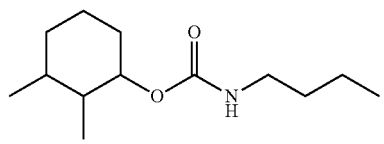
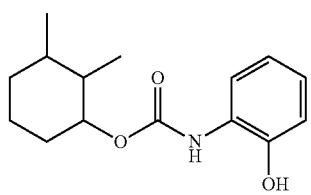
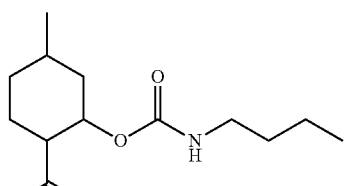
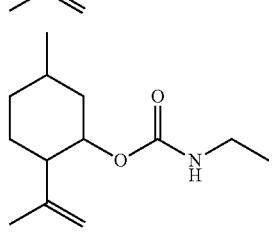
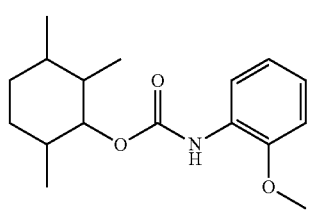
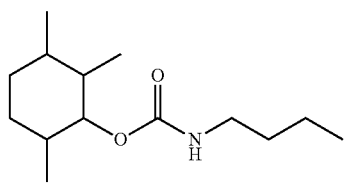
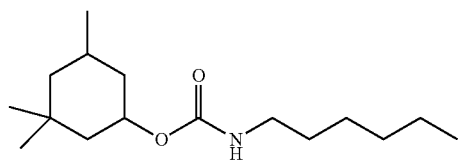
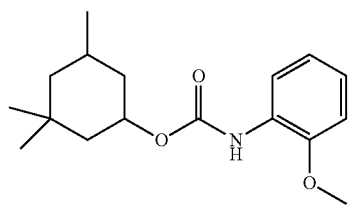

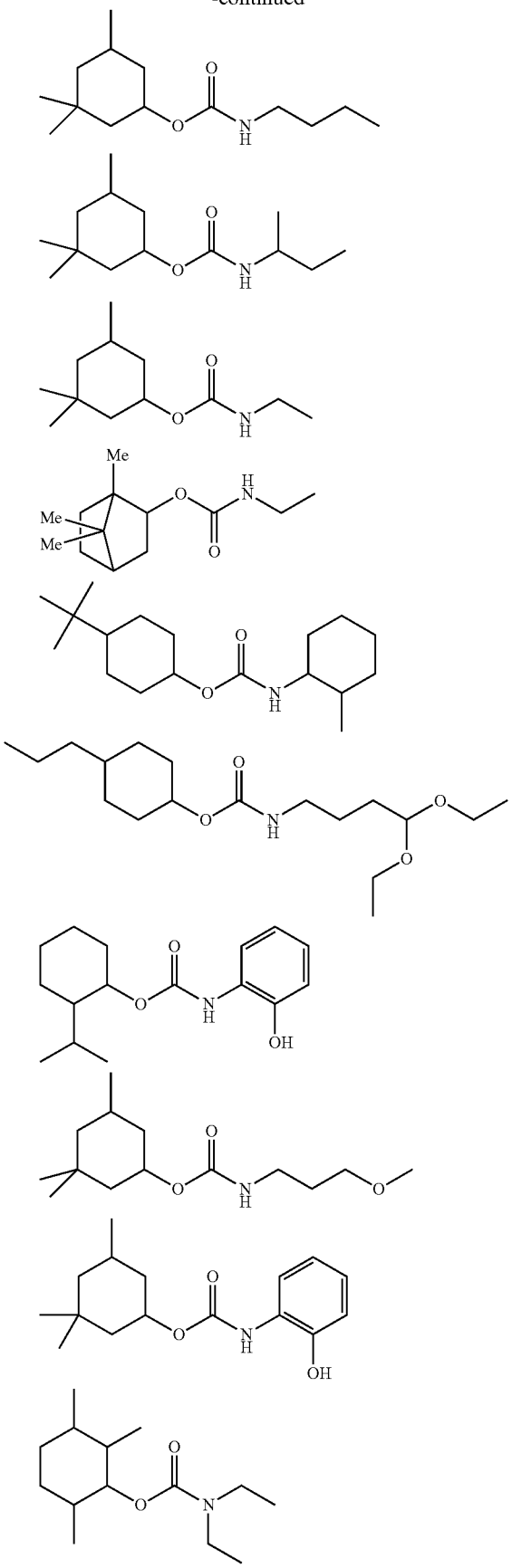

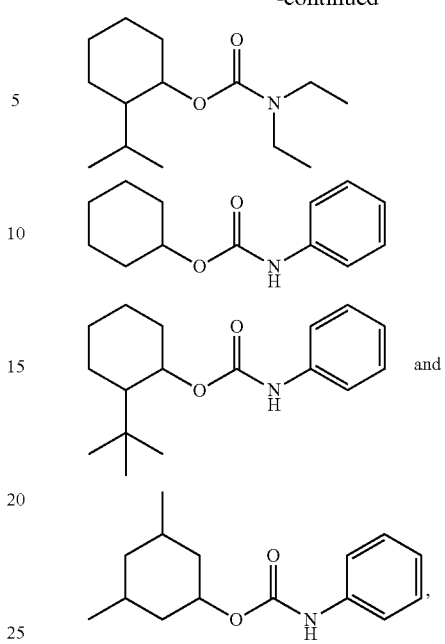

or a cosmetically acceptable salt thereof.

2. The method according to claim 1, wherein the carbamate compound, or cosmetically acceptable salts thereof, is applied to the skin in a cosmetic composition comprising a cosmetically acceptable carrier.

3. The method according to claim 2, wherein the cosmetic composition further comprises one or more additional active ingredients for skin lightening that is not a carbamate compound of claim 2 or a cosmetically acceptable salt thereof.

4. The method according to claim 3, wherein the one or more additional active ingredients for skin lightening are selected from the group consisting of: kojic acid, phenylethyl resorcinol, beta- and alpha-arbutin, hydroquinone, nicotinamide, dioic acid, Mg ascorbyl phosphate and vitamin C and its derivatives, mulberry extract, Bengkoang extract, papaya extract, turmeric extract, nutgrass extract, licorice extract (containing glycyrrhizin), alpha-hydroxy-acids, 4-alkylresorcinols, and 4-hydroxyanisole.

5. The method according to claim 3, wherein the one or more additional active ingredients for skin lightening are tyrosinase inhibitors.

6. The method of claim 3, wherein the total quantity of the one or more additional active ingredients is in the range of from 0.01 to 30 wt. %, based on the total weigh of the cosmetic composition.

7. The method according to claim 2, wherein the total quantity of the carbamate compound, or cosmetically acceptable salt thereof, is in the range of from 0.01 to 5 wt. %, based on the total weigh of the cosmetic composition.

8. The method of claim 3, wherein the total quantity of the one or more additional active ingredients is in the range of from 0.01 to 5 wt. %, based on the total weigh of the cosmetic composition.

9. The method of claim 2, wherein the cosmetic composition comprises the following carbamate compound, or a cosmetically acceptable salt thereof:

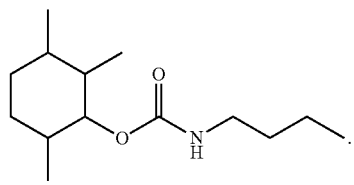 [SMILES: CCCCNC(=O)OC1C(C)CCC(C)C1C]

10. The method of claim 3, wherein the cosmetic composition further comprises one or more agents that absorbs or reflects UV radiation, an anti-irritant, an anti-inflammatory, or an antioxidant.

11. The method of claim 10, wherein the cosmetic composition comprising an agent that absorbs or reflects UV radiation, and the total quantify of the agent that absorbs or reflects UV radiation is in the range of from 0.01 wt. % to 40 wt. %, based on the total the total weight of the cosmetic composition.

12. The method of claim 1, wherein the method is for lightening skin.

13. The method of claim 1, wherein the method is for treating hyperpigmentation of the skin.

14. The method of claim 10, wherein the cosmetic composition comprises from 0.01 wt. % to 40 wt. %, based on the total weight of the cosmetic composition, of agents that absorb or reflect UV radiation.

\* \* \* \* \*